US008158385B2

(12) United States Patent  
Ozaki et al.

(10) Patent No.: US 8,158,385 B2  
(45) Date of Patent: Apr. 17, 2012

(54) CELL DEATH-INDUCING AGENT

(75) Inventors: Shuji Ozaki, Tokushima (JP); Masahiro Abe, Tokushima (JP); Masayuki Tsuchiya, Shizuoka (JP); Naoki Kimura, Shizuoka (JP); Shigeto Kawai, Shizuoka (JP)

(73) Assignees: Chugai Seiyaku Kabushiki Kaisha, Tokyo (JP); Shuji Ozaki, Tokushima (JP); Masahiro Abe, Tokushima (JP)

( * ) Notice: Subject to any disclaimer, the term of this patent is extended or adjusted under 35 U.S.C. 154(b) by 225 days.

(21) Appl. No.: 10/530,696

(22) PCT Filed: Oct. 10, 2003

(86) PCT No.: PCT/JP03/13063
§ 371 (c)(1),
(2), (4) Date: Oct. 28, 2005

(87) PCT Pub. No.: WO2004/033499
PCT Pub. Date: Apr. 22, 2004

(65) Prior Publication Data
US 2006/0275301 A1 Dec. 7, 2006

(30) Foreign Application Priority Data
Oct. 11, 2002 (JP) ................................ 2002-299289

(51) Int. Cl.
*C12P 21/04* (2006.01)
*C12P 21/08* (2006.01)
(52) U.S. Cl. .................................... 435/69.6; 530/387.3
(58) Field of Classification Search ........................ None
See application file for complete search history.

(56) References Cited

U.S. PATENT DOCUMENTS

| | | | |
|---|---|---|---|
| 4,946,778 A | 8/1990 | Ladner et al. | |
| 5,077,216 A | 12/1991 | Morganelli et al. | |
| 5,223,241 A | 6/1993 | Isobe et al. | |
| 5,516,672 A | 5/1996 | Yamasaki et al. | |
| 5,618,920 A | 4/1997 | Robinson et al. | |
| 5,747,654 A * | 5/1998 | Pastan et al. ............... | 530/391.7 |
| 5,780,021 A | 7/1998 | Sobel | |
| 5,789,554 A | 8/1998 | Leung et al. | |
| 5,837,242 A | 11/1998 | Holliger et al. | |
| 5,837,821 A | 11/1998 | Wu | |
| 5,840,344 A | 11/1998 | Fukushima | |
| 5,877,291 A | 3/1999 | Mezes et al. | |
| 5,885,574 A | 3/1999 | Elliott | |
| 5,892,020 A | 4/1999 | Mezes et al. | |
| 5,977,322 A | 11/1999 | Marks et al. | |
| 6,126,980 A | 10/2000 | Smith et al. | |
| 6,183,744 B1 | 2/2001 | Goldenberg | |
| 6,323,000 B2 | 11/2001 | Briggs et al. | |
| 6,342,220 B1 | 1/2002 | Adams et al. | |
| 6,361,769 B1 | 3/2002 | Tovey | |
| 6,368,596 B1 | 4/2002 | Ghetie et al. | |
| 6,579,692 B1 | 6/2003 | Fukushima | |
| 6,683,157 B2 | 1/2004 | Briggs et al. | |
| 6,699,686 B1 | 3/2004 | Brocard et al. | |
| 6,719,972 B1 | 4/2004 | Gribben et al. | |
| 6,759,043 B2 | 7/2004 | Fukushima | |
| 7,115,373 B2 | 10/2006 | Hashida et al. | |
| 7,262,278 B2 | 8/2007 | Tawara et al. | |
| 7,456,260 B2 | 11/2008 | Rybak et al. | |
| 7,691,588 B2 | 4/2010 | Tsuchiya et al. | |
| 7,749,501 B2 | 7/2010 | Gelfand | |
| 2001/0006796 A1 | 7/2001 | Briggs et al. | |
| 2002/0028178 A1 | 3/2002 | Hanna et al. | |
| 2002/0193571 A1 | 12/2002 | Carter et al. | |
| 2002/0197706 A1 | 12/2002 | Nadkarni et al. | |
| 2003/0073161 A1 | 4/2003 | Briggs et al. | |
| 2003/0082612 A1 | 5/2003 | Snodgrass et al. | |
| 2003/0103979 A1 | 6/2003 | Leung et al. | |
| 2003/0147894 A1 | 8/2003 | Fukushima et al. | |
| 2003/0148409 A1 | 8/2003 | Rossi et al. | |
| 2003/0157100 A1 | 8/2003 | Fukushima et al. | |
| 2003/0157577 A1 | 8/2003 | Fukushima et al. | |
| 2003/0190316 A1 | 10/2003 | Kakuta et al. | |
| 2003/0202975 A1 | 10/2003 | Tedder | |
| 2003/0211108 A1 | 11/2003 | Fukushima et al. | |
| 2004/0001828 A1 | 1/2004 | Tuscano et al. | |
| 2004/0058393 A1 | 3/2004 | Fukishima et al. | |

(Continued)

FOREIGN PATENT DOCUMENTS

AU          755822       3/1999

(Continued)

OTHER PUBLICATIONS

Fayen, J., Huang, J-H., Ferrone, S., and Tykocinski, M.L. Negative signaling by anti-HLA class I antibodies is dependent upon two triggering events. International Immunology. 1998, vol. 10 No. 9. pp. 1347-1358.* Hudson, P.J. and Kortt, A.A. High avidity scFv multimers; diabodies and triabodies. 1999, Journal of Immunological Methods, vol. 231 pp. 177-189.*

De Felice, M., Turc, M.C., Giarrusso, P.C., Corbo, L., Pizzano, R., Martinelli, V., Ferrone, S., and Venuta, S. Differential regulatory role of monomorphic and polymorphic determinants of histocompatibility leukocyte antigen class I antigens in monoclonal antibody OKT3-induced T cell proliferation.1987, Jnl of Immun. vol. 139 No. 8, pp. 2683-2689.*

Wu, A.M., Chen, W., Raubitschek, A., Williams, L.E., Neumaier, M., Fischer, R., Hu, S., Odom-Maryon, T., Wong, J., and Shively, J.E. Tumor localization of anit-CEA single-chain Fvs: improved targeting by non-covalent dimers. 1996, Immunotechnology vol. 2 pp. 21-36.*

(Continued)

*Primary Examiner* — Anne M. Gussow
(74) *Attorney, Agent, or Firm* — Fish & Richardson P.C.

(57) ABSTRACT

To identify antigens of the 2D7 antibody, the present inventors cloned the 2D7 antigen. The results suggested that the 2D7 antigen is an HLA class I molecule. Based on this finding, the present inventors examined whether the 2D7 antibody has cell death-inducing activity. Nuclei fragmentation was observed when the 2D7 antibody was cross-linked with another antibody, indicating that cell-death was induced. Further, diabodies of the 2D7 antibody were found to have very strong cell death-inducing activities, even without the addition of another antibody. These results indicate that minibodies of an HLA-recognizing antibody can be used as cell death-inducing agents.

9 Claims, 37 Drawing Sheets

U.S. PATENT DOCUMENTS

| | | | |
|---|---|---|---|
| 2004/0073013 A1 | 4/2004 | Fukushima et al. |
| 2004/0091475 A1 | 5/2004 | Tsuchiya et al. |
| 2004/0180002 A1 | 9/2004 | Young et al. |
| 2004/0242847 A1 | 12/2004 | Fukushima et al. |
| 2005/0130224 A1 | 6/2005 | Saito et al. |
| 2005/0214278 A1 | 9/2005 | Kakuta et al. |
| 2005/0220787 A1 | 10/2005 | Lobo |
| 2005/0267222 A1 | 12/2005 | Iwata et al. |
| 2006/0189794 A1 | 8/2006 | Tsuchiya et al. |
| 2006/0222643 A1 | 10/2006 | Tsunoda et al. |
| 2007/0003556 A1 | 1/2007 | Tsuchiya et al. |
| 2007/0087381 A1 | 4/2007 | Kojima |
| 2007/0280951 A1 | 12/2007 | Kimura et al. |
| 2007/0281327 A1 | 12/2007 | Nakano et al. |
| 2008/0009038 A1 | 1/2008 | Ohtomo et al. |
| 2008/0107654 A1 | 5/2008 | Kikuchi et al. |
| 2008/0206229 A1 | 8/2008 | Ono et al. |
| 2008/0248037 A1 | 10/2008 | Li et al. |
| 2008/0274110 A1 | 11/2008 | Ozaki et al. |
| 2008/0286280 A1 | 11/2008 | Kallmeyer et al. |
| 2009/0022687 A1 | 1/2009 | Matsumoto et al. |
| 2009/0028854 A1 | 1/2009 | Igawa et al. |
| 2009/0117097 A1 | 5/2009 | Igawa et al. |
| 2009/0162352 A1 | 6/2009 | Adler et al. |
| 2009/0297501 A1 | 12/2009 | Igawa et al. |
| 2009/0311718 A1 | 12/2009 | Fukushima et al. |
| 2010/0092457 A1 | 4/2010 | Aburatani et al. |
| 2010/0092461 A1 | 4/2010 | Matsumoto et al. |
| 2010/0150927 A1 | 6/2010 | Kimura et al. |

FOREIGN PATENT DOCUMENTS

| | | |
|---|---|---|
| AU | 2004/297111 | 6/2005 |
| AU | 2002/210917 | 5/2006 |
| CA | 2272245 | 5/1998 |
| CN | 1244805 | 2/2000 |
| EP | 437 622 | 7/1991 |
| EP | 0 562 125 | 9/1993 |
| EP | 0 721 015 | 7/1996 |
| EP | 1 035 132 | 9/2000 |
| EP | 1 327 680 A1 | 7/2003 |
| EP | 1 327 681 | 7/2003 |
| EP | 1369431 A1 | 12/2003 |
| EP | 1 396 500 | 3/2004 |
| EP | 1561759 | 8/2005 |
| EP | 1712565 | 10/2006 |
| EP | 1757686 | 2/2007 |
| EP | 1 900 814 | 3/2008 |
| EP | 1 262 548 | 8/2008 |
| JP | 3-41033 | 2/1991 |
| JP | 7-503622 | 4/1995 |
| JP | 7236475 | 9/1995 |
| JP | 10-505231 | 5/1998 |
| JP | 10508868 | 9/1998 |
| JP | 10-510842 | 10/1998 |
| JP | 11-500916 | 1/1999 |
| JP | 11-092500 | 4/1999 |
| JP | 2000-95800 | 4/2000 |
| JP | 2001/506135 | 5/2001 |
| JP | 2001/513999 | 9/2001 |
| JP | 2001-518930 | 10/2001 |
| JP | 2002-544173 | 12/2002 |
| JP | 2004-086862 | 3/2004 |
| JP | 2004-292455 | 10/2004 |
| JP | 2005529616 | 10/2005 |
| MX | 9905856 A | 7/2000 |
| WO | WO 91/00739 | 1/1991 |
| WO | WO 91/16928 | 11/1991 |
| WO | WO 92/19759 | 11/1992 |
| WO | WO 93/06862 | 4/1993 |
| WO | WO 94/13806 | 6/1994 |
| WO | WO 96/04925 | 2/1996 |
| WO | WO 96/26648 | 9/1996 |
| WO | WO 96/36360 | 11/1996 |
| WO | WO 96/40218 | 12/1996 |
| WO | WO 97/01633 | 1/1997 |
| WO | WO 97/31108 | 8/1997 |
| WO | WO 97/32601 | 9/1997 |
| WO | WO9734632 | 9/1997 |
| WO | WO 98/22136 | 5/1998 |
| WO | WO 98/28331 | 7/1998 |
| WO | WO 98/44001 | 8/1998 |
| WO | WO 98/41641 | 9/1998 |
| WO | WO 98/42378 | 10/1998 |
| WO | WO 99/02567 | 1/1999 |
| WO | WO 99/03495 | 1/1999 |
| WO | WO 99/10494 | 3/1999 |
| WO | WO 99/12973 | 3/1999 |
| WO | WO 99/17364 | 4/1999 |
| WO | WO 00/23593 | 4/2000 |
| WO | WO 00/53634 | 9/2000 |
| WO | WO 00/67795 | 11/2000 |
| WO | WO 00/75191 | 12/2000 |
| WO | WO 01/36486 | 5/2001 |
| WO | WO 01/64713 | 9/2001 |
| WO | WO 01/66737 | 9/2001 |
| WO | WO 01/74388 | 10/2001 |
| WO | WO 01/77342 | 10/2001 |
| WO | WO 01/79494 | 10/2001 |
| WO | WO 01/87337 | 11/2001 |
| WO | WO 01/97858 | 12/2001 |
| WO | WO 02/04021 | 1/2002 |
| WO | WO 02/22212 | 3/2002 |
| WO | WO 02/33072 | 4/2002 |
| WO | WO 02/33073 | 4/2002 |
| WO | WO0228894 | 4/2002 |
| WO | WO 02/078612 | 10/2002 |
| WO | WO 02/094880 | 11/2002 |
| WO | WO 02/096457 | 12/2002 |
| WO | WO 02/097033 | 12/2002 |
| WO | WO03002607 A1 | 1/2003 |
| WO | WO 03/033538 | 4/2003 |
| WO | WO 03/033654 | 4/2003 |
| WO | WO 03/086324 | 10/2003 |
| WO | WO 03/104425 | 12/2003 |
| WO | WO 03/107218 | 12/2003 |
| WO | WO 2004/003019 | 1/2004 |
| WO | WO 2004/033499 | 4/2004 |
| WO | WO 2004/037293 | 5/2004 |
| WO | WO 2004/081048 | 9/2004 |
| WO | WO 2004/087763 | 10/2004 |
| WO | WO2005004912 | 1/2005 |
| WO | WO 2005/056602 | 6/2005 |
| WO | WO 2005/056603 | 6/2005 |
| WO | WO 2005/056604 | 6/2005 |
| WO | WO 2005/056605 | 6/2005 |
| WO | WO 2005/056798 | 6/2005 |
| WO | WO 2005/100560 | 10/2005 |
| WO | WO 2006/123724 | 11/2006 |
| WO | WO2008007755 | 1/2008 |
| WO | WO 2008/071394 | 6/2008 |

OTHER PUBLICATIONS

Goto, T., Kennel, S.J., Abe, M., Takishita, M., Kosaka, M., Solomon, A., and Saito, S. A novel membrane antigen selectively expressed on terminally differentiated human B cells. 1994, Blood. vol. 84 No. 6 pp. 1922-1930.*

De Nardo, D.G., Xiong, C., Shi, X., De Nardo, G.L., and De Nardo, S. Anti-HLA-DR/anti-DOTA diabody construction in a modular gene design platform: bispecific antibodies for pretargeted radioimmunotherapy. 2001, Cancer Biotherapy and Radiopharmaceuticals vol. 16 No. 6, pp. 525-535.*

Ledbetter, Francisco, Siegall, Gilliand, Hollenbaugh, Aruffo, Siadak, Mischel-Petty, Grosmaire, Gordon, Brown, Moran-Davis, Mittler, Kiener, and Nadler. Agonistic activity of a CD40-specific single-chain Fv constructed from the variable regions of mAb G28-5. Critical Reviews in Immunology, 1997. vol. 17, pp. 427-435.*

Kimura, Kawai, Kinoshita, Ishiguro, Azuma, Ozaki, Abe, Sugimoto, Hirata, Orita, Okabe, Matsumoto, and Tsuchiya. 2D7 diabody bound to the a2 domain of HLA class I efficiently induces caspase-independent cell death against malignant and activated lymphoid cells. Biochemical and Biophysical Research Communications, 2004. vol. 325, pp. 1201-1209.*

Reff, M.E., and Heard, C. A review of modifications to recombinant antibodies: attempt to increase efficacy in oncology applications. Critical Reviews in Oncology and Hematology, 2001. vol. 40, pp. 25-35.*

Ballmaier et al., "c-mpl mutations are the cause of congenital amegakaryocytic thrombocytopenia," *Blood*, 97:139-146 (2001).

Brinkman et al., "FTY720: targeting G-protein-coupled receptors for sphingosine 1-phosphate in transplantation and autoimmunity," *Curr. Opin. Immunol.*, 14:569-575 (2002).

Bruenke et al., "A recombinant bispecific single-chain Fv antibody against HLA class II and FcγRIII (CD16) triggers effective lysis of lymphoma cells," *Br. J. Haematol.*, 125:167-179 (2004).

Clark, "CD22, a B Cell-Specific Receptor, Mediates Adhesion and Signal Transduction," *J. Immunol.*, 150:4715-4718 (1993).

Co et al., "A Humanized Antibody Specific for the Platelet Integrin gpIIb/IIIa," *J. Immunol.*, 152:2968-2976 (1994).

Deng et al., "An Agonist Murine Monoclonal Antibody to the Human c-Mpl Receptor Stimulates Megakaryocytopoiesis," *Blood*, 92:1981-1988 (1998).

Ebert et al., "Expression of Metallothionein II in Intestinal Metaplasia, Dysplasia, and Gastric Cancer," *Cancer Res.*, 60:1995-2001 (2000).

Elliott et al., "Activation of the Erythropoietin (EPO) Receptor by Bivalent Anti-EPO Receptor Antibodies," *J. Biol. Chem.*, 271:24691-24697 (1996).

Ghetie et al., "Homodimerization of tumor-reactive monoclonal antibodies markedly increases their ability to induce growth arrest or apoptosis of tumor cells," *Proc. Natl. Acad. Sci. USA*, 94:7509-7514 (1997).

Goel et al., "$^{99m}$Tc- Labeled Divalent and Tetravalent CC49 Single-Chain Fv's: Novel Imaging Agents for Rapid In Vivo Localization of Human Colon Carcinoma," *J. Nucl. Med.*, 42:1519-1527 (2001).

Goel et al., "Genetically Engineered Tetravalent Single-Chain Fv of the Pancarcinoma Monoclonal Antibody CC49: Improved Biodistribution and Potential for Therapeutic Application," *Cancer Res.*, 60:6964-6971 (2000).

Hudson et al., "High avidity scFv multimers; diabodies and triabodies," *J. Immunol. Methods*, 231:177-189 (1999).

Kipriyanov et al., "Effect of Domain Order on the Activity of Bacterially Produced Bispecific Single-chain Fv Antibodies," *J. Mol. Biol.*, 330:99-111 (2003).

Kortt et al., "Dimeric and trimeric antibodies: high avidity scFvs for cancer targeting," *Biomol. Eng.*, 18:95-108 (2001).

Lebrun et al., "Antibodies to the Extracellular Receptor Domain Restore the Hormone-insensitive Kinase and Conformation of the Mutant Insulin Receptor Valine 382," *J. Biol. Chem.*, 268:11272-11277(1993).

Li et al., "The Epitope Specificity and Tissue Reactivity of Four Murine Monoclonal Anti-CD22 Antibodies," *Cell. Immunol.*, 118:85-99 (1989).

Matsuoka et al., "A Monoclonal Antibody to the α2 Domain of Murine Major Histocompatibility Complex Class I that Specifically Kills Activated Lymphocytes and Blocks Liver Damage in the Concanavalin A Hepatitis Model," *J. Exp. Med.*, 198:497-503 (2003).

Nishii, "CD22 antibody therapy," *Current Therapy*, 20:47-50 (2001) (English translation included).

Orita et al., "A novel therapeutic approach for thrombocytopenia by minibody agonist of the thrombopoietin receptor," *Blood*, 105:562-566 (2005).

Ozaki et al., "A Recombinant HLA Class I-Specific Single Chain Fv Diabody Induces Cell Death in Human Lymphoid Malignancies," *Blood*, 102:933a, Abstract No. 3474 (2003).

Rossi et al., "Development of New Multivalent-bispecific Agents for Pretargeting Tumor Localization and Therapy," *Clin. Cancer Res.*, 9:3886s-3896s (2003).

Sato et al., "CD22 Is Both a Positive and Negative Regulator of B Lymphocyte Antigen Receptor Signal Transduction: Altered Signaling in CD22-Deficient Mice," *Immunity*, 5:551-562 (1996).

Scheurle et al., "Cancer Gene Discovery Using Digital Differential Display," *Cancer Res.*, 60:4037-4043 (2000).

Smith et al., "Inhibition of T Cell Activation by a Monoclonal Antibody Reactive Against the α3 Domain of Human MHC Class I Molecules," *J. Immunol.*, 153:1054-1067 (1994).

Tahtis et al., "Biodistribution Properties of $^{111}$Indium-labeled C-Functionalized trans-Cyclohexyl Diethylenetriaminepentaacetic Acid Humanized 3S193 Diabody and F(ab')$_2$ Constructs in a Breast Carcinoma Xenograft Model," *Clin. Cancer Res.*, 7:1061-1072 (2001).

Tedder et al., "CD22, a B Lymphocyte-Specific Adhesion Molecule That Regulates Antigen Receptor Signaling," *Annu. Rev. Immunol.*, 15:481-504 (1997).

Thilenius et al., "Agonist antibody and Fas ligand mediate different sensitivity to death in the signaling pathways of Fas and cytoplasmic mutants," *Eur. J. Immunol.*, 27:1108-1114 (1997).

Xiong et al., "Efficient inhibition of human B-cell lymphoma xenografts with an anti-CD20 X anti-CD3 bispecific diabody," *Cancer Lett.*, 177:29-39 (2002).

Xu et al., "Insight into hepatocellular carcinogenesis at transcriptome level by comparing gene expression profiles of hepatocellular carcinoma with those of corresponding noncancerous liver," *Proc. Natl. Acad. Sci. USA*, 98:15089-15094 (2001).

Daniel et al., "Induction of Apoptosis in Human Lymphocytes by Human Anti-HLA Class I Antibodies," *Transplantation*, 75:1380-1386 (2003).

Fayen et al., "Negative signaling by anti-HLA class I antibodies is dependent upon two triggering events," *Int. Immunol.*, 10:1347-1358 (1998).

Funaro et al., "Monoclonal antibodies and therapy of human cancers," *BiotechnoL Adv.*, 18:385-401 (2000).

Genestier et al., "Antibodies to HLA Class 1 α1 Domain Trigger Apoptosis of CD40-Activated Human B Lymphocytes," *Blood*, 90:726-735 (1997).

Genestier et al., "Caspase-dependent Ceramide Production in Fas- and HLA Class I-mediated Peripheral T Cell Apoptosis," *J. Biol. Chem.*, 273:5060-5066 (1998).

Genestier et al., "Fas-Independent Apoptosis of Activated T Cells Induced by Antibodies to the HLA Class I α1 Domain," *Blood*, 90:3629-3639 (1997).

Genestier et al., "T cell sensitivity to HLA class I-mediated apoptosis is dependent on interleukin-2 and interleukin-4," *Eur. J. Immunol.*, 27:495-499 (1997).

Goto et al., "A Novel Membrane Antigen Selectively Expressed on Terminally Differentiated Human B Cells," *Blood*, 84:1922-1930 (1994).

Holliger et al., "'Diabodies': Small bivalent and bispecific antibody fragments," *Proc. Natl. Acad. Sci. USA*, 90:6444-6448 (1993).

Hu et al., "Minibody: A Novel Engineered Anti-Carcinoembryonic Antigen Antibody Fragment (Single-Chain Fv-$C_H3$) Which Exhibits Rapid, High-Level Targeting of Xenografts," *Cancer Res.*, 56:3055-3061 (1996).

Kimura et al., "2D7 diabody bound to the α2 domain of HLA class I efficiently induces caspase-independent cell death against malignant and activated lymphoid cells," *Biochem. Biophys. Res. Commun.*, 325:1201-1209 (2004).

Kreitman et al., "Cytotoxic Activity of Disulfide-stabilized Recombinant Immunotoxin RFB4(dsFv)-PE38 (BL22) toward Fresh Malignant Cells from Patients with B-Cell Leukemias," *Clin. Cancer Res.*, 6:1476-1487 (2000).

Kulkarni et al., "Construction of a Single-Chain Antibody Derived From 5H7, A Monoclonal Antibody Specific for a Death Signaling Domain of Human Class I Major Histocompatibility Complex," *Transplant. Proc.*, 30:1081 (1998).

Kulkarni et al., "Programmed Cell Death Signaling Via Cell-Surface Expression of a Single-Chain Antibody Transgene," *Transplantation*, 69:1209-1217 (2000).

Matsuoka et al., "A Novel Type of Cell Death of Lymphocytes Induced by a Monoclonal Antibody without Participation of Complement," *J. Exp. Med.*, 181:2007-2015 (1995).

Ohtomo et al., "Molecular Cloning and Characterization of a Surface Antigen Preferentially Overexpressed on Multiple Myeloma Cells," *Biochem. Biophys. Res. Commun.*, 258:583-591 (1999).

Oka, "Development of Novel Immunotoxin Using Recombinant Alpha-Sarcin and Its Application Treatment of Hematopoietic Tumor," *Sankyo Seimei Kagaku Kenkyu Shinko Zaidan Kenkyu Hokokushu*, 12:46-56 (1998) (concise English explanation included).

Ono et al., "The humanized anti-HM1.24 antibody effectively kills multiple myeloma cells by human effector cell-mediated cyto-toxicity," *Mol. Immunol.*, 36:387-395 (1999).

Ozaki et al., "Humanized Anti-HM1.24 Antibody Mediates Myeloma Cell Cytotoxicity That is Enhanced by Cytokine Stimulation of Effector Cells," *Blood*, 93:3922-3930 (1999).

Ozaki et al., "Immunotherapy of Multiple Myeloma With a Monoclonal Antibody Directed Against a Plasma Cell-Specific Antigen, HM1.24," *Blood*, 90:3179-3186 (1997).

Pettersen et al., "The TCR-Binding Region of the HLA Class I $\alpha_2$ Domain Signals Rapid Fas-Independent Cell Death: A Direct Pathway for T Cell-Mediated Killing of Target Cells?" *J. Immunol.*, 160:4343-4352 (1998).

Plückthun et al., "New protein engineering approaches to multivalent and bispecific antibody fragments," *Immunotechnology*, 3:83-105 (1997).

Woodle et al., "Anti-Human Class I $\alpha$3 Domain-Specific Monoclonal Antibody Induces Programmed Cell Death in Murine Cells Expressing Human Class I MHC Transgenes," *Transplant. Proc.*, 30:1059-1060 (1998).

Woodle et al., "Anti-Human Class I MHC Antibodies Induce Apoptosis by a Pathway That Is Distinct from the Fas Antigen-Mediated Pathway," *J. Immunol.*, 158:2156-2164 (1997).

Woodle et al., "Class I MHC Mediates Programmed Cell Death in Human Lymphoid Cells," *Transplantation*, 64:140-146 (1997).

Kikuchi et al., "A bivalent single-chain Fv fragment against CD47 induces apoptosis for leukemic cells," *Biochem. Biophys. Res. Commun.*, 315:912-918 (2004).

Piétri-Rouxel et al., "The biochemical effect of the naturally occurring Trp64→ Arg mutation on human β3-adrenoceptor activity," *Eur. J. Biochem.*, 247:1174-1179.

Rudikoff et al., "Single amino acid substitution altering antigen-binding specificity", Proc. Natl. Acad. Sci. USA, 79:1979-1983, 1982.

De Pascalis et al., "Grafting of 'abbreviated' complementary-determining regions containing specificity-determining residues essential for ligand contact to engineer a less immunogenic humanized monoclonal antibody", Journal of Immunology 169:3076-3084, 2002.

Casset et al., "A peptide mimetic of an anti-CD4 monoclonal antibody by rational design", Biochemical and Biophysical Research Communications 307:198-205, 2003.

Vajdos et al., "Comprehensive functional maps of the antigen-binding site of an anti-ErbB2 antibody obtained with shotgun scanning mutagenesis", Journal of Molecular Biology 320:415-428, 2002.

Wu et al., "Humanization of a murine monoclonal antibody by simultaneous optimization of framework and CDR residues", Journal of Molecular Biology 294:151-162, 1999.

MacCallum et al., "Antibody-antigen interactions: Contact analysis and binding site topography", Journal of Molecular Biology 262:732-745, 1996.

Holm et al., "Functional mapping and single chain construction of the anti-cytokeratin 8 monoclonal antibody TS1", Molecular Immunology 44:1075-1084, 2007.

Chen et al., "Selection and analysis of an optimized anti-VEGF antibody: Crystal structure of an affinity-matured Fab in complex with antigen", Journal of Molecular Biology 293:865-881, 1999.

Skolnick et al., "From genes to protein structure and function: novel applications of computational approaches in the genomic era", Trends in Biotechnology 18:34-39, 2000.

USPTO Notice of Allowance in U.S. Appl. No. 10/551,504, mailed Jan. 7, 2010, 46 pages.

Fish & Richardson P.C., Amendment in Reply to Office Action dated Sep. 15, 2009 in U.S. Appl. No. 10/582,304, filed Jan. 13, 2010, 13 pages.

U.S. Appl. No. 12/307,042, Kimura et al.

Arndt et al., "Factors Influencing the Dimer to Monomer Transition of an Antibody Single-Chain Fv Fragment," *Biochemistry*, 37:12918-12926 (1998).

Avent et al., "Monoclonal antibodies that recognize different membrane proteins that are deficient in Rhnull human erythrocytes. One group of antibodies reacts with a variety of cells and tissues whereas the other group is erythroid-specific," *Biochem. J.*, 251:499-505 (1988).

Bartley et al., "Identification and Cloning of a Megakaryocyte Growth and Development Factor That is a Ligand for the Cytokine Receptor Mpl," *Cell*, 77:1117-1124 (1994).

Bazil et al., "Apoptosis of human hematopoietic progenitor cells induced by crosslinking of surface CD43, the major sialoglycoprotein of leukocytes," *Blood*, 86:502-511 (1995).

Bazzoni et al., "Chimeric tumor necrosis factor receptors with constitutive signaling activity," *Proc. Natl. Acad. Sci. USA*, 92(12):5376-5580 (1995).

Beresford et al., "Binding Characteristics and Tumor Targeting of a Covalently Linked Divalent CC49 Single-Chain Antibody," *Int. J. Cancer*, 81:911-917 (1999).

Berger et al., "Inhibition of intractable nucleases with ribonucleoside-vanadyl complexes: isolation of messenger ribonucleic acid from resting lymphocytes," *Biochemistry*, 18(23):5143-5149 (1979).

Bodmer et al., "TRAIL Receptor-2 Signals Apoptosis Through FADD and Caspase-8," *Nat. Cell Biol.*, 2:241-243 (2000).

Borden et al., "Lymphokines and Cytokines as Cancer Treatment," *Cancer*, 65:800-814 (1990).

Bowie et al., "Deciphering the Message in Protein Sequences: Tolerance to Amino Acid Substitutions," *Science*, 247:1306-1310 (1990).

Brown et al., "Integrin-associated protein: a 50-kD plasma membrane antigen physically and functionally associated with integrins," *J. Cell Biology*, 111(6 Pt 1):2785-2794 (1990).

Brown et al., "Integrin-associated protein (CD47) and its ligands," *Trends Cell Biology*, 11(3):130-135 (2001).

Buchsbaum et al., "Antitumor Efficacy of TRA-8 Anti-DR5 Monoclonal Antibody Alone or in Combination with Chemotherapy and/or Radiation Therapy in a Human Breast Cancer Model," *Clin. Cancer Res.*, 9:3731-3741 (2003).

Burgess et al., "Possible dissociation of the heparin-binding and mitogenic activities of heparin-binding (acidic fibroblast) growth factor-1 from its receptor-binding activities by site-directed mutagenesis of a single lysine residue," *J. Cell Biol.*, 111:2129-2138 (1990).

Burthem et al., "Hairy cell interactions with extracellular matrix: expression of specific integrin receptors and their role in the cell's response to specific adhesive proteins," *Blood*, 84(3):873-882 (1994).

Byers, "What Can Randomized Controlled Trials Tell us About Nutrition and Cancer Prevention?," CA Cancer J. Clin., 49:353-361 (1999).

Caldas et al., "Humanization of the anti-CD18 antibody 6.7: an unexpected effect of a framework residue in binding to antigen," *Mol. Immunol.*, 39:941-952 (2003).

Chien et al., "Significant structural and functional change of an antigen-binding site by a distant amino acid substitution: Proposal of a structural mechanism," *Proc. Nat. Acad. Sco. USA*, 86:5532-5536 (1989).

Chirgwin et al., "Isolation of biologically active ribonucleic acid from sources enriched in ribonuclease," *Biochemistry*, 18(24):5294-5299 (1979).

Chuntharapai et al. "Isotype-Dependent Inhibition of Tumor Growth In Vivo by Monoclonal Antibodies to Death Receptor 4," *J. Immunol.*, 166:4891-4898 (2001).

Cochlovius et al., "Cure of Burkitt's Lymphoma in Severe Combined Immunodeficiency Mice by T Cells, Tetravalent CD3 × CD19 Tandem Diabody and CD28 Costimulation," *Cancer Res.*, 60:4336-4341 (2000).

Cooper et al., "Transendothelial migration of neutrophils involves integrin-associated protein (CD47)," *Proc. Natl. Acad. Sci. USA*, 92:3978-3982 (1995).

Daniel et al., "Pathway of apoptosis induced in Jurkat T Lymphoblasts by anti-HLA Class I antibodies," *Human Immunology*, 65(3):189-199 (2004).

De Leon et al., "High resolution human leukocyte antigen (HLA) class I and class II allele typing in Mexican mestizo women with sporadic breast cancer: case-control study," *BMC Cancer*, 9(48):1-9 (2009).

Degli-Esposti et al., "Cloning and Characterization of TRAIL-R3, a Novel Member of the Emerging TRAIL Receptor Family," *J. Exp. Med.*, 186:1165-1170 (1997).

De Sauvage et al., "Stimulation of Megakaryocytopoiesis and Thrombopoiesis by the c-Mpl Ligand," *Nature*, 369:533-538 (1994).

Desplancq et al., "Multimerization behaviour of single chain Fv variants for the tumour-binding antibody B72.3," *Protein Engineering*, 7(8):1027-1033 (1994).

De St. Groth et al., "Production of Monoclonal Antibodies: Strategy and Tactics," *Journal of Immunological Methods*, 35:1-21 (1980).

Dillman, "Monoclonal antibodies for treating cancer," *Ann. Int. Med.*, 11(7):592-603 (1989).

Dorai et al., "Mammalian cell expression of single-chain Fv (sFv) antibody proteins and their C-terminal fusions with interleukin-2 and other effector domains," *Biotechnology*, 12(9):890-897 (1994).

Dufner et al., "Harnessing phage and ribosome display for antibody optimization," *Trends Biotechnol.*, 24(11):523-529 (2006).

Emery et al., "Osteoprotegerin Is a Receptor for the Cytotoxic Ligand TRAIL," *J. Biol. Chem.*, 273:14363-14367 (1998).

Felgenhauer et al. "Nucleotide Sequences of the cDNAs Encoding the V-Regions of H- and L-Chains of a Human Monoclonal Antibody Specific to HIV-1—gp41," *Nucleic Acids Research*, 18(16):4927 (1990).

Fujimoto et al., "50-kD integrin-associated protein does not detectably influence several functions of glycoprotein IIb-IIIa complex in human platelets," *Blood*, 86(6):2174-2182 (1995).

Fukushima et al., "Enhanced hematopoiesis in vivo and in vitro by splenic stromal cells derived from the mouse with recombinant granulocyte colony-stimulating factor," *Blood*, 80(8):1914-1922 (1992).

Fukushima et al., "Apoptosis of Bone Marrow Cells Via Integrin Associated Protein by the Novel Monoclonal Antibody," *Blood*, 94(10):479A (1999).

Galfre et al., "Preparation of monoclonal antibodies: strategies and procedures," *Methods in Enymology*, 73:3-46 (1981).

Galfre et al., "Rat x rat hybrid myelomas and a monoclonal anti-Fd portion of mouse IgG," *Nature*, 277:131-133 (1979).

Giusti et al., "Somatic diversification of S107 from an antiphosphocholine to an anti-DNA autoantibody is due to a single base change in its heavy chain variable region," *Proc. Natl. Acad. Sci. USA*, 84:2926-2930 (1987).

Goding, "Monoclonal Antibodies: Principles and Practice," *Academic Press*, second Ed., 125:129 (1986).

Granziero et al., "Adoptive immunotherapy prevents prostate cancer in a transgenic animal model," *Eur. J. Immunol.*, 29:1127-1138 (1999).

Greenspan et al., "Defining epitopes: It's not as easy as it seems," *Nature Biotechnology*, 17:936-937 (1999).

Grell et al., "TR60 and TR80 tumor necrosis factor (TNF)-receptors can independently mediate cytolysis," *Lymphokine and Cytokine Research*, 12(3):143-148 (1993).

Griffith et al., "Functional Analysis of TRAIL Receptors Using Monoclonal Antibodies," *J. Immunol.*, 162:2597-2605 (1999).

Güssow and Seemann, "Humanization of Monoclonal Antibodies," *Methods in Enzymology*, 203:99-121 (1991).

Holliger el at., "Specific Killing of Lymphoma Cells by Cytotoxic T-Cells Mediated by a Bispecific Diabody," *Protein Engineering*, 9(3):299-305 (1996).

Hopp et al., "A Short Polypeptide Marker Sequence Useful for Recombinant Protein Identification and Purification," *Biotechnology*, 6:1204-1210 (1988).

Horan et al., "Dimerization of the extracellular domain of granuloycte-colony stimulating factor receptor by ligand binding: a monovalent ligand induces 2:2 complexes," *Biochemistry*, 35:4886-4896 (1996).

Huston et al., "Protein Engineering of Antibody Binding Sites: Recovery of Specific Activity in an Anti-Digoxin Single-Chain Fv Analogue Produced in *Escherichia coli*," *Proc. Natl. Acad. Sci. USA*, 85:5879-5883 (1988).

Ichikawa et al., "Tumoricidal activity of a novel anti-human DR5 monoclonal antibody without hepatocyte cytotoxicity," *Nat. Med.*, 7:954-960 (2001).

Itoh et al., "The Polypeptide Encoded by the cDNA for Human Cell Surface Antigen Fas Can Mediate Apoptosis," *Cell*, 66:233-243 (1991).

Jiang et al., "A Novel Peptide Isolated from a Phage Display Peptide Library with Trastuzumab Can Mimic Antigen Epitope of HER-2," *J. Biol. Chem.*, 280(6):4656-4662 (2005).

Jones et al., "Rapid PCR-Cloning of Full-Length Mouse Immunoglobulin Variable Regions," *Biotechnology*, 9:88-89 (1991).

Kearney, et al., "A New Mouse Myeloma Cell Line That Has Lost immunoglobulin Expression but Permits the Construction of Antibody-Secreting Hybrid Cells Lines," *The Journal of Immunology*, 123(4):1548-1550 (1979).

Keen et al., "The use of serum-free medium for the production of functionally active humanized monoclonal antibody from NSO mouse myeloma cells engineered using glutamine synthetase as a selectable marker," *Cytotechnology*, 18(3):207-217 (Abstract) (1994).

Kipriyanov et al., "Bispecific CD3×CD19 diabody for T cell-mediated lysis of malignant human B cells," *In. J Cancer*, 77:763-772 (1998).

Kohler, et al., "Derivation of specific antibody-producing tissue culture and tumor lines by cell fusion," *Eur. J. Immunol.*, 6:511-519 (1976).

Kortt et al., "Recombinant anti-sialidase single-chain variable fragment antibody: Characterization, formation of dimmer and higher-molecular-mass multimers and the solution of the crystal structure of the single-chain variable fragment/sialidase complex," *Eur. J. Biochem.*, 221:151-157 (1994).

Kortt et al., "Single-chain Fv fragments of anti-neuraminidase antibody NC10 containing five- and ten-residue linkers form dimmers and with zero-residue linker a trimer," *Protein Engineering*, 10(4):423-433 (1997).

Kozak, M., "At Least Six Nucleotides Preceding the AUG Initiator Codon Enhance Translation in Mammalian Cells," *J. Mol. Biol.*, 196:947-950 (1987).

Kumar et al., "Molecular cloning and expression of the fabs of human autoantibodies in *Escherichia coli*," *The Journal of Biological Chemistry*, 275(41):35129-35136 (2000).

Larrick, et al., "Polymerase Chain Reaction Using Mixed Primers: Cloning of Human Monoclonal Antibody Variable Region Genes From Single Hybridoma Cells," *Biotechnology*, 7:934-938 (1989).

Law et al., "Observations on the Effect of a Folic-Acid Antagonist on Transplantable Lymphoid Leukemias in Mice," *Journal of the National Cancer Institute*, 10:179-193 (1949).

Lazar et al., "Transforming growth factor a: mutation of aspartic acid 47 and leucine 48 results in different biological activities," *Molecular and Cellular Biology*, 8:1247-1252 (1988).

Lei et al., "Characterization of the *Erwinia Carotovora pelB* Gene and Its Product Pectate Lyase," *Journal of Bacteriology*, 169:4379-4383 (1987).

Lin et al., "Structure-function relationships in glucagon: properties of highly purified des-His-1-, monoiodo-, and (des-Asn-28, Thr-29)(homoserine lactone-27)-glucagon," *Biochemistry*, 14:1559-1563 (1975).

Lindberg et al., "Molecular Cloning of Integrin-Associated Protein: An Immunoglobulin Family Member with Multiple Membrane-Spanning Domains Implicated in $\beta_v\beta_3$-Dependent Ligand Binding," *The Journal of Cell Biology*, 123(2):485-496, The Rockefeller University Press (1993).

Lindberg et al., "Rh-Related Antigen CD47 is the Signal-Transducer Integrin-Associated Protein," *J. Biol. Chem.*, 269:1567-1570 (1994).

Margulies et al., "Somatic Cell Hybridization of Mouse Myeloma Cells," *Cell*, 8:405-415 (1976).

Mariuzza et al., "The Structural Basis of Antigen-Antibody Recognition," *Ann. Rev. Biophys. Biophys. Chem.*, 16:139-159 (1987).

Marsters et al., "A Novel Receptor for Apo2L/TRAIL Contains a Truncated Death Domain," *Curr. Biol.*, 7:1003-1006 (1997).

Mateo et al., "Induction of Apoptosis in B-Cells From Chronic Lymphocytic Leukemia (B-CLLs) by CD47," *FASEB Journal*, 12(5):A1082 (1998).

Mateo et al., "CD47 ligation induces caspase-independent cell death in chronic lymphocytic leukemia," *Nat. Med.*, 5(11):1277-1284 (1999).

Mawby et al., "Isolation and characterization of CD47 glycoprotein: a multispanning membrane protein which is the same as integrin-associated protein (IAP) and the ovarian tumor marker OA3," *Biochem. J.*, 304:525-530 (1994).
Methia et al., "Oligodeoxynucleotides Antisense to the Proto-Oncogene c-Mpl Specifically Inhibit In Vitro Megakaryocytopoiesis," *Blood*, 82(5):1395-1401 (1993).
Milili et al., "The VDJ Repertoire Expressed in Human preB Cells Reflects the Selection of Bona Fide Heavy Chains," *Eur. J Immunol.*, 26:63-69 (1996).
Mizushima et al., "pEF-BOS, a Powerful Mammalian Expression Vector," *Nucleic Acids Research*, 18(17):5322 (1990).
Moore et al., "Kinetics and thermodynamics of dimer formation and dissociation for a recombinant humanized monoclonal antibody to vascular endothelial growth factor," *Biochemistry*, 38:13960-13967 (1999).
Mori et al., "Human normal hepatocytes are susceptible to apoptosis signal mediated by both TRAIL-R1 and TRAIL-R2," *Cell Death and Differentiation*, 11:203-207 (2004).
Mulligan et al., "Synthesis of Rabbit β-Globin in Cultured Monkey Kidney Cells Following Infection with a SV40 β-Globin Recombinant Genome," *Nature*, 277:108-114 (1979).
Nakayama et al., "Thrombocytosis in preterm infants: a possible involvement of thrombopoietin receptor gene expression," *Journal of Molecular Medicine*, 83:316-320 (2005).
Ngo et al., "Computational Complexity, Protein Structure Prediction, and the Levinthal Paradox ," *The Protein Folding Problem and Tertiary Structure Prediction*, Merz, Jr. et al. Editors, Birkhauser Boston, 433-506 (1994).
O'Brien et al., "Monoclonal antibodies for the human insulin receptor stimulate intrinsic receptor-kinase activity," *Biochim. Soc. Trans.*, 14(6):1021-1023 (1986).
Ohtsuka et al., "Synergistic induction of tumor cell apoptosis by death receptor antibody and chemotherapy agent through JNK/p38 and mitochondrial death pathway," *Oncogene*, 22:2034-2044 (2003).
Pan et al., "An Antagonist Decoy Receptor and a Death Domain-Containing Receptor for TRAIL," *Science*, 277:815-818 (1997).
Pan et al., "The Receptor for the Cytotoxic Ligand TRAIL," *Science*, 276:111-113 (1997).
Paul, *Fundamental Immunology*, Raven Press, NY, Chapter 8, p. 242 (1993).
Paul, *Fundamental Immunology*, 3rd Edition, Raven Press, NY, Chapter 8, pp. 292-295 (1993).
Petterson et al., "CD47 Signals T Cell Death," *J. Immunol.*, 7031-7040 (1999).
Petterson, "CD47 and death signaling in the immune system," *Apoptosis*, 5:299-306 (2000).
Reinhold et al., "In vivo expression of alternatively spliced forms of integrin-associated protein (CD47)," *J. Cell Science*, 108:3419-3425 (1995).
Riechmann et al., "Reshaping Human Antibodies for Therapy," *Nature*, 332:323-327 (1988).
Reiter et al., "Engineering interchain disulfide bonds into conserved framework regions of Fv fragments: improved biochemical characteristics of recombinant immunotoxins containing disulfide-stabilized Fv," *Protein Engineering*, 7(5):697-704 (1994).
Reiter et al., "Stabilization of the Fv Fragments in Recombinant Immunotoxins by Disulfide Bonds Engineered into Conserved Framework Regions," *Biochemistry*, 33:5451-5459 (1994).
Roue et al. "Mitochondrial dysfunction in CD47-mediated caspase-independent cell death: ROS production in the absence of cytochrome c and AIF release," *Biochimie.*, 85:741-746 (2003).
Rozsnyay et al., "Phenylarsine oxide (PAO) blocks antigen receptor-induced calcium response and tyrosine phosphorylation of a distinct group of proteins," *Immunology Lett.*, 37(2-3):197-205 (1993).
Sackstein, "The lymphocyte homing receptors: gatekeepers of the multistep paradigm," *Current Opinion in Hematology*, 12:444-450 (2005).
Sato et al., "Reshaping a Human Antibody to Inhibit the Interleukin 6-Dependent Tumor Cell Growth," *Cancer Research*, 53:851-856 (1993).

Schickel, et al., "Gene for Integrin-Associated Protein (IAP, CD47): Physical Mapping, Genomic Structure, and Expression Studies in Skeletal Muscle," *Biochem. Cell. Biol.*, 80(2):169-176 (2002).
Schwartz et al., "A superactive insulin: [B10-aspartic acid]insulin(human)," *Proc. Natl. Acad. Sci. U.S.A.*, 84:6408-6411 (1987).
Schwartz et al., "A 50-kDa Integrin-associated Protein Is Required for Integrin-regulated Calcium Entry in endothelial Cells," *J. Biol. Chem.*, 268(27):19931-19934 (1993).
Schmidt et al., "A bivalent single-chain antibody-toxin specific for ErbB-2 and the EGF receptor," *Int. J. Cancer*, 65(4):538-546 (1996).
Sheridan et al., "Control of TRAIL-Induced Apoptosis by a Family of Signaling and Decoy Receptors," *Science*, 277:818-821 (1997).
Shigeta et al., "Sperm-immobilizing monoclonal antibody to human seminal plasma antigens," *Clin. Exp. Immunol.*, 42:458-462 (1980).
Shulman et al., "A better cell line for making hybridomas secreting specific antibodies," *Nature*, 276:269-270 (1978).
Smith-Gill et al., "Contributions of immunoglobulin heavy and light chains to antibody specificity for lysozyme and two haptens," *The Journal of Immunology*, 139:4135-4144 (1987).
Song et al., "Light chain of natural antibody plays a dominant role in protein antigen binding," *Biochemical and Biophysical Research Communications*, 268:390-394 (2000).
Souyri, M., "Mpl: from an acute myeloproliferative virus to the isolation of the long sought thrombopoietin," *Seminars in Hematology*, 35(3):222-231 (1998).
Spaargaren et al., "Antibody-induced Dimerization Activates the Epidermal Growth Factor Receptor Tyrosine Kinase," *The J. Biol. Chem.*, 266(3):1733-1739 (1981).
Stancovski et al., "Mechanistic aspects of the opposing effects of monoclonal antibodies to the ERBB2 receptor on tumor growth," *Proc. Natl. Acad. Sci. USA*, 88:8691-8695 (1991).
Trowbridge, I.S., "Interspecies Spleen-Myeloma Hybrid Producing Monoclonal Antibodies Against Mouse Lymphocyte Surface Glycoprotein, T200," *J. Exp. Med.*, 148:313-323 (1978).
Van Geelen et al., "Differential modulation of the TRAIL receptors and the CD95 receptor in colon carcinoma cell lines," *Br. J. Cancer*, 89(2):363-373 (2003).
Verma et al., "Antibody engineering: Comparison of bacterial, yeast, insect and mammalian expression systems," *Journal of Immunological Methods*, 216:165-181 (1998).
Walczak et al., "TRAIL-R2: A Novel Apoptosis-Mediating Receptor for TRAIL," *Embo J.*, 16:5386-5397 (1997).
Wakalee et al., *Ann. Oncol.* On-line publication (Jul. 24, 2009).
Ward et al., "Binding activities of a repertoire of single immunoglobulin variable domains secreted from *Escherichia coli*," *Nature*, 341:544-546 (1989).
Wells, "Perspectives in Biochemistry," *Biochemistry*, 29(37):8509-8517 (1990).
Whitlow et al., "Multivalent Fvs: characterization of single-chain Fv oligomers and preparation of a bispecific Fv," *Protein Eng.*, 7(8):1017-1026 (1994).
Wiley et al., "Identification and Characterization of a New Member of the TNF Family that Induces Apoptosis," *Immunity*, 3:673-682 (1995).
Winkler et al., "Changing the Antigen Binding Specificity by Single Point Mutations of an Anti-p24 (HIV-1) Antibody," *J. Immunol.*, 265:4505-4514 (2000).
Xie et al., "Direct Demonstration of MuSK Involvement in Acetylcholine Receptor Clustering Through Identification of Agonist ScFv," *Nature Biotechnology*, 15(8):768-771 (1997).
Yagita et al., "TRAIL and its receptors as targets for cancer therapy," *Cancer Sci.*, 95:777-783 (2004).
Yanabu et al., "Tyrosine phosphorylation and p72syk activation by an anti-glycoprotein lb monoclonal antibody," *Blood*, 89(5):1590-1598 (1997).
Yarden et al., "Self-phosphorylation of epidermal growth factor receptor: evidence for a model of intermolecular allosteric activation," *Biochemistry*, 26(5):1434-1442 (1987).
Yelton et al., "Fusion of Mouse Myeloma and Spleen Cells," *Current Topics in Microbiology and Immunology*, 81:1-7 (1978).
Japanese Patent Office, International Search Report for App. Ser. No. PCT/JP2003/013063, mailed Nov. 18, 2003, 2 pages.

Japanese Patent Office, International Preliminary Report on Patentability for App. Ser. No. PCT/JP2003/013063, dated Feb. 6, 2004, 4 pages.
European Search Report for App. Ser. No. EP 03 75 1456, dated Apr. 4, 2006, 2 pages.
USPTO Restriction Requirement in U.S. Appl. No. 10/548,727, mailed Apr. 12, 2007, 6 pages.
Fish & Richardson P.C., Reply to Restriction Requirement dated Apr. 12, 2007 in U.S. Appl. No. 10/548,727, filed May 3, 2007, 1 page.
USPTO Non-Final Office Action in U.S. Appl. No. 10/548,727, mailed Aug. 3, 2007, 21 pages.
Fish & Richardson P.C., Reply to Office Action dated Aug. 3, 2007 in U.S. Appl. No. 10/548,727, filed Jan. 15, 2008, 15 pages.
USPTO Final Office Action in U.S. Appl. No. 10/548,727, mailed Apr. 29, 2008, 23 pages.
USPTO Advisory Action in U.S. Appl. No. 10/548,727, mailed Sep. 24, 2008, 6 pages.
USPTO Non-Final Office Action in U.S. Appl. No. 10/548,727, mailed Jan. 28, 2009, 16 pages.
Fish & Richardson P.C., Reply to Office Action dated Jan. 28, 2009 in U.S. Appl. No. 10/548,727, filed Jun. 26, 2009, 9 pages.
USPTO Notice of Allowance in U.S. Appl. No. 10/548,727, mailed Nov. 25, 2009, 29 pages.
Japanese Patent Office, International Search Report for App. Ser. No. PCT/JP2004/003334, mailed Jun. 15, 2004, 3 pages.
Japanese Patent Office, International Preliminary Report on Patentability for App. Ser. No. PCT/JP2004/003334, dated May 2, 2005, 6 pages.
USPTO Restriction Requirement in U.S. Appl. No. 10/550,934, mailed Nov. 21, 2007, 7 pages.
Fish & Richardson P.C., Response to Restriction Requirement dated Nov. 21, 2007 in U.S. Appl. No. 10/550,934, filed Apr. 16, 2008, 2 pages.
USPTO Non-Final Office Action in U.S. Appl. No. 10/550,934, mailed Jun. 12, 2008, 27 pages.
Fish & Richardson P.C., Amendment in Reply to Action dated Jun. 12, 2008 in U.S. Appl. No. 10/550,934, filed Dec. 12, 2008, 45 pages.
USPTO Final Office Action in U.S. Appl. No. 10/550,934, mailed Mar. 16, 2009, 19 pages.
Fish & Richardson P.C., Amendment in Reply to Action dated Mar. 16, 2009 in U.S. Appl. No. 10/550,934, filed Sep. 10, 2009, 75 pages.
Japanese Patent Office, International Search Report for App. Ser. No. PCT/JP2004/004696, mailed Jul. 27, 2004, 5 pages.
Japanese Patent Office, International Preliminary Report on Patentability for App. Ser. No. PCT/JP2004/004696, dated Feb. 9, 2005, 10 pages.
European Search Report for App. Ser. No. EP 04 72 4770, dated Mar. 31, 2006, 4 pages.
USPTO Restriction Requirement in U.S. Appl. No. 10/551,504, mailed Jun. 27, 2008, 6 pages.
Fish & Richardson P.C., Response to Restriction Requirement dated Jun. 27, 2008 in U.S. Appl. No. 10/551,504, filed Sep. 29, 2008, 13 pages.
USPTO Restriction Requirement in U.S. Appl. No. 10/551,504, mailed Dec. 16, 2008, 5 pages.
Fish & Richardson P.C., Response to Restriction Requirement dated Dec. 16, 2008 in U.S. Appl. No. 10/551,504, filed Dec. 23, 2008, 14 pages.
USPTO Non-Final Office Action in U.S. Appl. No. 10/551,504, mailed Apr. 15, 2009, 35 pages.
Fish & Richardson P.C., Amendment in Reply to Action dated Apr. 15, 2009 in U.S. Appl. No. 10/551,504, filed Aug. 14, 2009, 19 pages.
Japanese Patent Office, International Search Report for App. Ser. No. PCT/JP2004/018506, mailed Mar. 22, 2005, 3 pages.
European Search Report for App. Ser. No. EP 04 82 0316, dated Jul. 17, 2008, 3 pages.
Japanese Patent Office, International Search Report for App. Ser. No. PCT/JP2004/018499, mailed Jan. 18, 2005, 2 pages.
Japanese Patent Office, International Preliminary Report on Patentability for App. Ser. No. PCT/JP2004/018499, dated Jan. 26, 2006, 5 pages.
USPTO Restriction Requirement in U.S. Appl. No. 10/582,413, mailed Jan. 4, 2008, 8 pages.
Fish & Richardson P.C., Response to Restriction Requirement dated Jan. 4, 2008 in U.S. Appl. No. 10/582,413, filed Feb. 4, 2008, 2 pages.
USPTO Non-Final Office Action in U.S. Appl. No. 10/582,413, mailed Mar. 31, 2008, 17 pages.
Fish & Richardson P.C., Amendment in Reply to Action dated Mar. 31, 2008 in U.S. Appl. No. 10/582,413, filed Jun. 30, 2008, 20 pages.
USPTO Interview Summary in U.S. Appl. No. 10/582,413, mailed Jun. 30, 2008, 2 pages.
USPTO Notice of Informal or Non-Responsive Amendment in U.S. Appl. No. 10/582,413, mailed Oct. 20, 2008, 3 pages.
USPTO Interview Summary in U.S. Appl. No. 10/582,413, mailed Nov. 12, 2008, 4 pages.
Fish & Richardson P.C., Amendment in Reply to Notice of Informal or Non-Responsive Amendment dated Oct. 20, 2008 in U.S. Appl. No. 10/582,413, filed Nov. 17, 2008, 10 pages.
USPTO Interview Summary in U.S. Appl. No. 10/582,413, mailed Nov. 25, 2008, 4 pages.
USPTO Interview Summary in U.S. Appl. No. 10/582,413, mailed Dec. 24, 2008, 4 pages.
USPTO Restriction Requirement in U.S. Appl. No. 10/582,413, mailed Mar. 11, 2009, 8 pages.
Fish & Richardson P.C., Response to Restriction Requirement dated Mar. 11, 2009 in U.S. Appl. No. 10/582,413, filed Apr. 8, 2009, 8 pages.
USPTO Final Office Action in U.S. Appl. No. 10/582,413, mailed Jun. 25, 2009, 28 pages.
USPTO Interview Summary in U.S. Appl. No. 10/582,413, mailed Oct. 27, 2009, 4 pages.
Japanese Patent Office, International Search Report for App. Ser. No. PCT/JP2004/018493, mailed Mar. 22, 2005, 2 pages.
Japanese Patent Office, International Preliminary Report on Patentability for App. Ser. No. PCT/JP2004/018493, dated Dec. 20, 2005, 7 pages.
European Search Report for App. Ser. No. EP 04 82 0305, dated Oct. 6, 2008, 3 pages.
USPTO Restriction Requirement in U.S. Appl. No. 10/582,304, mailed Nov. 20, 2008, 7 pages.
Fish & Richardson P.C., Response to Restriction Requirement dated Nov. 20, 2008 in U.S. Appl. No. 10/582,304, filed Dec. 16, 2008, 3 pages.
USPTO Non-Final Office Action in U.S. Appl. No. 10/582,304, mailed Apr. 1, 2009, 38 pages.
Fish & Richardson P.C., Amendment in Reply to Office Action dated Apr. 1, 2009 in U.S. Appl. No. 10/582,304, filed Jun. 30, 2009, 15 pages.
USPTO Non-Final Office Action in U.S. Appl. No. 10/582,304, mailed Sep. 15, 2009, 22 pages.
Japanese Patent Office, International Search Report for App. Ser. No. PCT/JP2004/018501, mailed Mar. 29, 2005, 2 pages.
International Preliminary Report on Patentability for App. Ser. No. PCT/JP2004/018501, dated Nov. 4, 2005, 7 pages.
European Search Report for App. Ser. No. EP 04 82 0311, dated Jan. 28, 2009, 4 pages.
Japanese Patent Office, International Search Report for App. Ser. No. PCT/JP2004/005152, mailed Jul. 20, 2004, 2 pages.
Japanese Patent Office, International Preliminary Report on Patentability for App. Ser. No. PCT/JP2004/005152, dated Feb. 14, 2005, 6 pages.
European Search Report for App. Ser. No. EP 04 72 6750, dated Feb. 4, 2008, 3 pages.
USPTO Non-Final Office Action in U.S. Appl. No. 11/547,747, mailed Jun. 1, 2009, 41 pages.
Fish & Richardson P.C., Amendment in Reply to Office Action dated Jun. 1, 2009 in U.S. Appl. No. 11/547,747, filed Nov. 30, 2009, 12 pages.
USPTO Restriction Requirement in U.S. Appl. No. 11/913,229, mailed Jul. 8, 2009, 6 pages.
Fish & Richardson P.C., Response to Restriction Requirement dated Jul. 8, 2009 in U.S. Appl. No. 11/913,229, filed Aug. 4, 2009, 1 page.
Japanese Patent Office, International Search Report for App. Ser. No. PCT/JP2006/309890, mailed Jul. 18, 2006, 2 pages.
International Preliminary Report on Patentability for App. Ser. No. PCT/JP2006/309890, dated Nov. 19, 2007, 5 pages.

European Search Report for App. Ser. No. EP 06 74 6578, dated Jun. 25, 2009, 2 pages.
Japanese Patent Office, International Search Report for App. Ser. No. PCT/JP2007/063946, mailed Aug. 14, 2007, 7 pages.
International Preliminary Report on Patentability for App. Ser. No. PCT/JP2007/063946, dated Jan. 20, 2009, 10 pages.
USPTO Restriction Requirement in U.S. Appl. No. 10/582,654, mailed May 26, 2009, 9 pages.
Klarquist Sparkman, LLP Response to Restriction Requirement dated May 26, 2009 in U.S. Appl. No. 10/582,654, filed Jun. 23, 2009, 2 pages.
USPTO Office Action in U.S. Appl. No. 10/582,654, mailed Sep. 1, 2009, 36 pages.
USPTO Restriction Requirement in U.S. Appl. No. 10/399,518, mailed Nov. 25, 2005, 9 pages.
Foley & Lardner LLP, Response to Restriction Requirement dated Nov. 25, 2005 in U.S. Appl. No. 10/399,518, filed Dec. 23, 2005, 3 pages.
USPTO Non-Final Office Action in U.S. Appl. No. 10/399,518, mailed Mar. 27, 2006, 38 pages.
Foley & Lardner LLP, Amendment in Reply to Action dated Mar. 27, 2006 in U.S. Appl. No. 10/399,518, filed Sep. 26, 2006, 26 pages.
Foley & Lardner LLP, Supplemental Amendment in Reply to Action dated Mar. 27, 2006 in U.S. Appl. No. 10/399,518, filed Oct. 11, 2006, 11 pages.
Foley & Lardner LLP, Supplemental Amendment in Reply to Action dated Mar. 27, 2006 in U.S. Appl. No. 10/399,518, filed Oct. 13, 2006, 11 pages.
USPTO Non-Final Office Action in U.S. Appl. No. 10/399,518, mailed Dec. 28, 2006, 29 pages.
Foley & Lardner LLP, Amendment in Reply to Action dated Dec. 28, 2006 in U.S. Appl. No. 10/399,518, filed May 3, 2007, 22 pages.
USPTO Final Office Action in U.S. Appl. No. 10/399,518, mailed Jun. 7, 2007, 13 pages.
Foley & Lardner LLP, Amendment in Reply to Action dated Jun. 7, 2007 in U.S. Appl. No. 10/399,518, filed Sep. 7, 2007, 9 pages.
Advisory Action in U.S. Appl. No. 10/399,518, mailed Sep. 27, 2007, 5 pages.
Interview Summary in U.S. Appl. No. 10/399,518, mailed Nov. 13, 2007, 3 pages.
USPTO Non-Final Office Action in U.S. Appl. No. 10/399,518, mailed Jan. 31, 2008, 14 pages.
Foley & Lardner LLP, Amendment in Reply to Action dated Jan. 31, 2008 in U.S. Appl. No. 10/399,518, filed Apr. 30, 2008, 7 pages.
USPTO Final Office Action in U.S. Appl. No. 10/399,518, mailed Aug. 4, 2008, 8 pages.
Advisory Action in U.S. Appl. No. 10/399,518, mailed Nov. 7, 2008, 4 pages.
Foley & Lardner LLP, Amendment in Reply to Action dated Nov. 7, 2008 in U.S. Appl. No. 10/399,518, filed Oct. 23, 2008, 8 pages.
USPTO Non-Final Office Action in U.S. Appl. No. 10/399,518, mailed Feb. 17, 2009, 12 pages.
Foley & Lardner LLP, Amendment in Reply to Action dated Feb. 17, 2009 in U.S. Appl. No. 10/399,518, filed May 18, 2009, 26 pages.
USPTO Final Office Action in U.S. Appl. No. 10/399,518, mailed Sep. 11, 2009, 24 pages.
USPTO Restriction Requirement in U.S. Appl. No. 10/257,864, mailed Feb. 1, 2006, 14 pages.
USPTO Restriction Requirement in U.S. Appl. No. 10/582,176, mailed Oct. 19, 2009, 6 pages.
Fish & Richardson P.C., Response to Restriction Requirement dated Oct. 19, 2009 in U.S. Appl. No. 10/582,176, filed Nov. 4, 2009, 1 page.
USPTO Non-Final Office Action in U.S. Appl. No. 11/913,229, mailed Nov. 3, 2009, 40 pages.
Fisk et al., "Increased sensitivity of Adriamycin-selected Tumor Lines to CTL-mediated Lysis Results in Enhanced Drug Sensitivity," Cancer Res., 58:4790-4793 (1998).
Jalili et al., "Multi-Drug Resistant Leukemic Cells Highly Express HLA Class I Molecules and Single-Chain Fv Diabody Specific to HLA-A Overcomes Drug Resistance in These Cells," Blood (ASH Annual Meeting Abstracts), 118 (11):701a-702a (#2376) (2007).

Melguizo et al., "Modulation of HLA class I expression in multidrug-resistant human rhabdomyosarcoma cells," Neoplasma, 50(2):91-96 (2003).
Ozaki et al., "Induction of myeloma cell death by a recombinant HLA class I-specific single-chain Fv diabody," Dai 65 Nihon Ketsueki Gakkai, Dai 45 kai Nihon Ketsueki Gakkai Sokai, Osaka (Aug. 28-31, 2003).
Ozaki et al., "A recombinant HLA class I-specific single chain Fv diabody induces cell death in human lymphoid malignancies," 45th Annual Meeting of the American Society of Hematology, San Diego, CA, USA (Dec. 6-9, 2003).
Prados et al., "Induction of drug resistance in embryonal rhabdomyosarcoma treated with conventional chemotherapy is associated with HLA class I increase," Neoplasma, 53(3):226-231 (2006).
Sekimoto et al., "Eradication of human myeloma cells by a recombinant HLA class I-specific single chain Fv diabody," 45th Annual Meeting of the American Society of Hematology, San Diego, CA, USA (Dec. 6-9, 2003).
Sonneveld, "Multidrug resistance in haematological malignancies," J. Intern. Med., 247:521-534 (2000).
Tsukakoshi, New Pharmacology, 3rd revised edition, Nankodo Co., Ltd., 557-568 (1997).
Japanese Patent Office, International Search Report for App. Ser. No. PCT/JP2008/054443, dated May 27, 2008, 7 pages.
USPTO Non-Final Office Action in U.S. Appl. No. 10/582,176, mailed Jan. 25, 2010, 7 pages.
USPTO Non-Final Office Action in U.S. Appl. No. 10/582,304, mailed Mar. 24, 2010, 10 pages.
Fish & Richardson P.C., Amendment in Reply to Action dated Nov. 3, 2009 in U.S. Appl. No. 11/913,229, filed Apr. 7, 2010, 15 pages.
Foley & Lardner LLP, Amendment in Reply to Action dated Sep. 11, 2009 in U.S. Appl. No. 10/399,518, filed Dec. 11, 2009, 9 pages.
USPTO Non-Final Office Action in U.S. Appl. No. 10/399,518, mailed Mar. 23, 2010, 19 pages.
USPTO Non-Final Office Action in U.S. Appl. No. 10/550,934, mailed Dec. 8, 2009, 33 pages.
USPTO Interview Summary in U.S. Appl. No. 10/582,413, mailed Dec. 2, 2009, 4 pages.
EMBL Accession No. U27005, dated Aug. 31, 1995, 1 page.
EMBL Accession No. AY081858, dated Jan. 2, 2003, 1 page.
Pettersen et al., "Role of the TCR Binding Region of the HLA Class I alpha2 Domain in Regulation of Cell Adhesion and Proliferation," J. Immunol., 156:1415-1424 (1996).
Retter et al., Both Sm and DNA are Selecting Antigens in the Anti-Sm B Cell Response in Autoimmune MRL/lpr Mice, J. Immunol., 156:1296-1306 (1996).
Sekine et al., Enrichment of Anti-Glomerular Antigen Antibody-Producing Cells in the Kidneys of MRL/MpJ-Fas(lpr) Mice, J. Immunol., 172:3913-3921 (2004).
European Search Report for App. Ser. No. EP 07 79 0727, dated Nov. 13, 2009, 5 pages.
USPTO Final Office Action in U.S. Appl. No. 11/547,747, mailed Feb. 19, 2010, 15 pages.
Abe et al., "Surrogate thrombopoietin," Immunology Letters, 61:73-78 (1998).
Boger et al., "Cytokine receptor dimerization and activation: prospects for small molecule agonists," Bioorganic and Medicinal Chemistry, 9(3):557-562 (2001).
Burrone et al., "Stimulation of HLA-A,B,C by IFN-alpha. The derivation of Molt 4 variants and the differential expression of HLA-A,B,C subsets," The EMBO Journal, 4(11):2855-2860 (1985).
Cangemi et al., "IFN-alpha mediates the up-regulation of HLA class I on melanoma cells without switching proteasome to immunoproteasome," International Immunology, 15(12):1415-1421 (2005).
CAPLUS Accession No. 2005:547624, 2 pages (2008).
Caron et al., "Engineered Humanized Dimeric Forms of IgG Are More Effective Antibodies," J. Exp. Med., 176:1191-1195 (1992).
DeJonge et al., "In vivo retargeting of T cell effector function by recombinant bispecific single chain Fv (anti-DC3 x anti-idiotype) induces long term survival of the murine BCL1 lymphoma model," J. Immunol., 161(3):1454-1461 (1998).

Kong et al., "A Single Residue, Aspartic Acid 95, in the δ Opioid Receptor Specifies Selective High Affinity Agonist Binding," *The Journal of Biological Chemistry*, 268(31):23056-23058 (1993).

Kriangkum et al., "Bispecific and bifunctional single chain recombinant antibodies," *Biomol. Eng.*, 18(2):31-40 (2001).

Kumar et al., "The second PDZ domain of INAD is a type I domain involved in binding to eye protein kinase C. Mutational analysis and naturally occurring variants," *J. Biol. Chem.*, 276(27):24971-2497 (2001).

Mack et al., "A small bispecific antibody construct expressed as a functional single-chain molecule with high tumor cell cytotoxicity," *Proc. Natl. Acad. Sci. USA*, 92(15):7021-7025 (1995).

Mallender et al., "Construction, expression and activity of a bivalent bispecific single-chain antibody," *J. Biol. Chem.*, 269(1):199-206 (1994).

McInnes and Schett, "Cytokines in the pathogenesis of rheumatoid arthritis," *Nature Reviews/Immunology*, 7:429-442 (2007).

Medline Plus Drug Information: Dexamethasone Oral. Retrieved from the Internet: www.nlm.nih.gov/medlineplus/druginfo/meddmaster/a682792.html, retrieved Jul. 19, 2007; last revised Apr. 1, 2003 (see p. 3) (4 pages).

Milligan, "G Protein-Coupled Receptor Dimerization: Function and Ligand Pharmacology," *Mol. Pharm.*, 66:1-7 (2004).

Palacios et al., "IL-3-dependent mouse clones that express B-220 surface antigen, contain Ig genes in germ-line configuration, and generate B lymphocutes in vivo," *Cell*, 41:272-734 (1985).

Sal-man et al., "Arginine mutations within a transmembrane domain of Tar, an *Escherichia coli* aspartate receptor, can drive monodimer dissociation and heterodimer association n vivo," *Biochem. J.*, 385(1):29-36 (2005).

Scott, "The Problem with Potency," *Nature Biotechnology*, 23(9):1037-1039 (2005).

Seikomoto et al., "A Single-Chain Fv Diabody Against Human Leukocyte Antigen-A Molecules Specifically Induces Myeloma Cell Death in the Bone Marrow Environment," *Cancer Res.*, 67(3):1184-1192 (2007).

Sekimoto et al., "Eradication of Human Myeloma Cells by a Recombinant HLA Class I-Specific Single Chain Fv Diabody," *Blood*, 102:932a, XP009106629 (Abstract #3469) (Nov. 2003) [Abstract of the American Society of Hematology 45$^{th}$ Annual Meeting, Dec. 6-9, 2003, San Diego, California].

Sekimoto et al., "A Recombinant HLA Class I-Specific Single Chain Fv Diabody Induces Cell Death in Human Lymphoid Malignancies," *Blood*, 102:933a, XP002987122 (Abstract #3474) (Nov. 2003) [Abstract of the American Society of Hematology 45th Annual Meeting, Dec. 6-9, 2003, San Diego, California].

Souyri et al., "A putative truncated cytokine receptor gene transduced by the myeloproliferative leukemia virus immortalizes hematopoietic progenitors," *Cell*, 63:1137-1147 (1990).

Stein et al., "Characterization of humanized IgG4 anti-HLA-DR monoclonal antibody that lacks effector cell functions but retains direct antilymphoma activity and increases the potency of rituximab," *Blood*, 108(8):2736-2744 (2006).

Brooke et al., "Human lymphocytes interact directly with CD47 through a novel member of the signal regulatory protein (SIRP) family," *J. Immunol.*, 173:2562-2570 (2004).

Vernon-Wilson et al., "CD47 is a ligand for rat macrophage membrane signal regulatory protein SIRP (OX41) and human SIRPalpha 1," Eur. J. Immunol., 30:2130-2137 (2000).

USPTO Notice of Allowance in U.S. Appl. No. 10/551,504, mailed May 26, 2010, 7 pages.

International Preliminary Report on Patentability for App. Ser. No. PCT/JP2004/018506, mailed Sep. 14, 2006, 9 pages.

USPTO Non-Final Office Action in U.S. Appl. No. 10/582,413, mailed Apr. 16, 2010, 27 pages.

Fish & Richardson P.C., Amendment in Reply to Action dated Feb. 19, 2010 in U.S. Appl. No. 11/547,747, filed Jun. 18, 2010, 13 pages.

USPTO Final Office Action in U.S. Appl. No. 11/913,229, mailed Jun. 10, 2010, 10 pages.

Fish & Richardson P.C., Amendment in Reply to Action dated Jan. 25, 2010 in U.S. Appl. No. 10/582,176, filed Jul. 23, 2010, 11 pages.

Fish & Richardson P.C., Amendment in Reply to Office Action dated Mar. 24, 2010 in U.S. Appl. No. 10/582,304, filed Jul. 26, 2010, 14 pages.

USPTO Non-Final Office Action in U.S. Appl. No. 10/582,304, mailed Oct. 14, 2010, 7 pages.

Fish & Richardson P.C., Amendment in Reply to Action dated Apr. 16, 2010 in U.S. Appl. No. 10/582,413, filed Oct. 15, 2010, 11 pages.

Klarquist Sparkman, LLP Amendment in Reply to Action dated Sep. 1, 2009 in U.S. Appl. No. 10/582,654, filed Feb. 26, 2010, 11 pages.

USPTO Final Office Action in U.S. Appl. No. 10/582,654, mailed Apr. 6, 2010, 15 pages.

Klarquist Sparkman, LLP Amendment in Reply to Action dated Apr. 6, 2010 in U.S. Appl. No. 10/582,654, filed Sep. 21, 2010, 7 pages.

Kikuchi et al., "A bivalent single-chain Fv fragment against CD47 induces apoptosis for leukemic cells," *Biochem. Biophys. Res. Commun.*, 315:912-918 (2004).

Piétri-Rouxel et al., "The biochemical effect of the naturally occurring Trp64→ Arg mutation on human β3-adrenoceptor activity," *Eur. J. Biochem.*, 247:1174-1179, 1997.

Carpenter et al., "Rational design of stable lyophilized protein formulations: some practical advice," *Pharmaceutical Research*, 14(8):969-975 (1997).

Carpenter et al., "Rational design of stable lyophilized protein formulations: theory and practice," *Pharma Biotechnol.*, 13:109-133 (2001).

Chowdhury et al., "Engineering scFvs for improved stability," *Methods Mol. Biol.*, 207:237-54 (2003).

Cleland et al., "A specific molar ratio of stabilizer to protein is required for storage stability of a lyophilized monoclonal antibody," *Journal of Pharmaceutical Sciences*, 90(3):310-321 (2001).

Creighton, T., "Protein folding," *Biochem. J.*, 270(1):1-16 (1990).

Frokjaer et al., "Protein drug stability: a formulation challenge," *Nature Rev Drug Discov.*, 4:298-306 (2005).

Garcia-Gonzalez et al., "Purification of murine IgG3 and IgM monoclonal antibodies by euglobulin precipitation," *Journal of Immunological Methods*, 111:17-23 (1988).

GenBank: U27005.1, *Mus musculus*, isolate 7183Liv, Vh7183 Ig heavy chain variable region gene, Vh region, partial cds, 1 page (Apr. 1996).

GenBank: AY081858.1, *Mus musculus*, isolate H3-9 anti-GBM immunoglobulin kappa chain variable region mRNA, partial cds, 1 page (Mar. 2004).

Gombotz et al., "The stabilization of a human IgM monoclonal antibody with poly(vinylpyrrolidone)," *Pharmaceutical Research*, 11(5):624-632 (1994).

Jung et al., "The importance of framework residues H6, H7 and H10 in antibody heavy chains: experimental evidence for a new structural subclassification of antibody V(H) domains," *J. Mol. Biol.*, 309(3):701-16 (2001).

Kontermann, R., "Recombinant bispecific antibodies for cancer therapy," *Acta Pharmacol. Sin.*, 26(1):1-9 (2005).

Le Gall et al., "Effect of linker sequences between the antibody variable domains on the formation, stability and biological activity of a bispecific tandem diabody," *Protein Engineering Design & Selection*, 17(4):357-366 (2004).

Lee et al., "Reversible dimer formation and stability of the antitumour single chain Fv antibody MFE-23 by neutron scattering, analytical ultracentrifugation, and NMR and FR-IR spectroscopy," *J. Mol. Biol.*, 320:107-127 (2002).

Loffler, "A recombinant bispecific single-chain antibody, CD19 x CD3, induces rapid and high lymphoma-directed cytotoxicity by unstimulated T lymphocytes," *Blood*, 95(6):2098-2103 (2000).

Martsev et al., "Antiferritin single-chain antibody: a functional protein with incomplete folding?" *FEBS Letters*, 441:458-462 (1998).

Sharma et al., "Study of IgM aggregation in serum of patients with macroglobulinemia," *Clin Chem Lab Med*, 38(8):759-764 (2000).

Wang et al., "Instability, stabilization, and formulation of liquid protein pharmaceuticals," *International Journal of Pharmaceutics*, 185:129-188 (1999).

Wang et al., "Lyophilization and development of solid protein pharmaceuticals," *International Journal of Pharmaceutics*, 203:1-60 (2000).

Wang et al., "Protein aggregation and its inhibition in biopharmaceutics," *International Journal of Pharmaceutics*, 289:1-30 (2005).

USPTO Final Office Action in U.S. Appl. No. 10/582,176, mailed Oct. 29, 2010, 11 pages.

Fish & Richardson P.C., Amendment in Reply to Action dated Oct. 29, 2010 in U.S. Appl. No. 10/582,176, filed Apr. 28, 2011, 10 pages.

USPTO Final Office Action in U.S. Appl. No. 10/582,413, mailed Dec. 23, 2010, 12 pages.

USPTO Non-Final Office Action in U.S. Appl. No. 10/582,304, mailed Dec. 9, 2010, 12 pages.

USPTO Restriction Requirement in U.S. Appl. No. 11/910,117, mailed May 3, 2010, 9 pages.

Fish & Richardson P.C., Amendment and Response to Restriction Requirement mailed May 3, 2010 in U.S. Appl. No. 11/910,117, filed Nov. 2, 2010, 11 pages.

USPTO Non-Final Office Action in U.S. Appl. No. 11/910,117, mailed Jan. 24, 2011, 10 pages.

International Search Report for App. Ser. No. PCT/JP2006/306800, mailed May 16, 2006, 4 pages.

International Preliminary Report on Patentability for App. Ser. No. PCT/JP2006/306800, dated Oct. 3, 2007, 6 pages.

European Search Report for App. Ser. No. EP 06 73 0748, dated Apr. 22, 2009, 7 pages.

International Search Report for App. Ser. No. PCT/JP2006/311625, mailed Aug. 22, 2006, 2 pages.

International Preliminary Report on Patentability for App. Ser. No. PCT/JP2006/311625, dated Dec. 11, 2007, 4 pages.

USPTO Restriction Requirement in U.S. Appl. No. 11/916,981, mailed Mar. 31, 2010, 5 pages.

Fish & Richardson P.C. Response to Restriction Requirement dated Mar. 31, 2010 and Preliminary Amendment in U.S. Appl. No. 11/916,981, filed Sep. 29, 2010, 6 pages.

USPTO Non-Final Office Action in U.S. Appl. No. 11/916,981, mailed Dec. 3, 2010, 8 pages.

Fish & Richardson P.C., Amendment and Response to Restriction Requirement dated Jul. 1, 2010 in U.S. Appl. No. 11/916,979, filed Nov. 30, 2010, 9 pages.

USPTO Non-Final Office Action in U.S. Appl. No. 11/916,979, mailed Jan. 21, 2011, 15 pages.

USPTO Restriction Requirement in U.S. Appl. No. 11/916,351, mailed Sep. 3, 2010, 8 pages.

Fish & Richardson P.C., Amendment and Response to Restriction Requirement dated Sep. 3, 2010 in U.S. Appl. No. 11/916,351, filed Dec. 2, 2010, 9 pages.

USPTO Non-Final Office Action in U.S. Appl. No. 11/916,351, mailed Mar. 3, 2011, 11 pages.

USPTO Restriction Requirement in U.S. Appl. No. 12/530,670, mailed Mar. 21, 2011, 7 pages.

Fish & Richardson P.C., Amendment in Reply to Action dated Dec. 9, 2010 in U.S. Appl. No. 10/582,304, filed May 27, 2011, 5 pages.

USPTO Restriction Requirement in U.S. Appl. No. 11/910,117, mailed May 3, 2010, 9 pages.

Fish & Richardson P.C., Amendment and Response to Restriction Requirement mailed May 3, 2010 in U.S. Appl. No. 11/910,117, filed Nov. 2, 2010, 11 pages.

USPTO Non-Final Office Action in U.S. Appl. No. 11/910,117, mailed Jan. 24, 2011, 10 pages.

Fish & Richardson P.C., Amendment in Reply to Action dated Jan. 24, 2011 in U.S. Appl. No. 11/910,117, filed Jun. 23, 2011, 20 pages.

Fish & Richardson P.C. Amendment in Reply to Final Office Action dated Jun. 10, 2010 in U.S. Appl. No. 11/913,229, filed Jul. 7, 2011, 24 pages.

USPTO Restriction Requirement in U.S. Appl. No. 11/916,979, mailed Jul. 1, 2010, 7 pages.

Fish & Richardson P.C., Amendment and Response to Restriction Requirement dated Jul. 1, 2010 in U.S. Appl. No. 11/916,979, filed Nov. 30, 2010, 9 pages.

USPTO Non-Final Office Action in U.S. Appl. No. 11/916,979, mailed Jan. 21, 2011, 15 pages.

Fish & Richardson P.C., Amendment in Reply to Action dated Jan. 21, 2011 in U.S. Appl. No. 11/916,979, filed Jul. 14, 2011, 20 pages.

USPTO Final Office Action in U.S. Appl. No. 11/916,351, mailed Oct. 28, 2011, 10 pages.

Ausubel et al., Short Protocols in Molecular Biology, 3rd Edition, 1985, p. A1-44.

Holliger et al., "Engineered antibody fragments and the rise of single domains," *Nat. Biotechnol.*, 23:1126-1136 (2005).

Humes et al., "Direct toxic effect of the radiocontrast agent diatrizoate on renal proximal tubule cells," *Am. J. Physiol.*, 252(2):F246-F255 (1987).

Lower, Chemical Equilibrium, A Chem1 Reference Text, 2001, pp. 1-28.

Olafsen et al., "Antibody vectors for imaging," *Semin. Nucl. Med.*, 40:167-181 (2010).

von Mehren et al., "Monoclonal antibody therapy for cancer," *Annu. Rev. Med.*, 54:343-369 (2003).

USPTO Non-Final Office Action in U.S. Appl. No. 10/582,304, mailed Aug. 15, 2011, 10 pages.

USPTO Final Office Action in U.S. Appl. No. 11/910,117, mailed Sep. 9, 2011, 12 pages.

USPTO Non-Final Office Action in U.S. Appl. No. 11/913,229, mailed Aug. 22, 2011, 27 pages.

Fish & Richardson P.C., Amendment in Reply to Action dated Dec. 3, 2010 in U.S. Appl. No. 11/916,981, filed Jun. 2, 2011, 18 pages.

USPTO Final Office Action in U.S. Appl. No. 11/916,981, mailed Sep. 12, 2011, 10 pages.

USPTO Final Office Action in U.S. Appl. No. 11/916,979, mailed Sep. 16, 2011, 20 pages.

Fish & Richardson P.C., Amendment in Reply to Action dated Mar. 3, 2011 in U.S. Appl. No. 11/916,351, filed Aug. 2, 2011, 16 pages.

Fish & Richardson P.C., Response to Restriction Requirement mailed Mar. 21, 2011 in U.S. Appl. No. 12/530,670, filed Aug. 10, 2011, 2 pages.

Buskens et al., "Adenocarcinomas of the Gastro-Esophageal Junction: A Comparative Study of the Gastric Cardia and the Esophagus with Respect to Cyclooxygenase-2 Expression," *Digestive Disease Week Abstracts and Itinerary Planner*, Abstract No. 850 (2003).

Carter et al., "Chemotherapy of Cancer," $2^{nd}$ Edition, John Wiley & Sons: New York, Appendix C (1981).

Gura, "Systems for Identifying New Drugs Are Often Faulty," *Science*, 278:1041-1042 (1997).

Kaiser, "First Pass at Cancer Genome Reveals Complex Landscape," *Science*, 313:1370 (2006).

Krontiris and Capizzi, "Molecular and Cellular Biology of Cancer," Internal Medicine, $4^{th}$ Edition, Editor-in-chief Jay Stein, Elsevier Science, Chapters 71-72, pp. 699-729 (1994).

Taber's Cyclopedic Medical Dictionary, F.A. Davis Company, Philadelphia, p. 274 (1985).

USPTO Non-Final Office Action in U.S. Appl. No. 12/530,670, mailed Oct. 19, 2011, 23 pages.

USPTO Restriction Requirement in U.S. Appl. No. 12/307,042, mailed Dec. 6, 2011, 9 pages.

* cited by examiner

FIG. 1

```
5'-AATTCCCAGCACAGTGGTAGATAAGTAAG(SEQ ID NO:7)
       GGGTCGTGTCACCATCTATTCATTCAGCT-5'(SEQ ID NO:8)
```

FIG. 8
2D7(-) ANTI-MOUSE IgG (-)    2D7(-) ANTI-MOUSE IgG (+)
2D7(+) ANTI-MOUSE IgG (-)    2D7(+) ANTI-MOUSE IgG (+)
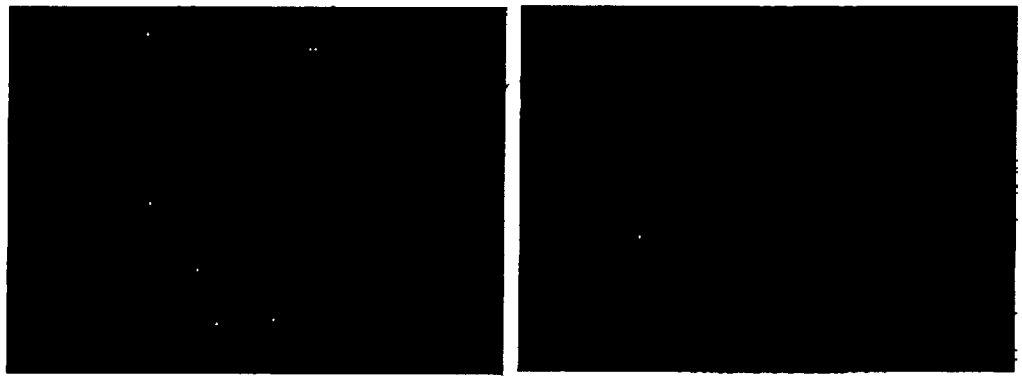

FIG. 9

```
         10         20         30         40         50         60         70         80         90        100
CCTgaattccaCCATGGAGCTGGGATCTTTCTCTTCCTCCTGTCAATAACTGCAGGTGTCCATTGCCAGGTCCAGTTGCCAGTGCAGCTGACTGAG
            M  R  W  S  W  I  F  L  F  L  L  S  I  T  A  G  V  H  C  Q  V  Q  L  Q  Q  S  G  P  E
                      HEAVY-CHAIN LEADER SEQUENCE 110        120        130        140        150        160        170        180        190        200
CTGGTGAAGCCTGGGGCTTCAGTGAAGATGTCTTGTAAGGCTTCTGGCTACACCTTCACAGACTACTTTATACACTGGGTGAAACAGAGGCCTGGACAGG
 L  V  K  P  G  A  S  V  K  M  S  C  K  A  S  G  Y  T  F  T  D  Y  F  I  H  W  V  K  Q  R  P  G  Q 210        220        230        240        250        260        270        280        290        300
GACTTGAATGGATTGGATGGATTTTTCCTGGAGATGATACTACTGATTACAATGAGAAGTTCAGGGGCAAGACCACACTGACTGCAGACAAATCCTCCAG
 L  E  W  I  G  W  I  F  P  G  D  D  T  T  D  Y  N  E  K  F  R  G  K  T  T  L  T  A  D  K  S  S  S
                                 HEAVY-CHAIN VARIABLE REGION 310        320        330        340        350        360        370        380        390        400
CACAGCCTACATTTTGCTCAGCAGCCTGACCTCTGAGGACTCTGCGATGTATTTCTGTGTAAGGAGTGACGACTTTGACTACTGGGGCCAGGGCACCACT
 T  A  Y  I  L  L  S  S  L  T  S  E  D  S  A  M  Y  F  C  V  R  S  D  D  F  D  Y  W  G  Q  G  T  T 410        420        430        440        450        460        470        480        490        500
CTCACAGTCTCCTCAggtggaggcggttcaggcggaggtggcCAAATTGTTCTCACCCAGTCGCCAGCAATCATGTCTGCATCTCCAGGGGAGAAGGTCACCATAACCTGCA
 L  T  V  S  S  G  G  G  G  S  G  G  G  G  S  Q  I  V  L  T  Q  S  P  A  I  M  S  A  S  P  G  E  K  V  T  I  T  C 510        520        530        540        550        560        570        580        590        600
GTGCCAGCTCAAGTGTAAGTTACATGCACTGGTTCCAGCAGAAGCCAGGCACTTCTCCCAAACTCTGGATTTATAGCACATCCAACCTGGCTTCTGGAGT
 S  A  S  S  S  V  S  Y  M  H  W  F  Q  Q  K  P  G  T  F  P  K  L  W  I  Y  S  T  S  N  L  A  S  G  V
                                       LIGHT-CHAIN VARIABLE REGION 610        620        630        640        650        660        670        680        690        700
CCCTACTCGCTTCAGTGGCAGTGGATCTGGGACCTCTTACTCTCTCACAATCAGCCGAATGGAGGCTGAAGATGCTGCCACTTATTACTGCCAGCAAAGG
 P  T  R  F  S  G  S  G  S  G  T  S  Y  S  L  T  I  S  R  M  E  A  E  D  A  A  T  Y  Y  C  Q  Q  R 710        720        730        740        750        760        770        780        790
ACGAGTTATCCACCCACGTTCGGCTCGGGGACAAAGTTGGAGATAAAAgactacaaggatgacgacgataagtgataagcggccgcaat
 T  S  Y  P  P  T  F  G  S  G  T  K  L  E  I  K  D  Y  K  D  D  D  D  K
                                                     FLAG-TAG
```

FIG. 15A
FIG. 15B
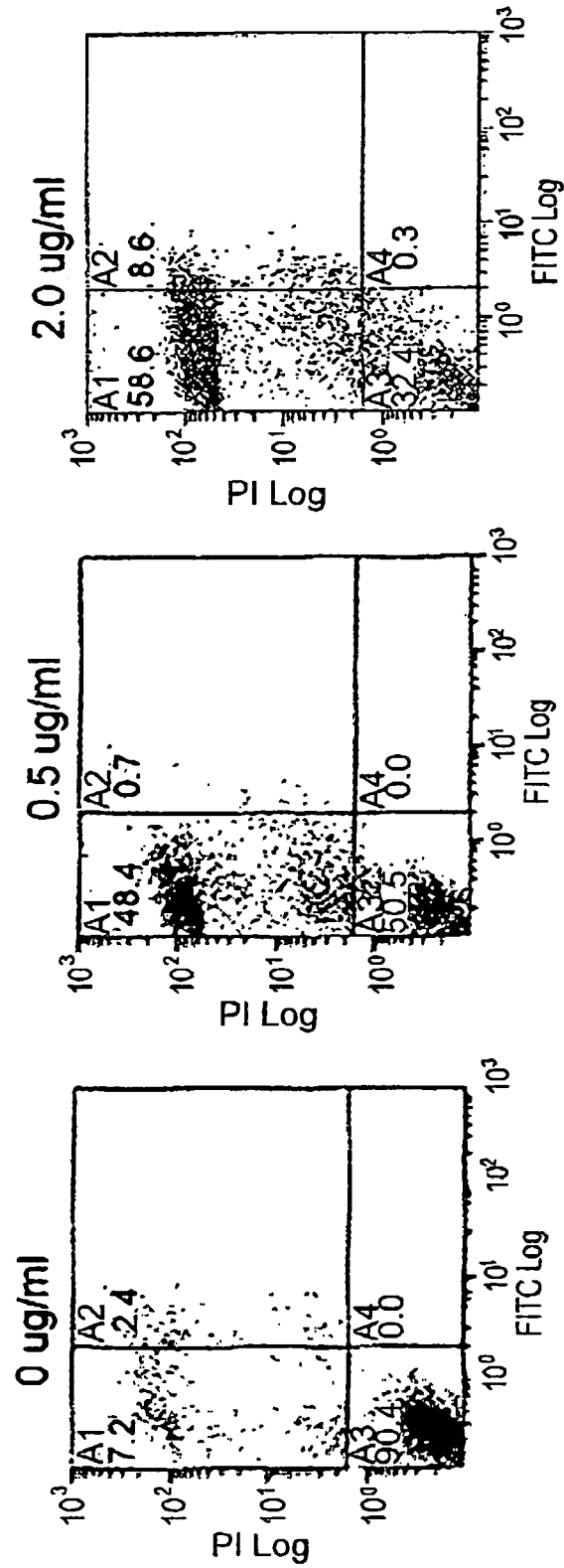
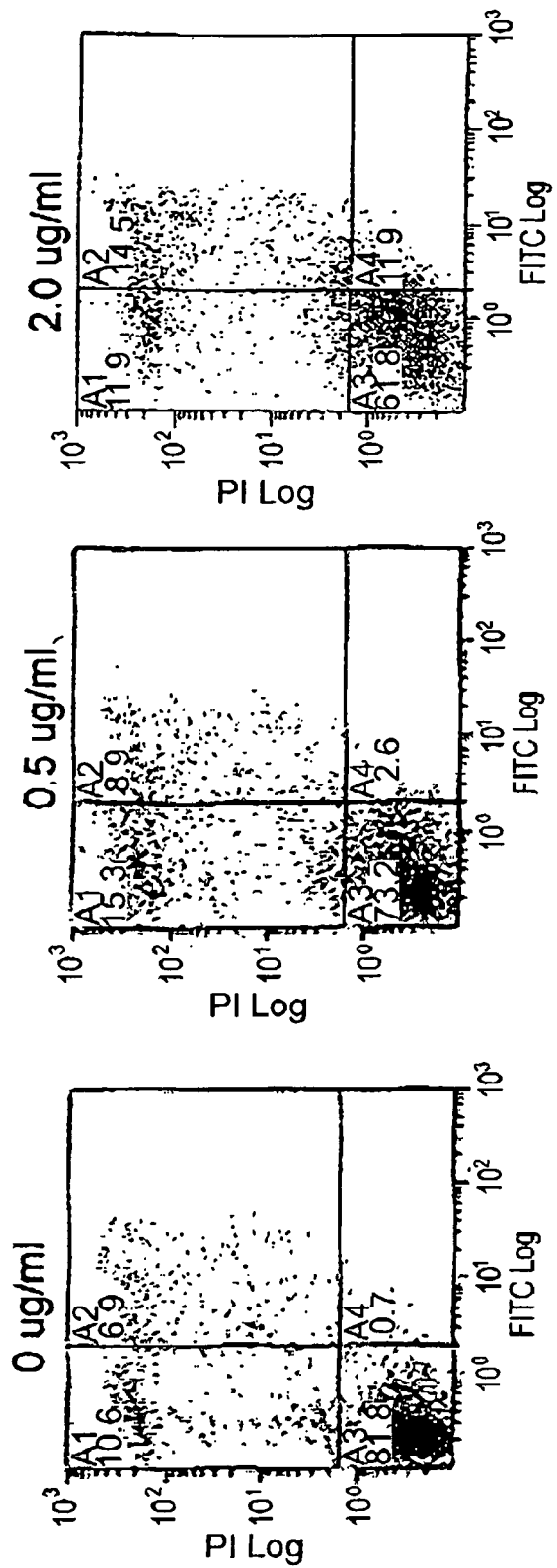

FIG. 15C
FIG. 15D
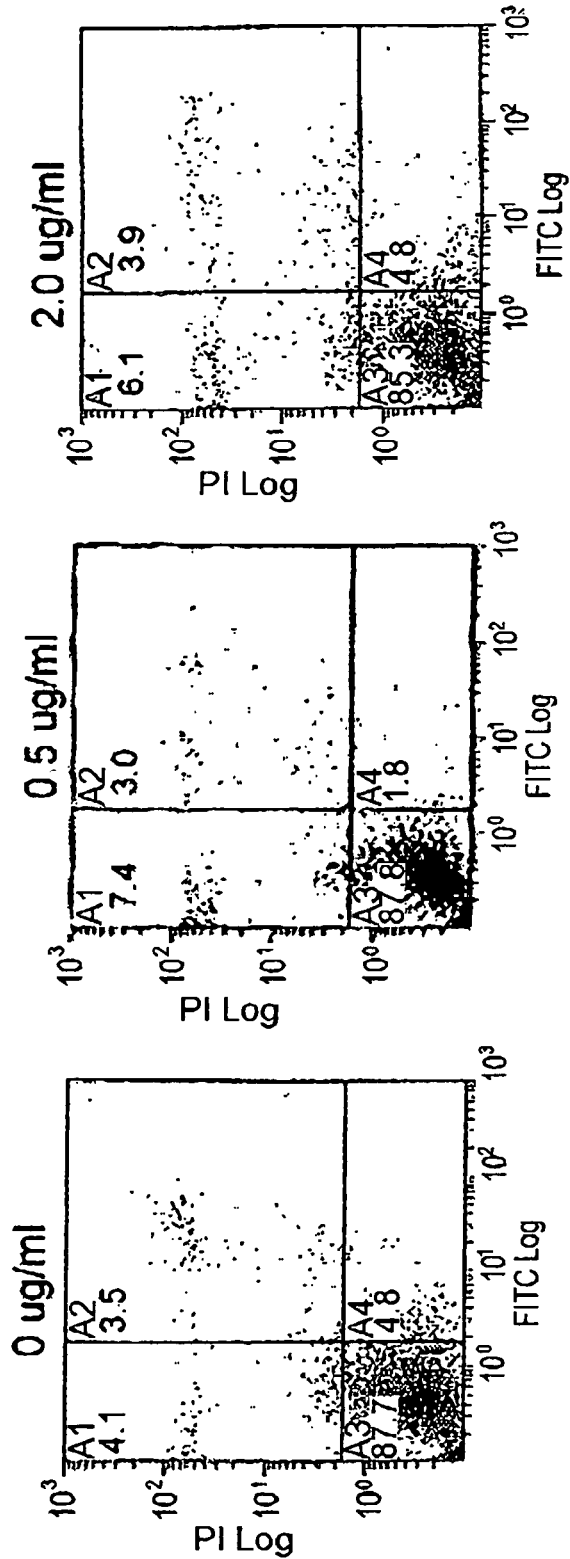
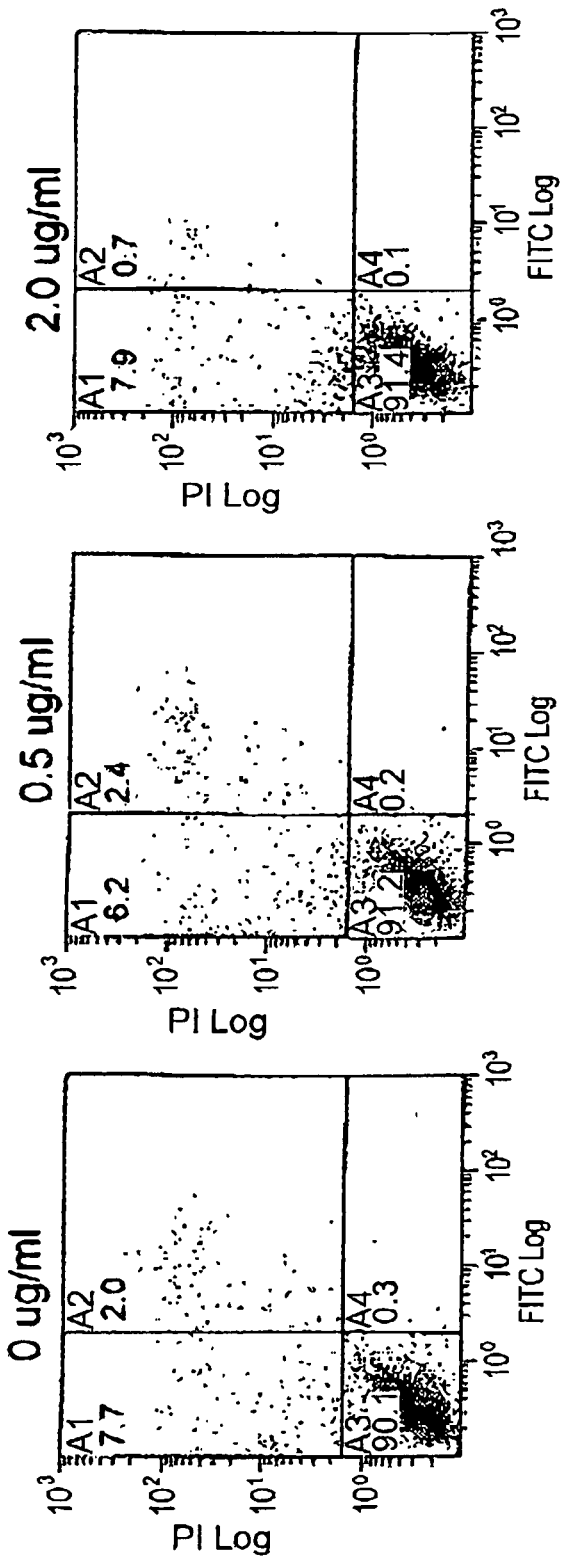

FIG. 18A
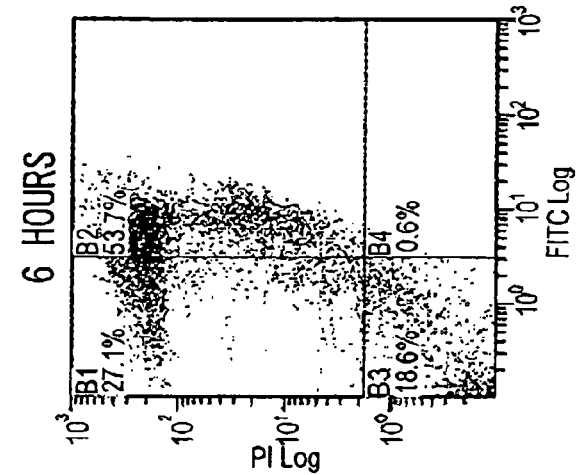
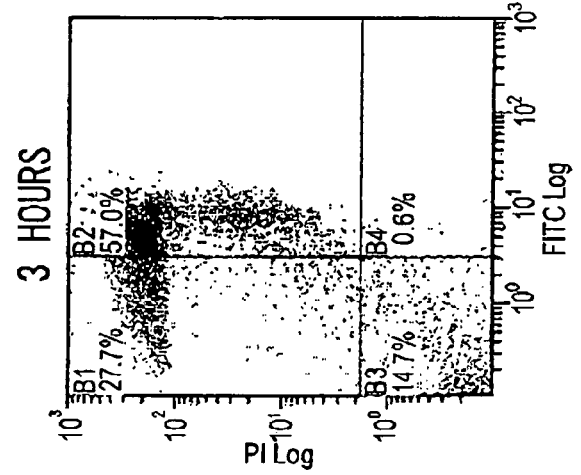
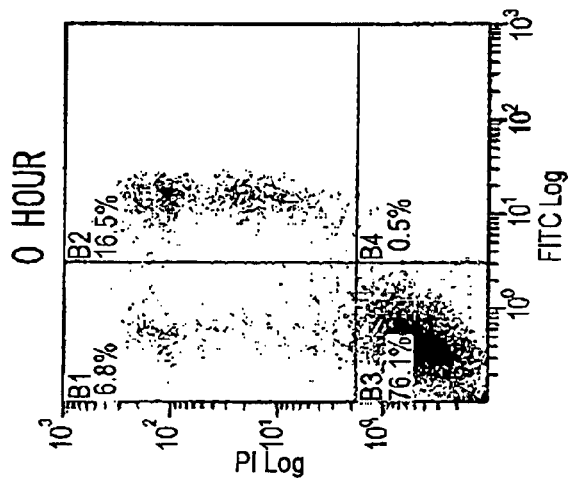
FIG. 18B
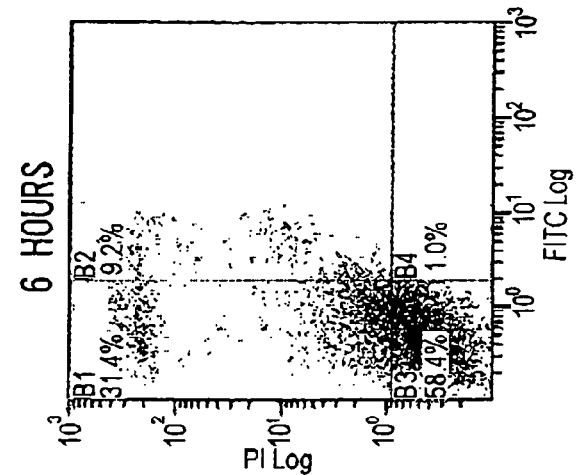
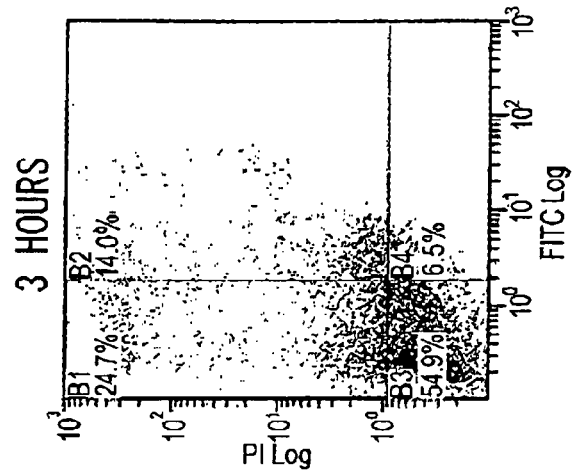
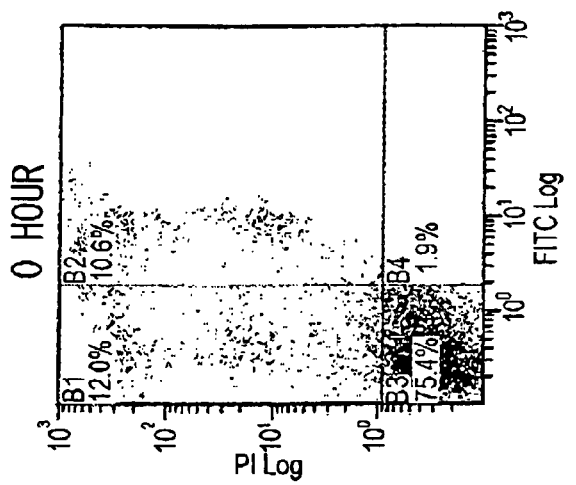

FIG. 21
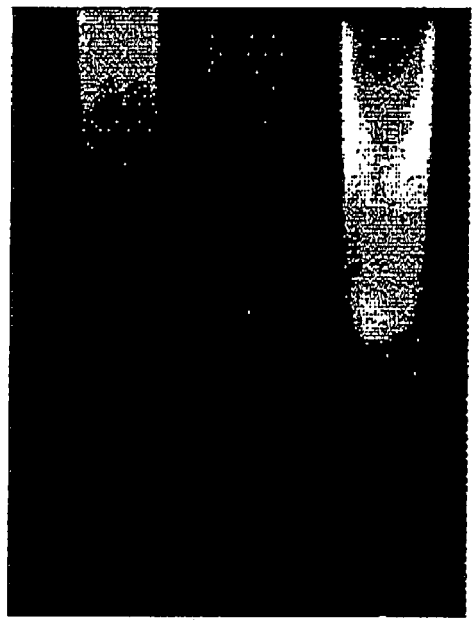
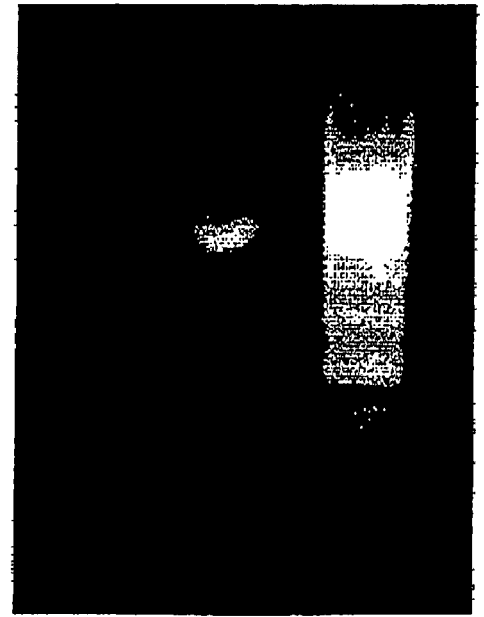

FIG. 23
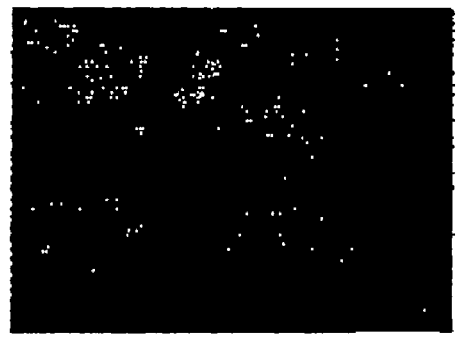
UNTREATED
2D7DB
15 MINUTES
CYTOCHALASIN D
+
2D7DB
15 MINUTES FIG. 26A          FIG. 26B
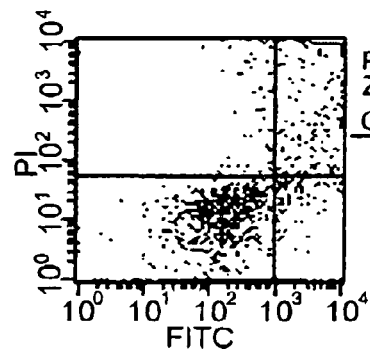
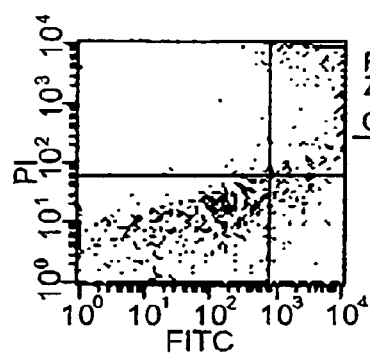
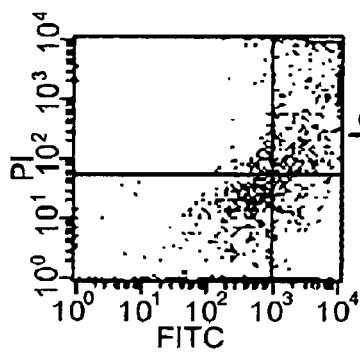
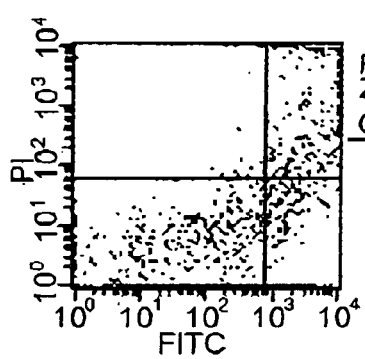
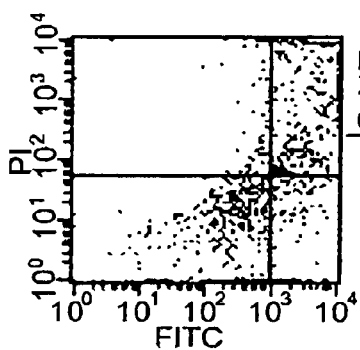
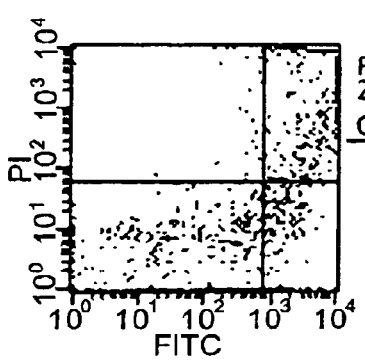

FIG. 26C
FIG. 26D
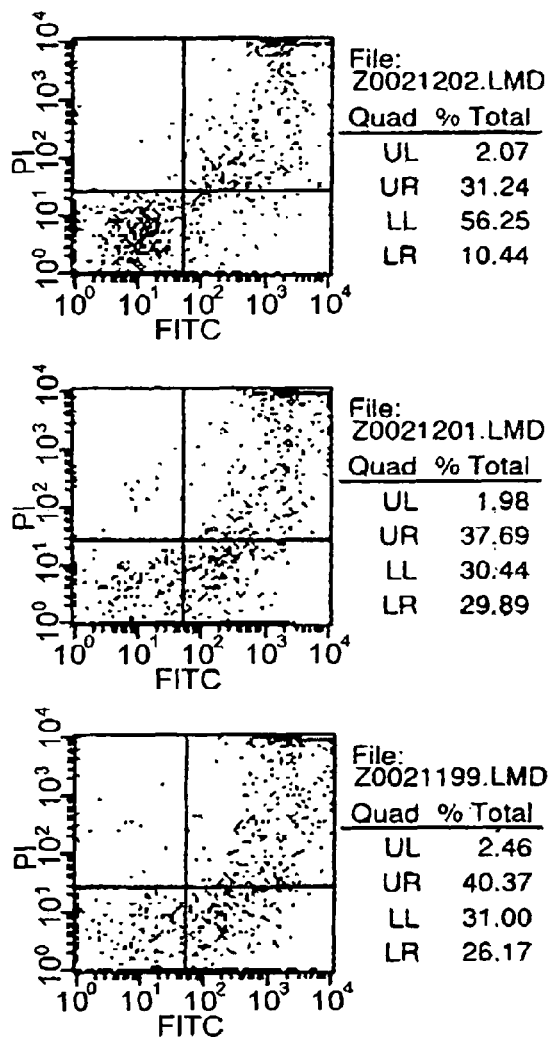
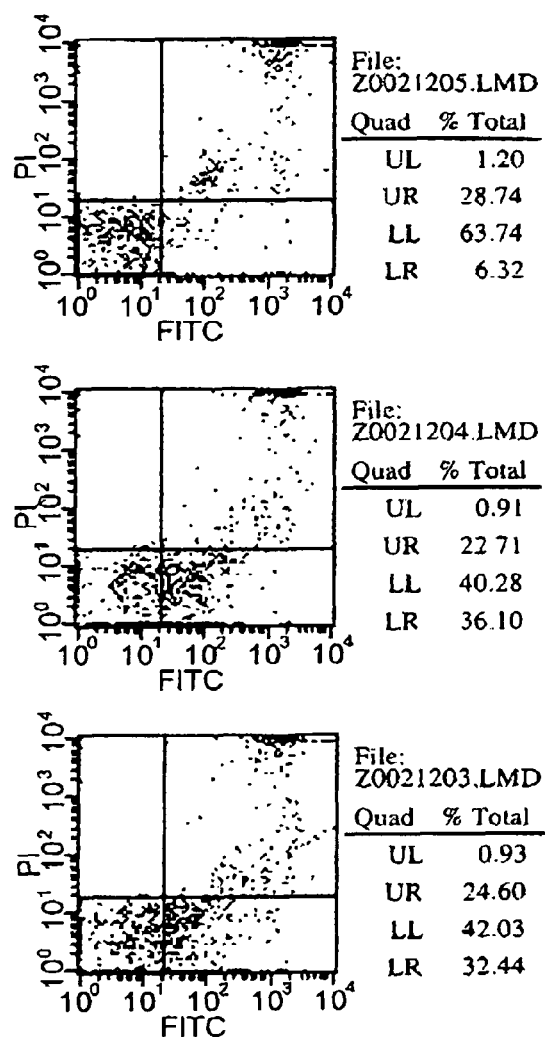

FIG. 26E
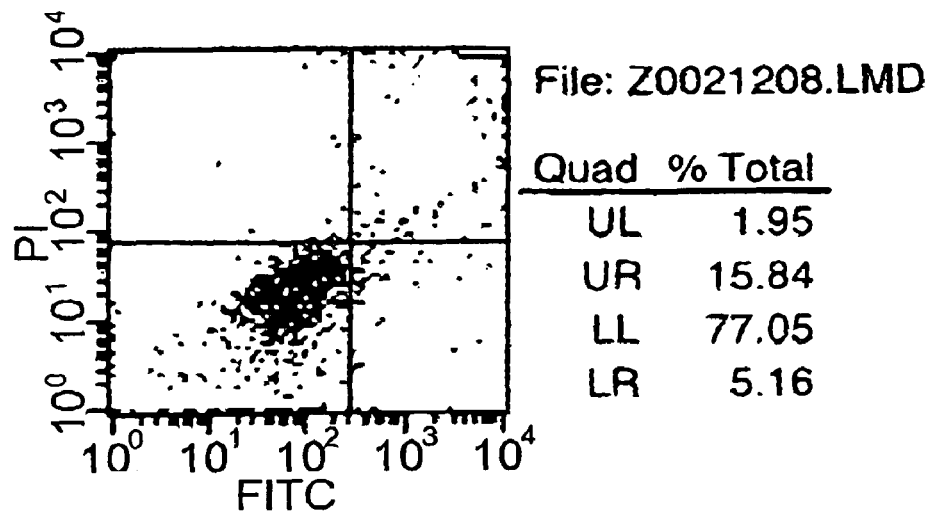
File: Z0021208.LMD
| Quad | % Total |
|---|---|
| UL | 1.95 |
| UR | 15.84 |
| LL | 77.05 |
| LR | 5.16 |
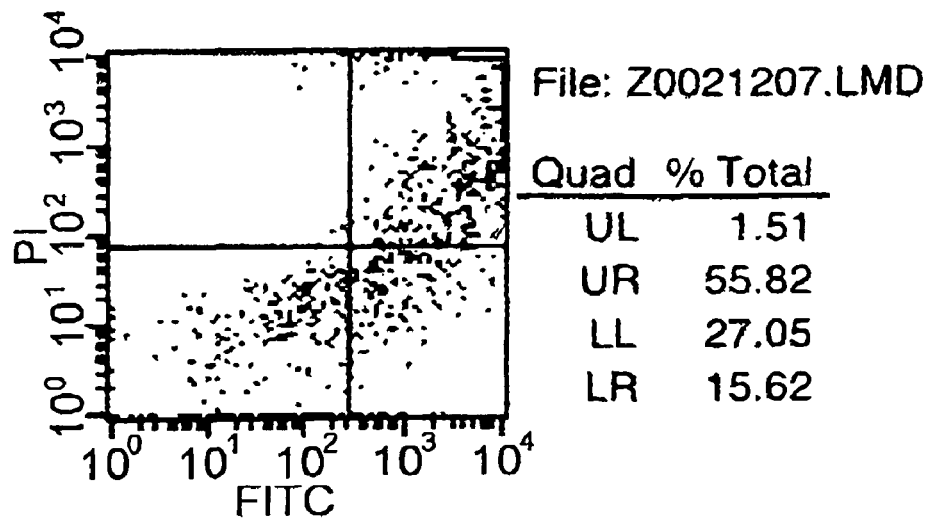
File: Z0021207.LMD
| Quad | % Total |
|---|---|
| UL | 1.51 |
| UR | 55.82 |
| LL | 27.05 |
| LR | 15.62 |
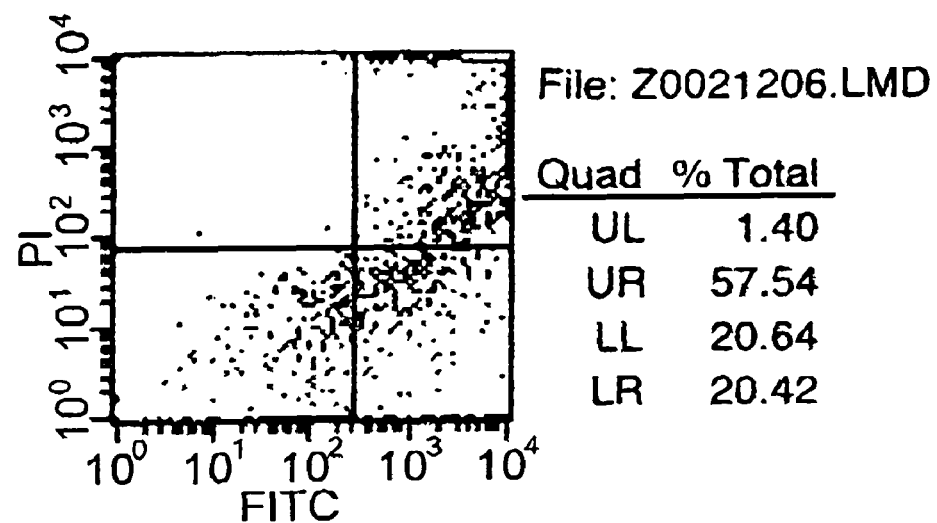
File: Z0021206.LMD
| Quad | % Total |
|---|---|
| UL | 1.40 |
| UR | 57.54 |
| LL | 20.64 |
| LR | 20.42 |

CELL DEATH-INDUCING AGENT

The present invention relates to minibodies of antibodies that recognize HLA.

BACKGROUND ART

The HLA class I antigen is formed by a heterodimer of a 45-KD α chain comprising three domains (α1, α2, α3), and a 12-KD β2 microglobulin. The main role of the HLA molecule is to present CD8+T cells with antigenic peptides, formed from about eight to ten amino acids produced inside cells. As such, it plays a very important role in the immune response and immune tolerance induced by this peptide presentation.

By ligating HLA class IA antigens with antibodies, cell growth-suppressing and cell death-inducing effects have been observed in lymphocytes, suggesting that HLA molecules may also be signal transduction molecules.

More specifically, for example, there are reports showing cell growth suppression of activated lymphocytes by the B9.12.1 antibody against the α1 domain of human HLA class IA, the W6/32 antibody against the α2 domain, and the TP25.99 and A1.4 antibodies against the α3 domain (non-patent literature 1, 2). Furthermore, two types of antibodies, MoAb90 and YTH862, against the α1 domain have been reported to induce apoptosis in activated lymphocytes (non-patent literature 2, 3, 4). Apoptosis induced by these two antibodies has been shown to be a caspase-mediated reaction (non-patent literature 4), and therefore, HLA class IA antigens expressed in lymphocytes are also speculated to be involved in apoptosis signal transduction.

Furthermore, the 5H7 antibody against the α3 domain of human HLA class IA (non-patent literature 5), and the RE2 antibody against the α2 domain of mouse HLA class IA (non-patent literature 6) have been also reported to induce cell death in activated lymphocytes and the like. However, in contrast with the aforementioned apoptosis-inducing antibodies MoAb90 and YTH862, none of the cell deaths induced by these antibodies have been shown to be mediated by caspase. Accordingly, cell deaths due to 5H7 and RE2 are predicted to be of a type completely different from conventionally known apoptosis mechanisms.

As described above, there are numerous reports of the cell growth-suppressing actions and cell death-inducing actions of anti-HLA antibodies. However, the antibodies used herein are all in the molecular forms of IgG antibodies, F(ab')2, or Fab. To date there have been no reports that cell death-inducing activity is enhanced by reducing the molecular weight of antibodies, as in F(ab')2 and Fab.

The 2D7 antibody is a mouse monoclonal antibody obtained by immunizing Balb/c mice with human myeloma cells (non-patent literature 7). The 2D7 antibody has been observed to bind very specifically to the cell surface of various lymphoid tumor cells, however, antigens recognized by the 2D7 antibody have not been identified.

Prior art literature relating to the present invention of this application is shown below.

[Non-patent Document 1] Fayen et al., Int. Immunol. 10: 1347-1358(1998)
[Non-patent Document 2] Genestier et al., Blood 90: 3629-3639 (1997)
[Non-patent Document 3] Genestier et al., Blood 90: 726-735 (1997)
[Non-patent Document 4] Genestier et al., J. Biol. Chem. 273: 5060-5066 (1998)
[Non-patent Document 5] Woodle et al., J. Immunol. 158: 2156-2164 (1997)
[Non-patent Document 6] Matsuoka et al., J. Exp. Med. 181: 2007-2015 (1995)
[Non-patent Document 7] Goto, et al. Blood 84: 1922 (1994)

DISCLOSURE OF THE INVENTION

The primary purpose of this invention is to provide minibodies of antibodies that recognize HLA class IA. A further objective of His invention is to provide novel therapeutic agents for tumors or autoimmune diseases that utilize these minibodies.

To identify antigens of the 2D7 antibody, the present inventors used random hexamers to synthesize cDNAs from the mRNAs purified from the 2D7 antigen-expressing cells, RPMI8226. These were inserted into the retrovirus vector, pMX, and a retroviral expression library was produced. The retrovirus expression library was packaged into a retrovirus by transfection into BOSC23 cells. 2D7 antigens were screened by infecting NIH3T3 cells with the virus thus obtained, staining these with 2D7 antibody, and then using FACS to perform expression analysis. Cell lysates were then prepared from RPMI8226 cells and U266 cells expressing the 2D7 antigen, and 2D7 antigens were identified by immunoprecipitation. As a result of these examinations, 2D7 antigens were proven to be HLA class I molecules.

Since the molecules recognized by 2D7 antibodies are HLA class IA, the present inventors examined whether 2D7 antibodies have cell death-inducing activity. More specifically, Jurkat cells were cultured in the presence or absence of 2D7, with anti-mouse IgG antibody also added. Cell nuclei were stained 48 hours later with Hoechst 33258, and then checked for cell nuclei fragmentation, which is characteristic of dead cells. As a result, hardly any cell death-inducing activity was observed in Jurkat cells with 2D7 antibody alone; however, by further cross-linking the antibody with anti-mouse IgG antibody, nuclei fragmentation was observed, a showing confirming that cell death was induced.

As described, because cross-linking with an anti-mouse IgG antibody is necessary for 2D7 antibody to induce cell death, it is difficult to clinically apply the 2D7 antibody to tumors or autoimmune diseases. Therefore, the present inventors examined the effect of reducing the molecular weight of the 2D7 antibody on cell death induction More specifically, genes encoding the variable regions of the 2D7 antibody were cloned from hybridomas. The 2D7 antibody was then made into diabodies using genetic engineering techniques and the effects on cell death-inducing activity was examined. Surprisingly, the 2D7 antibody converted to diabodies showed strong cell death-inducing activity within a very short time and at low doses, even without cross-linking with an anti-mouse IgG antibody. Furthermore, the diabody hardly acted on normal peripheral blood-derived lymphocytes and adherent cells, and specifically induced cell death in various myeloma cells, T cell leukemia cell lines, and activated lymphocytes. The above-mentioned results show that the minibodies of antibodies recognizing HLA can be utilized as cell death-inducing agents.

More specifically, the present invention provides the following [1] to [23]:

[1] a minibody that recognizes a human leukocyte antigen (HLA);
[2] the minibody of [1], wherein the HLA is an HLA class I;
[3] the Antibody of [2], wherein the HLA class I is an HLA-A;
[4] a minibody derived from a 2D7 antibody;

[5] the minibody of any one of [1] to [4], wherein the minibody is a diabody;

[6] a minibody of any one of (a) to (d):
(a) a minibody comprising the amino acid sequence of SEQ ID NO: 6;
(b) a minibody functionally equivalent to the minibody of (a), and comprising an amino acid sequence with a substitution, insertion, deletion and/or addition of one or more amino acids in the amino acid sequence of SEQ ID NO: 6;
(c) a minibody comprising the amino acid sequences of CDRs of SEQ ID NOs: 2 and 4; and
(d) a minibody functionally equivalent to the minibody of (c), and comprising an amino acid sequence with a substitution, insertion, deletion and/or addition of one or more amino acids in the amino acid sequence of the CDRs of SEQ ID NOs: 2 and 4;

[7] a method for producing an HA-recognizing antibody having increased activity by converting the HLA-recognizing antibody to a low-molecular-weight antibody;
[8] the method of [7], wherein the HLA is an HLA class I;
[9] the method of [8], wherein the HLA class I is an HLA-A;
[10] a method for producing a 2D7 antibody having increased activity by converting the 2D7 antibody to a low-molecular-weight antibody;
[11] the method of any one of [7] to [10], wherein the conversion step comprises conversion to a diabody;
[12] the method of any one of [7] to [11], wherein the activity is a cell death-inducing activity or a cell growth-suppressing activity;
[13] a cell death-inducing agent, comprising as an active ingredient the minibody of any one of [1] to [6], the minibody produced by the method of any one of [7] to [12], or a 2D7 antibody;
[14] the cell death-inducing agent of [13], that induces cell death of a B cell or T cell;
[15] the cell death-inducing agent of [14], wherein the B cell or T cell is an activated B cell or activated T cell;
[16] a cell growth-suppressing agent comprising as an active ingredient the minibody of any one of [1] to [6], the minibody produced by the method of any one of [7] to [12], or a 2D7 antibody;
[17] an antitumor agent comprising as an active ingredient the minibody of any one of [1] to [6], the minibody produced by the method of any one of [7] to [12], or a 2D7 antibody;
[18] the antitumor agent of [17], wherein the tumor is a blood tumor;
[19;] a therapeutic agent for an autoimmune disease, wherein the therapeutic agent comprises as an active ingredient the minibody of any one of [1] to [6], the minibody produced by the method of any one of [7] to [12], or a 2D7 antibody;
[20] the cell death-inducing agent of any one of [13] to [15], wherein the antibody is a diabody;
[21] the cell growth-suppressing agent of [16]; wherein the antibody is a diabody;
[22] the antitumor agent of [17] or [18], wherein the antibody is a diabody; and
[23] the therapeutic agent for autoimmune disease of [19], wherein the antibody is a diabody;

The present invention provides minibodies that recognize HLA. The minibodies of this invention are useful since their activity is elevated. Herein activity refers to a biological action that is caused by binding an antibody to an antigen. Specific examples include cell death-inducing actions, apoptosis-inducing actions, cell growth-suppressing actions, cell differentiation-suppressing actions, cell division-suppressing actions, cell growth-inducing actions, cell differentiation-inducing actions, cell division-inducing actions, and cell cycle-regulating actions. Cell death-inducing actions and cell growth-suppressing actions are preferred.

The cells that become the target of the above-mentioned actions, such as cell death-inducing actions and cell growth-suppressing actions, are not particularly limited, though white blood cells and non-adherent cells are preferred. Specific examples of white blood cells include lymphocytes (B cells, T cells), neutrophils, eosinophils, basophils, monocytes (preferably activated peripheral blood mononuclear cells (PBMC)), and myeloma cells, while lymphocytes (B cells, T cells), and myeloma cells are preferred, and T cells or B cells (particularly activated B cells or activated T cells) are most preferable. non-adherent cells refer to cells that, when cultured, grow in a suspended state without adhering to the surface of culturing vessels of glass, plastic or the like. On the other hand, adherent cells refer to cells that, when cultured, adhere to the surface of culturing vessels of glass, plastic or the like.

In the present invention, administration of the minibodies that recognize HLA can treat or prevent diseases such as tumors including blood tumors (hematopoietic tumors) (specific examples include leukemia, myelodysplastic syndrome, malignant lymphoma, chronic myelogenic leukemia, plasmacytic disorder (myeloma, multiple myeloma, macroglobulinemia), and myeloproliferative disease (polycythemia vera, essential thrombocythemia, idiopathic myelofibrosis)), and autoimmune diseases (specific examples include rheumatism, autoimmune hepatitis, autoimmune thyroiditis, autoimmune bullosis, autoimmune adrenocortical disease, autoimmune hemolytic anemia, autoimmune thrombycytopenic purpura, autoimmune atrophic gastritis, autoimmune neutropenia, autoimmune orchitis, autoimmune encephalomyelitis, autoimmune receptor disease, autoimmune infertility, Crohn's disease, systemic lupus erythematosus, multiple sclerosis, Basedow's disease, juvenile diabetes, Addison's disease, myasthenia gravis, lens-induced uveitis, psoriasis, and Behchet's disease).

In the present invention, HLA refers to human leukocyte antigen. HLA molecules are categorized into class I and class II. Known examples of class I are HLA-A, B, C, E, F, G, H, J, and such; and known examples of class II are HLA-DR, DQ, DP, and such. The antigens recognized by the antibodies of this invention are not particularly limited, so long as they are HLA molecules, preferably molecules classified as class I, and more preferably HLA-A.

In the present invention, a minibody comprises an antibody fragment that lacks a portion of a whole antibody (for example, whole IgG). The minibodies of the present invention are not particularly limited so long as they can bind an antigen. There are no particular limitations on the antibody fragments of the present invention, so long as they are portions of a whole antibody, and preferably contain a heavy chain variable region (VH) or a light chain variable region (VL). More preferably, the antibody fragments contain both a heavy chain variable region (VH) and a light chain variable region (VL). Specific examples of the antibody fragments include Fab, Fab', F(ab')2, Fv, and scFv (single chain Fv), but are preferably scFv (Huston, J. S. et al., Proc. Natl. Acad. Sci. U.S.A. (1988) 85, 5879-5883; Plickthun "The Pharmacology of Monoclonal Antibodies" Vol. 113, Resenburg and Moore Ed., Springer Verlag, New York, pp. 269-315, (1994)). Such antibody fragments can be prepared by treating an antibody with an enzyme, such as papain or pepsin for example, to generate antibody fragments, or by constructing genes that encode these antibody fragments, introducing them into expression vectors, and then expressing them in appropriate host cells (see, for example, Co, M. S. et al., 1994, J. Immunol. 152, 2968-2976; Better, M. and Horwitz, A. H., 1989, Methods Enzymol. 178, 476-496; Pluckthun, A. and Skerra, A., 1989, Methods Enzymol. 178, 497-515; Lamoyi, E., 1986, Methods Enzymol. 121, 652-663; Rousseaux, J. et al., 1986, Methods Enzymol. 121, 663-669; Bird, R. E. and Walker, B. W., 1991, Trends Biotechnol. 9, 132-137).

The minibodies of this invention preferably have smaller molecular weights than a whole antibody, however, they may form multimers, including dimers, trimers, and tetramers, and the molecular weights may become greater than that of the whole antibody.

A preferred minibody of this invention is an antibody comprising two or more antibody VHs and two or more antibody VLs, in which each of these variable regions is linked directly or indirectly via linkers and such. Such linkages may be covalent bonds or non-covalent bonds, or may be both. An even more preferable minibody is an antibody comprising two or more VH-VL pairs formed by non-covalent bonding between VH and VL. In this case, the distance between one VU-VL pair and another VH-VL pair is preferably shorter in a minibody than in a whole antibody.

A particularly favorable minibody of this invention is a diabody. A diabody is a dimer formed by bonding two fragments, in which a variable region is linked to another variable region via a linker and such (for example, scfv) (hereinafter referred to as diabody-constituting fragments), and usually comprises two VLs and two VHs (P. Holliger et al., Proc. Natl. Acad. Sci. USA, 90, 6444-6448 (1993); EP404097; WO93/11161; Johnson et al., Method in Enzymology, 203, 88-98, (1991); Holliger et al., Protein Engineering, 9, 299-305, (1996); Perisic et al., Structure, 2, 1217-1226, (1994); John et al., Protein Engineering, 12(7), 597-604, (1999); Holliger et al., Proc. Natl. Acad. Sci. USA., 90, 6444-6448, (1993); Atwell et al., Mol. Immunol. 33, 1301-1312, (1996)). The bonds between the diabody-constituting fragments may be non-covalent or covalent bonds, but are preferably non-covalent bonds.

Alternatively, diabody-constituting fragments may be bound by a linker and such to form a single chain diabody (sc diabody). In such cases, linking the diabody-constituting fragments using a long linker of about 20 amino acids allows diabody-constituting fragments on the same chain to form a dimer via non-covalent bonds to each other.

Diabody-constituting fragments include those with a linked VL-VH, linked VL-VL, and linked VH-VH, and are preferably those with a linked VH-VL. In the diabody-constituting fragments, the linker used to link a variable region to a variable region is not particularly limited, but is preferably a linker short enough to prevent non-covalent bonding between variable regions in the same fragment. The length of such a linker can be appropriately determined by those skilled in the art, and is ordinarily 2 to 14 amino acids, preferably 3 to 9 amino acids, and most preferably 4 to 6 amino acids. In this case, linkers between a VL and VH encoded on the same fragment are short, and thus a VL and VH on the same strand do not form a non-covalent bond nor a single-chain V region fragment, rather, the fragment forms a dimer with another fragment via non-covalent bonding. Furthermore, according to the same principle as in diabody construction, three or more diabody-constituting fragments may be bonded to form multimeric antibodies, such as trimers and tetramers.

Examples of the diabodies of this invention are, without limitation, a diabody comprising the amino acid sequence of SEQ ID NO: 6, or a diabody that is functionally equivalent to a diabody comprising the sequence of SEQ ID NO: 6, which comprises an amino acid sequence with a mutation (substitutions, deletion, insertion, and/or addition) of one or more amino acids in the amino acid sequence of SEQ ID NO: 6; and a diabody comprising the amino acid sequence of a complementarity-determining region (CDR) (or a variable region) of SEQ ID NO: 2 and a CDR (or a variable region) of SEQ ID NO: 4, or a diabody that is functionally equivalent to a diabody comprising the amino acid sequence of a CDR (or variable region) of SEQ ID NO: 2 and a CDR (or a variable region) of SEQ ID NO: 4, which comprises an amino acid sequence with mutations (substitution, deletion, insertion, and/or addition) of one or more amino acids in the amino acid sequence of a CDR (or a variable region) of SEQ ID NO: 2 and a CDR (or a variable region) of SEQ ID NO: 4.

Herein, "functionally equivalent" means that the diabody of interest has an activity equivalent to an activity of a diabody comprising the sequence of SEQ ID NO: 6, or a diabody comprising the sequence of a CDR (or a variable region) of SEQ ID NO: 2 and a CDR (or a variable region) of SEQ ID NO: 4 (for example, HLA-A binding activity, and cell death-inducing activity).

The number of mutated amino acids is not limited, but may ordinarily be 30 amino acids or less, preferably 15 amino acids or less; and more preferably five amino acids or less (for example, three amino acids or less).

Furthermore, a diabody comprising the amino acid sequence of SEQ ID NO: 6, or a diabody comprising the sequence of a CDR (or a variable region) of SEQ ID NO: 2 and a CDR (or a variable region) of SEQ ID NO: 4 may be humanized or chimerized to reduce heterologous antigenicity against humans.

In the amino acid sequence of SEQ ID NO: 2, amino acids 1 to 134 correspond to the variable region, amino acids 50 to 54 correspond to CDR1, amino acids 69 to 85 correspond to CDR2, and amino acids 118 to 134 correspond to CDR3. In the amino acid sequence of SEQ ID NO: 4, amino acids 1 to 128 correspond to the variable region, amino acids 46 to 55 correspond to CDR1, amino acids 71 to 77 correspond to CDR2, and amino acids 110 to 128 correspond to CDR3.

In the present invention, the HLA-recognizing minibodies specifically bind to HLA. They are not particularly limited, so long as they have a biological action. The minibodies of this invention can be prepared by methods well known to those skilled in the art. For example, as described in the Examples, the antibodies can be prepared based on the sequence of an HLA-recognizing antibody (particularly sequences of the variable regions and sequences of CDRs), using genetic engineering techniques known to those skilled in the art.

For the sequence of the HLA-recognizing antibody, a well-known antibody sequence can be used, or an anti-HLA antibody can be prepared by a method well known to those skilled in the art using HLA as the antigen, and then the sequence of this antibody can be obtained and then used. Specifically, for example, this can be performed as follows: HLA protein or its fragment is used as a sensitizing antigen to perform immunizations according to conventional immunization methods, the obtained immunocytes are fused with well-known parent cells according to conventional cell fusion methods, and monoclonal antibody-producing cells (hybridomas) are then screened by ordinary screening methods. Antigens can be prepared by known methods, such as a method using baculovituses (WO98/46777 and such). Hybridomas can be prepared, for example, according to the method of Milstein et al. (Kohler, G. and Milstein, C., Methods Enzymol. (1981) 73:346). When the antigen has low immunogenicity, immunization can be performed using the antigen bound to Immunogenic macromolecules, such as albumin. Thereafter, cDNAs of the variable region (V region) of the antibody are synthesized from the mRNAs of the hybridomas using reverse transcriptase, and the sequences of the obtained cDNAs can be determined by known methods.

Antibodies that recognize HLA are not particularly limited, so long as they bind to HLA; mouse antibodies, rat antibodies, rabbit antibodies, sheep antibodies, human antibodies, and such may be used as necessary. Alternatively, artificially modified, genetically recombinant antibodies, such as chimeric and humanized antibodies, may be used to reduce heterologous antigenicity against humans. These modified antibodies can be produced using known methods. A chimeric antibody is an antibody comprising the variable regions of the heavy and light chains of an antibody from a non-human mammal such as a mouse, and the constant regions of the heavy and light chains of a human antibody. The chimeric antibody can be produced by linking a DNA encoding the variable regions of the mouse antibody with a DNA encoding the constant regions of the human antibody, incorporating this into an expression vector, and then introducing the vector to a host.

Humanized antibodies are also referred to as "reshaped human antibodies". Such humanized antibodies are obtained by transferring the CDR of an antibody derived from a non-human mammal, for example a mouse, to the CDR of a human antibody, and general gene recombination procedures for this are also known. Specifically, a DNA sequence designed to link a murine antibody CDR to the framework region (FR) of a human antibody can be synthesized by PCR, using primers prepared from several oligonucleotides containing overlapping portions of terminal regions. The obtained DNA is linked to a DNA encoding human antibody constant regions, and this is then integrated into an expression vector, and the antibody is produced by introducing this vector into host cells (see European Patent Application EP 239400, and International Patent Application WO 96/02576). The human antibody FR to be linked via the CDR is selected so the CDR forms a favorable antigen-binding site. To form a suitable antigen-binding site, amino acids in the framework region of the antibody variable region may be substituted in the CDR of the reshaped human antibody, as necessary (Sato, K. et al, 1993, Cancer Res. 53, 851-856).

These chimeric antibodies and humanized antibodies can be chimerized, humanized, and such after their molecular weight is reduced, or their molecular weight can be reduced after they have been chimerized, humanized, or such.

Methods for obtaining human antibodies are also known. For example, human lymphocytes can be sensitized in vitro with a desired antigen, or with cells expressing the desired antigen, and the sensitized lymphocytes can be fused with human myeloma cells, such as U266, to obtain the desired human antibody with antigen-binding activity (Examined Published Japanese Patent Application No. (JP-B) Hei 1-59878). Further, a desired human antibody can be obtained by using a desired antigen to immunize transgenic animals that have a fill repertoire of human antibody genes (see International Patent Application WO 93/12227, WO 92/03918, WO 94/02602, WO 94/25585, WO 96/34096, and WO 96/33735). Furthermore, techniques for obtaining human antibodies by panning using a human antibody library are also known. For example, variable regions of human antibodies can be expressed as single chain antibodies (scFvs) on the surface of phages using phage display methods, and phages that bind to antigens can be selected. The DNA sequences that encode the variable regions of the human antibodies binding the antigens can be determined by analyzing the genes of the selected phages. By determining the DNA sequences of the scFvs that bind to the antigens, appropriate expression vectors carrying relevant sequences can be produced to yield human antibodies. These methods are already known, and are detailed in the following publications: WO 92/01047, WO 92/20791, WO 93/06213, WO 93/11236, WO 93/19172, WO 95/01438, and WO 95/15388.

In the present invention, favorable examples of antibodies that recognize HLA include 2D7 antibodies. Examples of 2D7 antibodies are antibodies comprising the sequences of a CDR (or a variable region) of SEQ ID NO: 2 and a CDR (or a variable region) of SEQ ID NO: 4, but are not limited thereto. The 2D7 antibodies of this invention include an antibody which is functionally equivalent to an antibody that comprises the sequence of a CDR (or a variable region) of SEQ ID NO: 2 and a CDR (or a variable region) of SEQ ID NO: 4, and which comprises an amino acid sequences with a mutation (substitution, deletion, insertion, and/or addition) of one or more amino acids in the amino acid sequence of a CDR (or a variable region) of SEQ ID NO: 2 and a CDR (or a variable region) of SEQ ID NO: 4. Herein, "functionally equivalent" means that an antibody of interest has an activity (for example, HLA-A binding activity, and cell death-inducing activity) equivalent to an antibody comprising the sequence of a CDR (or a variable region) of SEQ ID NO: 2 and a CDR (or a variable region) of SEQ ID NO: 4.

The number of mutated amino acids is not particularly limited, but may be ordinarily 30 amino acids or less, preferably 15 amino acids or less, and more preferably five amino acids or less (for example, three amino acids or less). The amino acids are preferably mutated or modified in a way that conserves the properties of the amino acid side chain. Examples of amino acid side chain properties are: hydrophobic amino acids (A, I, L, M, F, P, W, Y, and V), hydrophilic ado acids (R, D, N, C, E, Q, G, H, K, S, and T), amino acids comprising the following side chains: aliphatic side chains (G, A, V, L, I, and P); hydroxyl-containing side chains (S, T, and Y); sulfur-containing side chains (C and M); carboxylic acid- and amide-containing side chains (D, N, E, and Q); basic side chains (R, K, and H); aromatic ring-containing side chains (H, F, Y, and W) (amino acids are represented by one-letter codes in parentheses). Polypeptides comprising a modified amino acid sequence, in which one or more amino acid residues is deleted, added, and/or replaced with other amino acids, are known to retain their original biological activities (Mark, D. F. et al., Proc. Natl. Acad. Sci. USA 81, 5662-5666 (1984); Zoller, M. J. & Smith, M. Nucleic Acids Research 10, 6487-6500 (1982); Waug, A. et al., Science 224, 1431-1433; Dalbadie-McFarland, G. et al., Proc. Natl. Acad. Sci. USA 79, 6409-6413 (1982)). In addition, the amino acid sequences of the antibody constant regions and such are well known to those skilled in the art.

Furthermore, the 2D7 antibodies can be chimerized, humanized, or such by methods well known to those skilled in the art. Such chimeric and humanized antibodies are also included in the 2D7 antibodies of this invention.

The antibodies of this invention may be conjugated antibodies that are bonded to various molecules, such as polyethylene glycol (PEG), radioactive substances, and toxins. Such conjugate antibodies can be obtained by performing chemical modifications on the obtained antibodies. Methods for antibody modification are established in this field. The term "antibody" in this invention includes such conjugate antibodies.

The present invention includes DNAs that encode the antibodies of this invention. This invention also includes DNAs encoding antibodies that hybridize under stringent conditions to the aforementioned DNAs, and have antigen-binding capacity and activity. Hybridization techniques (Sambrook, J. et al., Molecular Cloning 2nd ed., 9.47-9.58, Cold Spring Harbor Lab. press, 1989) are well known to those skilled in the art, and hybridization conditions can be selected appropriately by those skilled in the art. Such hybridization conditions include, for example, conditions of low stringency. Examples of conditions of low stringency include post-hybridization washing in 0.1×SSC and 0.1% SDS at 42° C., and preferably in 0.1×SSC and 0.1% SDS at 50° C. More preferable hybridization conditions include those of high stringency. Highly stringent conditions include, for example, washing in 5×SSC and 0.1% SDS at 65° C. In these conditions, the higher the temperature, the higher the expectation of efficiently obtaining DNAs with a high homology. However, several factors, such as temperature and salt concentration, can influence hybridization stringency, and those skilled in the art can suitably select these factors to achieve similar stringencies.

The DNAs of this invention are used for in vivo and in vitro production of the antibodies of this invention, and for other applications, such as gene therapy. The DNAs of this invention may be in any form, so long as they encode the antibodies of this invention. More specifically, they may be cDNAs synthesized from mRNAs, genomic DNAs, chemically synthesized DNAs, or such. Furthermore, the DNAs of this invention include any nucleotide sequence based on the degeneracy of the genetic code, so long as they encode the antibodies of this invention.

The antibodies of this invention can be produced by methods well known to those skilled in the art. More specifically, a DNA of an antibody of interest is incorporated into an expression vector. In so doing, the DNA is incorporated into the expression vector and expressed under the control of an expression regulatory region such as an enhancer or promoter. Next, antibodies can be expressed by transforming host cells with this expression vector. In this regard, appropriate combinations of hosts and expression vectors can be used.

The vectors include, for example, M13 vectors, pUC vectors, pBR322, pBluescript, and pCR-Script. In addition to the above vectors, for example, pGEM-T, pDMECT, and pT7 can also be used for the subcloning and excision of cDNAs.

When using vectors to produce the antibodies of this invention, expression vectors are particularly useful. When an expression vector is expressed in *E. coli,* for example, it should have the above characteristics in order to be amplified in *E. coli.* Additionally, when *E. coli* such as JM109, DH5 α, HB101, or XL1-Blue are used as the host cell, the vector preferably has a promoter, for example, a lacZ promoter (Ward et al. (1989) Nature 341:544-546; (1992) FASEB J. 6:2422-2427), araB promoter (Better et al. (1988) Science 240:1041-1043), or T7 promoter, to allow efficient expression of the desired gene in *E. coli.* Other examples of the vectors include pGEX-5X-1 (Pharmacia), "QIAexpress system" (QIAGEN), pEGFP, and pET (where BL21, a strain expressing T7 RNA polymerase, is preferably used as the host).

Furthermore, the vector may comprise a signal sequence for polypeptide secretion. When producing proteins into the periplasm of *E. coli,* the pelB signal sequence (Lei, S. P. et al. J. Bacteriol. 169:4379 (1987)) may be used as a signal sequence for protein secretion. For example, calcium chloride methods or electroporation methods may be used to introduce the vector into a host cell.

In addition to *E. coli,* expression vectors derived from mammals (e.g., pCDNA3 (Invitrogen), pEGF-BOS (Nucleic Acids Res. (1990) 18(17):5322), pEF, pCDM8), insect cells (e.g., "Bac-to-BAC baculovirus expression system" (GIBCO-BRL), pBacPAK8), plants (e.g., pMH1, pMH2), animal viruses (e.g., pHSV, pMV, pAdexLcw), retroviruses (e.g., pZIPneo), yeasts (e.g., "Pichia Expression Kit" (Invitrogen), pNV11, SP-Q01), and *Bacillus subtilis* (e.g., pPL608, pKTH50) may also be used as a vector for producing the polypeptide of the present invention.

In order to express proteins in animal cells, such as CHO, COS, and NIH3T3 cells, the vector preferably has a promoter necessary for expression in such cells, for example, an SV40 promoter (Mulligan et al. (1979) Nature 277:108), MMLV-LTR promoter, EF1αpromoter (Mizushima et al. (1990) Nucleic Acids Res. 18:5322), CMV promoter, etc.). It is even more preferable that the vector also carry a marker gene for selecting transformants (for example, a drug-resistance gene enabling selection by a drug, such as neomycin and G418). Examples of vectors with such characteristics include pMAM, pDR2, pBK-RSV, pBK-CMV, pOPRSV, pOP13, and such.

In addition, to stably express a gene and amplify the gene copy number in cells, CHO cells having a defective nucleic acid synthesis pathway can be introduced with a vector containing a DHFR gene (for example, pCHOI) to compensate for the defect, and the copy number may be amplified using methotrexate (MTX). Alternatively, a COS cell, which carries an SV40 T antigen-expressing gene on its chromosome, can be transformed with a vector containing the SV40 replication origin (for example, pcD) for transient gene expression. The replication origin may be derived from polyoma viruses, adenoviruses, bovine papilloma viruses (BPV), and such. Furthermore, to increase the gene copy number in host cells, the expression vector may contain, as a selection marker, an aminoglycoside transferase (APH) gene, thymidine kinase (TK) gene, *E. coli* xanthine guanine phosphoribosyl transferase (Ecogpt) gene, dihydrofolate reductase (dhfr) gene, and such.

Methods for expressing the DNAs of this invention in the bodies of animals include methods of incorporating the DNAs of this invention into appropriate vectors and introducing them into living bodies by, for example, a retrovirus method, liposome method, cationic liposome method, or adenovirus method. The vectors that are used include adenovirus vectors (for example, pAdexlcw), and retrovirus vectors (for example, pZIPneo), but are not limited thereto. General genetic manipulations such inserting the DNAs of this invention into vectors can be performed according to conventional methods (Molecular Cloning, 5.61-5.63). Administration to living bodies can be carried out by ex vivo method or in vivo methods.

Furthermore, the present invention provides host cells into which a vector of this invention is introduced. The host cells into which a vector of this invention is introduced are not particularly limited; for example, *E. coli* and various animal cells are available for this purpose. The host cells of this invention may be used, for example, as production systems to produce and express the antibodies of the present invention. In vitro and in vivo production systems are available for polypeptide production systems. Production systems that use eukaryotic cells or prokaryotic cells are examples of in vitro production systems.

Eukaryotic cells that can be used include, for example, animal cells, plant cells, and fungal cells. Known animal cells include:,mammalian cells, for example, CHO (J. Exp. Med. (1995)108, 945), COS, 3T3, myeloma, BHK (baby hamster kidney), HeLa, Vero, amphibian cells such as *Xenopus laevis* oocytes (Valle, et al. (1981) Nature 291, 358-340), or insect cells (e.g., Sf9, Sf21, and Tn5). CHO cells in which the DHFR gene has been deleted, such as dhfr-CHO (Proc. Natl. Acad. Sci. USA (1980) 77, 4216-4220) and CHO K-1 (Proc. Natl. Acad. Sci. USA (1968)60, 1275), are particularly preferable for use as CHO cells. Of the animal cells, CHO cells are particularly favorable for large-scale expression. Vectors can be introduced into a host cell by, for example, calcium phosphate methods, DEAE-dextran methods, methods using cationic liposome DOTAP (Boehringer-Mannheim), electroporation methods, lipofection methods, etc.

Plant cells include, for example, Nicotiana tabacum-derived cells known as polypeptide production systems. Calluses may be cultured from these cells. Known fungal cells include yeast cells, for example, the genus Saccharomyces, such as Saccharomyces cerevisiae; and filamentous fungi, for example, the genus Aspergillus such as Aspergillus niger.

Bacterial cells can be used in prokaryotic production systems. Examples of bacterial cells include E. coli (for example, JM109, DH5α, HB101 and such); and Bacillus subtilis.

Antibodies can be obtained by transforming the cells with a polynucleotide of interest, then culturing these transformants in vitro. Transformants can be cultured using known methods. For example, DMEM, MEM, RPMI 1640, or IMDM may be used as the culture medium for animal cells, and may be used with or without serum supplements such as fetal calf serum (FCS). Serum-free cultures are also acceptable. The preferred pH is about 6 to 8 over the course of culturing. Incubation is typically carried out at a temperature of about 30 to 40° C. for about 15 to 200 hours. Medium is exchanged, aerated, or agitated, as necessary.

On the other hand, production systems using animal or plant hosts may be used as systems for producing polypeptides in vivo. For example, a DNA of interest may be introduced into an animal or plant, and the polypeptide produced in the body of the animal or plant is then recovered. The "hosts" of the present invention include such animals and plants. When using animals, there are production systems using mammals or insects.

Mammals such as goats, pigs, sheep, mice, and cattle may be used (Vicki Glaser SPECTRUM Biotechnology Applications (1993)). Alternatively, the mammals may be transgenic animals.

For example, a DNA of interest may be prepared as a fusion gene with a gene encoding a polypeptide specifically produced in milk, such as the goat β-casein gene. DNA fragments containing the fusion gene are injected into goat embryos, which are then introduced back to female goats. The desired antibody can then be obtained from milk produced by the transgenic goats, which are born from the goats that received the embryos, or from their offspring. Appropriate hormones may be administered to increase the volume of milk containing the polypeptide produced by the transgenic goats (Ebert, K. M. et al., Bio/Technology 12, 699-702 (1994)).

Insects, such as silkworms, may also be used. Baculoviruses carrying a DNA of interest can be used to infect silkworms, and the antibody of interest can be obtained from their body fluids (Susumu, M. et al., Nature 315, 592-594 (1985)).

When using plants, tobacco can be used, for example. When tobacco is used, a DNA of interest may be inserted into a plant expression vector, for example, pMON 530, and then the vector may be introduced into a bacterium, such as Agrobacterium tumefaciens. The bacteria are then used to infect tobacco, such as Nicotiana tabacum, and the desired polypeptides are recovered from the leaves (Julian K.-C. Ma et al., Eur. J. Immunol. 24, 131-138 (1994)).

The resulting antibodies of this invention may be isolated from the inside or outside (such as the medium) of host cells, and purified as substantially pure and homogenous antibodies. Any standard method for isolating and purifying antibodies may be used, and methods are not limited to any specific method. Antibodies may be isolated and purified by selecting an appropriate combination of, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, recrystallization, and others.

Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). These chromatographies can be carried out using liquid phase chromatographies such as HPLC and FPLC. The present invention also includes antibodies that are highly purified using these purification methods.

In the present invention, the antigen-binding activity of antibodies (Antibodies A Laboratory Manual. Ed Harlow, David Lane, Cold Spring Harbor Laboratory, 1988) can be measured using well known techniques. For example, ELISA (enzyme linked immunosorbent assay), EIA (enzyme immunoassay), RIA (radioimmunoassay), or fluoroimmunoassay may be used.

In the present invention, whether or not the antibodies of this invention induce cell death in non-adhernet cells can be determined from whether cell death is induced in Jurkat cells or ARH77 cells, as in the Examples. Whether or not the antibodies induce cell death in adhesion cells can be determined from whether cell death is induced in HeLa cells, as in the Examples.

Furthermore, the present invention provides cell death-inducing agents or cell growth-suppressing agents which comprise minibodies or 2D7 antibodies of this invention as active ingredients. The cell death-inducing activity of the minibodies or 2D7 antibodies in this invention is considered to have a particularly large effect on activated T cells or B cells, therefore, it is considered to be particularly effective for treatment and prevention of tumors such as cancer (particularly blood tumors), and autoimmune diseases. Accordingly, the present invention provides methods of treatment and prevention of tumors such as cancer (particularly blood tumors), and autoimmune diseases that use the minibodies or 2D7 antibodies of this invention. When using 2D7 antibodies whose molecular weight has not been reduced as active ingredients, they are preferably cross-linked with an anti-IgG antibody and such.

The above-mentioned antibodies can also be used as conjugate antibodies, after linking to various reagents. Examples of such reagents include chemotherapy reagents, radioactive substances, and toxins. Such conjugate antibodies can be produced by known methods (U.S. Pat. No. 5,057,313, and U.S. Pat. No. 5,156,840).

The above-mentioned pharmaceutical agents can be directly administered to patients, or administered as pharmaceutical compositions formulated by known pharmaceutical methods. For example, they may be administered orally, as tablets, capsules, elixirs, or microcapsules, sugar-coated as necessary; or parenterally, in the form of injections of sterile solution or suspensions prepared with water or other pharmaceutically acceptable liquids. For example, they may be formulated by appropriately combining them with pharmaceutically acceptable carriers or media, more specifically, sterilized water or physiological saline solutions, vegetable oils, emulsifiers, suspending agents, surfactants, stabilizers, flavoring agents, excipients, vehicles, preservatives, binding agents, and such, and mixing them at a unit dosage form required for generally accepted pharmaceutical practice. The amount of active ingredient in the formulation is such that appropriate doses within indicated ranges are achieved.

Additives that can be mixed into tablets and capsules include, for example, binding agents such as gelatin, cornstarch, tragacanth gum, and gum arabic; excipients such as crystalline cellulose; swelling agents such as cornstarch, gelatin, alginic acid; lubricants such as magnesium stearate; sweeteners such as sucrose, lactose, or saccharine; and flavoring agents such as peppermint and *Gaultheria adenothrix* oils, or cherry. When the unit dosage form is a capsule, liquid carriers, such as oils and fats, can be further included in the above-indicated materials. Sterile compositions to be injected can be formulated using a vehicle such as distilled water used for injection, according to standard protocols.

Aqueous solutions used for injections include, for example, physiological saline and isotonic solutions comprising glucose or other adjunctive agents such as D-sorbitol, D-mannose, D-mannitol, and sodium chloride. They may also be combined with appropriate solubilizing agents, such as alcohol, and specifically, ethanol, polyalcohol such as propylene glycol or polyethylene glycol, or non-ionic detergent such as polysorbate 80™ or HCO-50, as necessary.

Oil solutions include sesame oils and soybean oils, and can be combined with solubilizing agents such as benzyl benzoate or benzyl alcohol. Injection solutions may also be formulated with buffers, for example, phosphate buffers or sodium acetate buffers; analgesics, for example, procaine hydrochloride; stabilizers, for example, benzyl alcohol or phenol; or anti-oxidants. The prepared injections are typically aliquoted into appropriate ampules.

Administration to patients may be performed, for example by intra-arterial injection, intravenous injection, or subcutaneous injection, alternatively by intranasal, transbronchial, intramuscular, transdermal, or oral administration using methods well known to those skilled in the art. Doses vary depending on the body weight and age of the patient, method of administration and such, nevertheless, those skilled in the art can appropriately select suitable doses. Furthermore, if a compound can be encoded by a DNA, the DNA may be incorporated into a gene therapy vector to carry out gene therapy. Doses and administration methods vary depending on the body weight, age, and symptoms of patients, but, again, they can be appropriately selected by those skilled in the art.

A single dose of a pharmaceutical agent of this invention varies depending on the target of administration, the target organ, symptoms, and administration method. However, an ordinary adult dose (presuming a body weight of 60 kg) in the form of an injection is approximately 0.1 to 1000 mg, preferably approximately 1.0 to 50 mg, and more preferably approximately 1.0 to 20 mg per day, for example.

When administered parenterally, a single dose varies depending on the target of administration, the target organ, symptoms, and administration method, but in the form of an injection, for example, a single dose of approximately 0.01 to 30 mg, preferably approximately 0.1 to 20 mg, and more preferably approximately 0.1 to 10 mg per day may be advantageously administered intravenously to an ordinary adult (presuming a body weight of 60 kg). For other animals, a converted amount based on the amount for a body weight of 60 kg, or a converted amount based on the amount for a body surface area can be administered.

BRIEF DESCRIPTION OF THE DRAWINGS

FIG. 1 shows the adaptors used to produce the pMX2 vector. The bold letters indicate BstXI recognition sequences.

FIG. 5 shows the results of screening using FACS.

FIG. 6 shows the results of screening using FACS.

FIG. 8 is a set of photographs showing cell death induction due to cross-linking of the 2D7 antibody. Each combination of the 2D7 antibody with anti-mouse IgG was made to act on Jurkat cells, and the cell nuclei were stained 48 hours later. Nuclear fragmentation due to cell death was observed when the 2D7 antibody and anti-mouse IgG acted on cells simultaneously.

FIG. 9 shows a 2D7 diabody (2D7DB) sequence.

FIG. 15 shows cell death induction by purified 2D7DB, 48 hours after induction. ARH77 cells (FIG. 15A), Jurkat cells (FIG. 15B), K562 cells (FIG. 15C), and HeLa cells (FIG. 15D) were used.

FIG. 18 shows a time course of cell death induction by 2D7DB (2 μg/ml). Cell death induction was investigated at three through to six hours. ARH77 cells (FIG. 18A) and Jurkat cells (FIG. 18B) were used.

FIG. 21 is a set of photographs showing that cell death due to 2D7DB is not accompanied by DNA fragmentation. The study was performed 24 hours after cell death induction.

FIG. 23 is a set of photographs showing the results of immunostaining to investigate the state of the intracellular actin and nuclei. After reacting ARH77 cells under the conditions described in the figure, actin was detected using anti-actin antibody (red), and cell nuclei were detected using Hoechst 33258 (blue). Actin was absent from cells treated with 2D7DB.

FIG. 26 shows analyses of the action of 2D7DB on PBMC. PHA-M (FIG. 26A), ConA (FIG. 26B), and SAC (FIG. 26C) were used as mitogens. FIG. 26D shows the results in the absence of a mitogen, and FIG. 26E shows the results of a positive control (ARH77). The results shown are, from the top, those of no 2D7DB addition, three-hour addition, and 24-hour addition.

BEST MODE FOR CARRYING OUT THE INVENTION

Figure 2A:
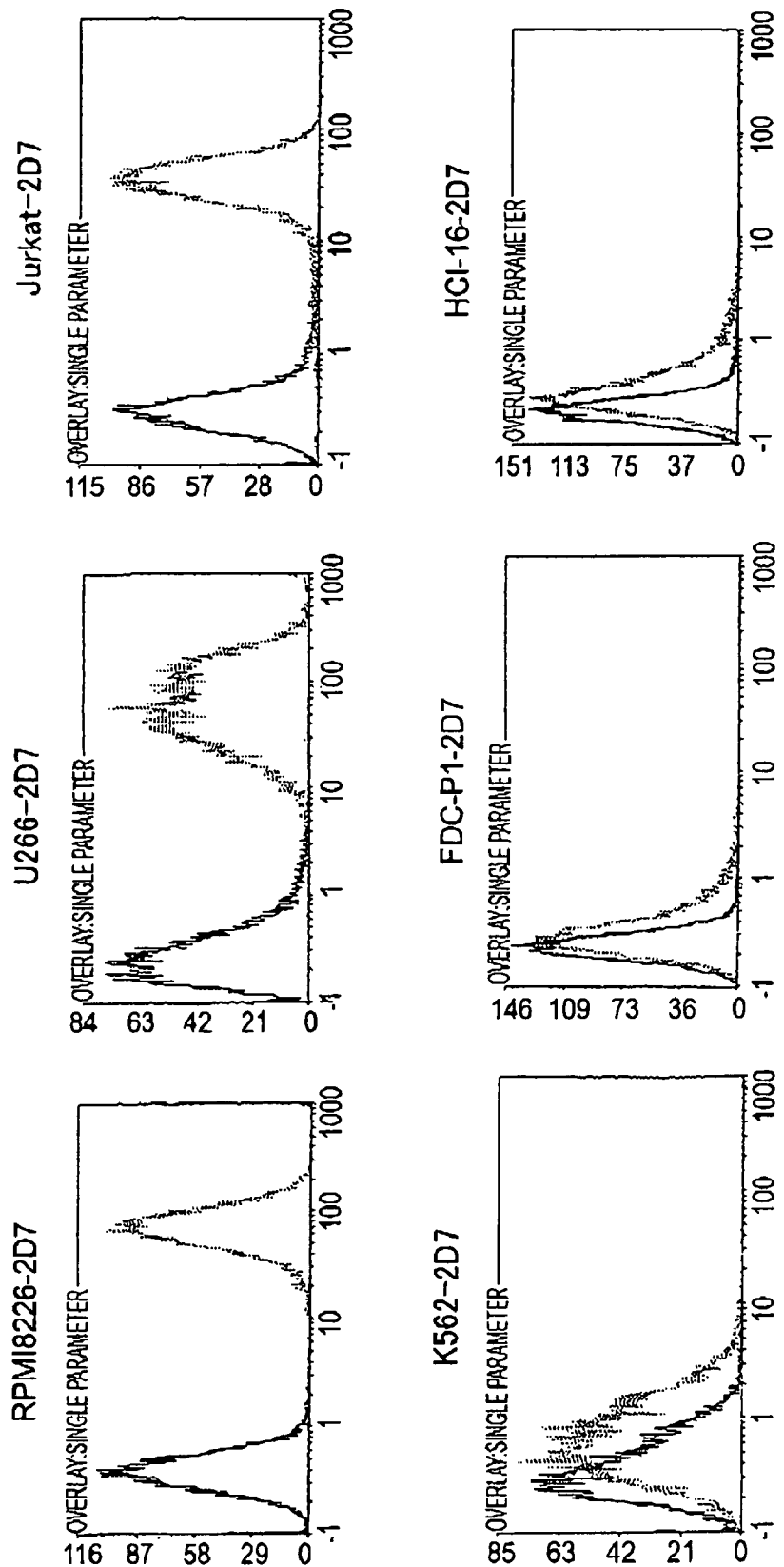
FIG. 2A and FIG. 2B show 2D7 antigen expression in cell lines. Each cell type was stained with 2D7 antibody and their expressions were examined. (Solid line: no primary antibody; dotted line: 2D7 antibody)

Herein below, the present invention is specifically described using Examples; however, it should not to be construed as being limited thereto.

[1] Cell Lines

Human myeloma cell lines (RPMI8226, K562, and ARH77), human T-cell leukemia cell line (Jurkat), FDC-P1, HCI-16, and 2D7 hybridoma cell line (from University of Tokushima) were cultured in RPMI1640 medium (GIBCO 13R) supplemented with 10% fetal calf serum (FCS). Human myeloma cell lines (IL-KM3 and U266) were individually cultured in the same medium supplemented with 2 ng/ml of IL-16 (R & D), and Ba/F3 was cultured in the same medium supplemented with 2 ng/ml of IL-3 (R & D). COS7, 293T, HeLa, NIH3T3, and BOSC23 were cultured in DMEM medium (GIBCO BRL) supplemented with 10% FCS, and CHO was cultured in α-MEM medium (GIBCO BRL) supplemented with 5% FCS or 10% FCS.

[2] Production of pMX2 Vectors

The GFP gene region of the retrovirus vector, pMX-GFP, which packages the GFP gene in the virus particle, was cut out and removed using EcoRI-SalI. The adaptor, which comprised a BstXI site in its sequence (FIG. 1) (and was synthesized with an ABI DNA synthesizer, then annealed in vitro before use), was inserted into this region, forming pMX2.

(3) Production of cDNA Libraries

Total RNA was purified from RPMI8226 cells by standard methods using Trisol (GIBCO BRL). Furthermore, the mRNAs were purified from 200 μg of this total RNA, using a μMACS mRNA Isolation kit (Miltenyi Biotec) according to the manufacturer's instructions. The cDNAs were synthesized using random hexamers (SuperScript Choice System for cDNA Synthesis; Invitrogen) with 3.6 μg of mRNA as template, and then a BstXI adaptor (Invitrogen) was linked to both ends. This cDNA was inserted into a pMX2 vector cleaved with BstXI, and was introduced into ELECTRO MAX DH10B (GIBCO BRL) by electroporation (2.5 KV, 200 Ω, 25 μF). After adding 1 ml of SOC, the vectors were then incubated at 37° C. for one hour, 1 ml of 40% glycerol/LB+Amp was added. A portion of the culture was used to check the titer and the remainder was stored at −80° C. The obtained library was plated at 200 μl/well (7% DMSO/LB+Amp) into two 96-well plates, so that each well contained 1000 clones. These were cultured overnight at 37° C. Four wells (4000 clones) from this plate were combined and placed into an ampicillin-containing LB medium (4 ml). This was defined as one pool, the rest of the wells were treated similarly. Ultimately, 24 pools were prepared from a single plate. After incubating each pool overnight at 37° C., DNAs were prepared (QIAGEN) and used for transfection into packaging cells. The plates used for inoculation were stored at −80° C. until used for secondary screening.

[4] Purification of Antibodies 0.5 ml of ascites, sent from University of Tokushima, was adsorbed to a Protein A Hi Trap Affinity column (Amersham Pharmacia). The IgG fraction was then eluted using 0.1 M sodium citrate, pH3.0, and the 2D7 antibody was collected. This was concentrated using Centricon (YM-10; Millipore), and the buffer was exchanged to PBS to ultimately yield a total of 5.34 mg of antibody. This was separated into aliquots and stored at −20° C. (concentration: 0.89 μg/μL).

[5] FACS

Adherent cells were detached using 1 mM EDTA/PBS, and non-adherent cells were collected by centrifugation, then suspended in FACS buffer (2.5% FCS, 0.02% NaN$_3$/PBS). These cells were left to stand on ice for one hour in a buffer (5% FCS/PBS) containing 2D7 antibody (final concentration 10 μg/ml). These were then washed with FACS buffer, reacted in a solution of FITC-anti-mouse IgG (Immunotech) (1:150, 50 μL FACS buffer) on ice for 30 minutes, washed twice with FACS buffer, and then analyzed using EPICS ELITE (COULTER).

[6] Retrovirus Infection (i) Retrovirus Packaging

The day before transfection, 2 ml of BOSC23 cells, which are retrovirus-packaging cells, were plated onto a 6-well plate at $6\times10^5$ cells/well. Transfection was carried out by the following procedure: 1 μg of the plasmid DNA derived from each pool was mixed with 3 μL of FuGENE 6 Transfection Reagent (Roche), left to stand at room temperature for 20 minutes, and then added to the BOSC23 cell culture medium plated the day before. Cells were then cultured at 37° C. for 48 hours, and the culture medium was collected. Dead cells were removed by solution.

(ii) Virus Infection

The 2 ml of NIH3T3 cells plated onto 6-well plates at $1\times10^5$ cells/well the day before were cultured for 24 hours in 1 ml of virus solution supplemented with 10 μg/ml of polybrene (hexadimethrine bromide; Sigma). 1.5 ml of fresh medium was then added, the cells were cultured for another 48 hours, and gene expression was then analyzed using FACS.

[7] Immunoprecipitation

Cells were lysed in a lysis buffer (0.5% Nonidet P-40, 10 mM Tris, pH 7.6, 150 mM NaCl, 5 mM EDTA, 1 mM phenylmethylsulfonyl fluoride, 5 μg/ml apron), and the resulting solution was centrifuged to remove the insoluble proteins and obtain a cell lysate. 1 μg of 2D7 antibody was added, and incubated at 4° C. for four hours. Magnetic protein G (BioMag) was then added, and this was incubated for another one hour. Subsequently, the immunoconjugate was washed three times with a lysis buffer, and then subjected to SDS-PAGE. This gel was silver stained (Daiichi Pure Chemicals) according to the attached instructions. On the other hand, for peptide sequencing, the gel on which SDS-PAGE was performed was transferred to ProBlott (Applied Biosystems), and this was stained for one minute with Coomassie blue staining solution (0.1% coomassie blue R-50 in 40% MetOH/1% acetic acid). After washing several times with 50% MetOH, the baud of interest was cut out, washed five times with 1 ml of DDW, dried in vacuo, and then subjected to peptide sequencing.

[8] Cell Growth Assay Using the 2D7 Antibody

Each type of cell was plated into a 96-well plate at $1\times10^6$ cells/ml in the presence or absence of PMA (50 ng/ml; GIBCO BRL) and PHA (10 μl/ml; GIBCO BRL). After subsequent addition (10 μg/ml) or no addition of the 2D7 antibody, this was cultured for 48 hours. After culturing, morphological changes in the cells were observed under a microscope. Viable cell count was determined by adding WST-8 (viable cell count reagent SF; Nacalai Tesque), culturing at 37° C. for two hours, and measuring $OD_{450}$ to measure the relative viable cell count.

[9] Induction of Cell Death by Cross-Linking

Jurkat cells were plated on a 24-well plate at $8\times10^5$ cells/well, and 10 μg/ml of anti-mouse IgG (Fc) antibody (Cappel) was further added in the presence (5 μg/ml) or absence of 2D7 antibody. 48 hours later, the cells were collected, and after washing with PBS, methanol was added to a concentration of 70%, and this was left to stand at −20° C. for 15 minutes. After washing the cells with FACS buffer several times, Hoechst 33258 was added at a concentration of 10 μg/ml and this was incubated at room temperature for 30 minutes. The cells were washed again with FACS Buffer, and then placed on a slide glass as a droplet to observe the state of the nuclei under a fluorescence microscope.

[10] Cloning of the 2D7 Variable Region

Total RNA was purified from 2D7 hybridoma (provided from University of Tokushima) using Trizol according to standard methods. Using 3 μg of this RNA as a template, cDNAs were synthesized using a SMART RACE cDNA Amplification kit (CLONTECH), according to the attached instructions. Using this cDNA as a template, the variable regions of the heavy chain and light chain were amplified by PCR using the following primers:

```
                                    (SEQ ID NO: 9)
Heavy chain:   5'-CAGGGGCCAGTGGATAGACTGATG (SEQ ID NO: 10)
Light chain:   5'-GCTCACTGGATGGTGGGAAGATG
```

The amplified cDNAs encoding each of variable regions were subcloned into pCR-TOPO vector (Invitrogen), and the nucleotide sequences (SEQ ID NOs: 1 and 3) were determined.

[11] Production of 2D7 Diabody Expression Vector

Plasmids, to which each of the variable region cDNAs were subcloned, were used as templates, and the variable regions of the heavy chain and light chain (VH and VL) were respective amplified using the primers below:

```
Heavy chain
2D7DB-H1:
                                    (SEQ ID NO: 11)
5'-CCTGAATTCCACCATGCGATGGAGCTGGATCTTTC 2D7DB-H2:
                                    (SEQ ID NO: 12)
5'-AATTTGGCTACCGCCTCCACCTGAGGAGACTGTGAGAGTGGTGCCCT Light chain
2D7DB-L1:
                                    (SEQ ID NO: 13)
5'-TCCTCAGGTGGAGGCGGTAGCCAAATTGTTCTCACCCAGTCGCCAGC 2D7DB-L2:
                                    (SEQ ID NO: 14)
5'-ATTGCGGCCGCTTATCACTTATCGTCGTCATCCTTGTAGTCTTTTAT
CTCCAACTTTGTCCCCGAGCC
```

Each of the VH and VL cDNAs amplified by these primers were combined into one tube, and further subjected to PCR. Using the PCR products as templates, PCR was performed again, this time using 2D7DB-H1 and 2D7DB-L2 as primers, to synthesize cDNA with VH and VL linked through a 5-mer linker (SEQ ID NO: 5). This cDNA was digested with EcoRI-NotI and inserted into the EcoRI-NotI gap of the animal cell expression vector, pCXND3. The nucleotide sequence was confirmed, completing the construction of the 2D7 diabody expression vector, pCXND3-2D7DB.

[12] Transient Expression in COS7 Cells

2 μg of pCXND3-2D7DB, or of at empty vector used as a control, was mixed with 6 μL of transfection reagent (LT-1, MIRUS) according to the attached instructions, and this was added to COS7 cells (plated the day before into a 6-well plate at $1\times10^5$ cells/well) whose medium had been exchanged to a serum-free medium (OPTI-MEM, GIBCO BRL). Five hours later, 200 μL of serum was added, and this was cultured for two to three days. The medium was collected, and dead cells were removed by centrifugation. The culture supernatant was then used for an experiment to detect cytotoxic activity.

Expression of 2D7DB in the culture supernatant was confirmed by Western blotting. More specifically, equal amounts of 2×SDS-PAGE Sample buffer and culture supernatant were added. In addition, after lysing the cells by adding a lysis buffer (0.5% Nonidet P-40, 10 mM Tris, pH 7.6, 150 mM NaCl, 5 mM EDTA), insolubilized proteins were removed by centrifugation to prepare a cell lysate, and an equal amount of 2×SDS-PAGE Sample buffer was added to this. After performing SDS-PAGE on each sample, the gels were transferred to PVDF membranes, and expression of the 2D7 single chain was detected using anti-FLAG antibody.

[13] Establishment of Expression Cell Lines Producing 2D7 Diabody

20 μg of pCD3-2D7DB, linearized by cleaving with PvuI, was introduced to CHO cells (DXB11 strain) by electroporation, as described below.

After washing the CHO cells twice with ice-cold PBS, they were suspended in PBS at $1\times10^7$ cells/l. 20 μg of the above-mentioned plasmid was mixed into these cells, and this was electropulsed (1.5 KV, 25 μFD). The cells were diluted in to appropriate fractions, plated on to a 10 cm dish, and cultured in the presence of G418 (GIBCO BRL) at a final concentration of 50 μg/ml. Approximately 30 clones were selected from the grown colonies, and the diabody expression levels in the culture supernatants were investigated by Western blotting. The clone with the highest expression level was expanded in a nucleic acid-free MEMO medium containing 5 nM MTX, and this was stocked as an overproducing cell line.

[14] Large-Scale Purification of 2D7 Diabodies

A subconfluent 2D7DB-producing CHO cell line in a T-125 flask was detached using Trypsin-EDTA, and then this was transferred to a roller bottle (250 ml of MEMC without nucleotide +5% FCS). Four days later, the culture solution was removed, and the cells were washed twice with PBS. The medium was then exchanged to 250 ml of CHO-S-SFMII medium (GIBCO BRL) to produce a serum-free medium, cells were cultured for three days, and then the cell culture supernatant was collected. After removing the dead cells by centrifugation, this was filtered and used for purification Purification of single chain Fv was performed as follows: First, the collected culture supernatant was applied and adsorbed onto an anti-Flag M2 column. After washing with buffer A (50 mM Tris-HCl pH7.4, 150 mM NaCl, 0.0% Tween 20), single chain Fv was eluted with buffer B (100 mM Glycine pH3.5, 0.01% Tween 20). The collected sample was immediately neutralized with Tris-HCl pH8.0 so that the final concentration was 25 mM. This was then used for gel filtration purification by a Superdex 200HR (26/60) column. The dimer fraction of single chain Fv was collected in PBS containing 0.01% Tween 20. A portion of the collected sample was subjected to SDS electrophoresis and silver staining to confirm that the protein of interest has been purified, and then this was concentrated to produce a purified authentic sample of 2D7 diabody.

[15] Cell Death Induction Experiment Using 2D7 Diabody

Various white blood cell lines were plated into 24-well plates at $2\text{-}5\times10^5$ cells/well. Purified 2D7DB, or the culture supernatant of COS7 transiently expressing 2D7DB, was added and cell death was induced. When used, the culture supernatant of COS7 transiently expressing 2D7DB was added so its concentration was 50%. The amount of medium in each well was 0.8 to 1 ml/well. When stimulating Jurkat cells, Con A (WAKO) was added at the time of 2D7DB addition to a final concentration of 2 μg/ml.

Adherent cells (HeLa) were plated into a 6-well plate at $2\times10^5$ cells/well, and the cells were attached by culturing overnight. Subsequently, purified 2D7DB was added to the culture solution.

Several hours to several days after 2D7DB addition, the non-adherent cells were collected as they were, and adherent cells were collected after detaching the cells with 1 mM EDTA/PBS. The cells were then washed with ice-cold PBS, and labeled with Annexin V, which is an apoptosis marker, and with PI, which is a dead-cell marker, according to the attached instructions (TACS Annexin V-FITC Apoptosis Detection Kit, TREVIGEN Instructions). The proportion of stained cells was then measured using flow cytometry (EPICS ELITE, COULTER).

[16] Cell Death Induction by Actinomycin D

Various hemocyte cell lines were plated into 24-well plates at $2\text{-}5\times10^5$ cells/well. To inhibit the initial stage of apoptosis, a caspase inhibitor (Z-VAD-FMK, Promega) was added at a final concentration of 50 μKM, and after incubating for 2.5 hours, cell death was induced. For cell death induction by Actinomycin D, Actinomycin D (Sigma) was added at 1 μg/ml (Jurkat) or 5 μg/ml (ARH77), and for cell death induction by 2D7DB, 2 μg/ml of purified 2D7DB was added. Cells were collected 16 hours after cell death induction, and stained using Annexin V and PI.

[17] Cell Growth Assay Using 2D7 Diabody

Each type of cells was plated into a 96-well plate at a cell concentration of $1\text{-}2\times10^4$ cells/well. 2D7DB was added at an appropriate concentration, and the cell count was determined after three days of culturing. Viable cell count was determined using WST-8. More specifically, this reagent was added to the cells at 10 μl/well, and the cells were then cultured at 37° C. for 1.5 hours, The relative viable cell count was determined by measuring the $OD_{450}$ using a spectrophotometer. The growth suppression rate was calculated from $(1-(OD_{450}$ of 2D7DB treated cells/$OD_{450}$ of 2D7DB untreated cells))×100.

[18] Detection of DNA Fragmentation

ARH77 and Jurkat cells were plated into a 6-well plate so that the cell concentration was $2\times10^6$ cells/well, and cell death was induced by adding purified 2D7DB at a fit concentration of 2 μg/ml, or Actinomycin D at a final concentration of 1 μg/ml (ARH77) or 5 μg/ml (Jurkat) to each well. The control was a well to which nothing was added. After culturing for 24 hours, the cells were collected, washed once with PBS, and then lysed in a lysis buffer (10 mM Tris pH7.5, 10 mM EDTA, 0.5% Triton X-100). This was followed by centrifugation to remove the insoluble proteins, and then the material was treated with RNase A and Proteinase K. A portion of this was then subjected to agarose gel electrophoresis to detect chromatin DNA fragmentation.

[19] Inhibition of Cell Death Induction by Cytochalasin D

ARH77 cells were plated into a 24-well plate to achieve a cell concentration of $5\times10^5$ cells/well, and cytochalasin D (Sigma) was added to a final concentration of 20 μg/ml. The control was a well to which ethanol alone was added. After culturing for one hour, purified 2D7DB was added at various concentrations (0, 200, 500, 1000 ng/ml), and culturing was continued for another four hours. Cells were then collected, and the proportion of dead cells was detected by staining with PI.

[20] Immunostaining of 2D7DB-Treated Cells Using Anti-Actin Antibody

2D7DB was added at a concentration of 1 μg/ml to cytochalasin D-treated/-untreated ARH77 cells, and after culturing at 37° C. for 15 minutes, the cells were adhered to a slide glass with Cytospin. After immobilizing the cells by immersion in methanol for 15 minutes at −20° C., blocking was performed using a blocking buffer (3% BSA/PBS) at 4° C. for one hour. This was then reacted with CY3-labeled anti-actin antibody (Sigma) diluted 100-fold in 1% BSA/PBS for one hour at room temperature, and then the cell nuclei were stained with Hoechst 33258. After washing several times with PBS, the cells were observed under a confocal laser scanning microscope (Olympus).

EXAMPLE 1

Expression Analysis of 2D7 Antigen in Each Type of Cell Line

Figure 2B:
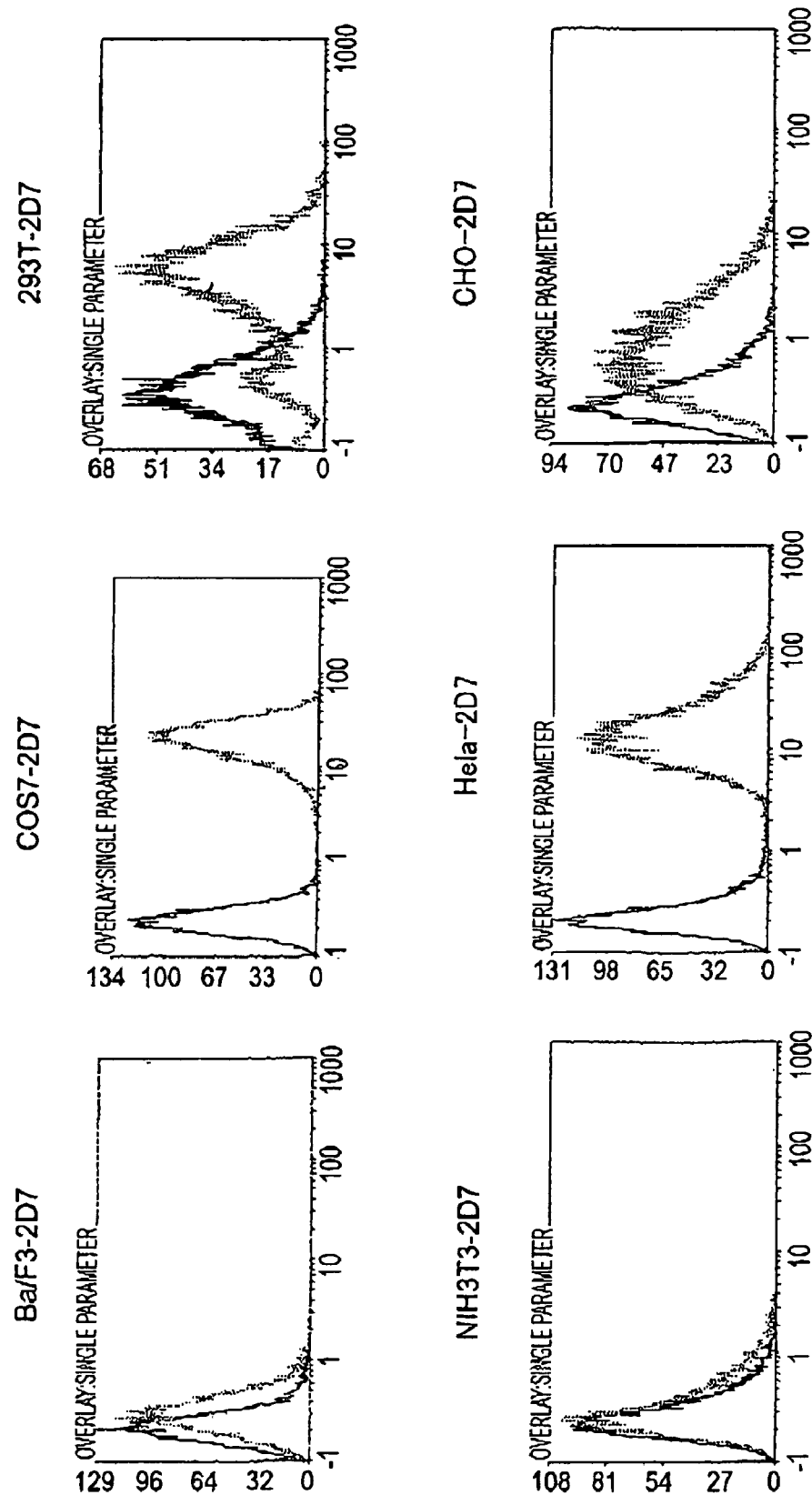

To determine the cell line that should become the source to produce a cDNA expression library and the cell line that should become the host, 2D7 antigen expression in each type of animal cell was analyzed using FACS (FIG. 2A and FIG. 2B). As a result, among human-derived white blood cells, extremely strong expression of the 2D7 antigen was observed in lymphocytic tumor cell lines, RPMI8226, U266, and in Jurkat, but expression was found to be weak in K562. In Ba/F3, FDC-P1, and HCI-16, which are white blood cells derived from mice, expression was very weak, perhaps due to differences between the species. Of the adherent cells, expression was observed in COS7, 293T, and HeLa Expression was hardly observed in mouse NIH3T3 cells.

From the expression patterns mentioned above, RPMI8226 cells were judged to be appropriate as a source of a cDNA library to be used for expression cloning, and NIH3T3 cells were determined to be appropriate as host cells to be used for screening, to which the expression library is transferred.

EXAMPLE 2

Cloning of 2D7 Antigen

[1] Cloning from a Protein

Figure 3:
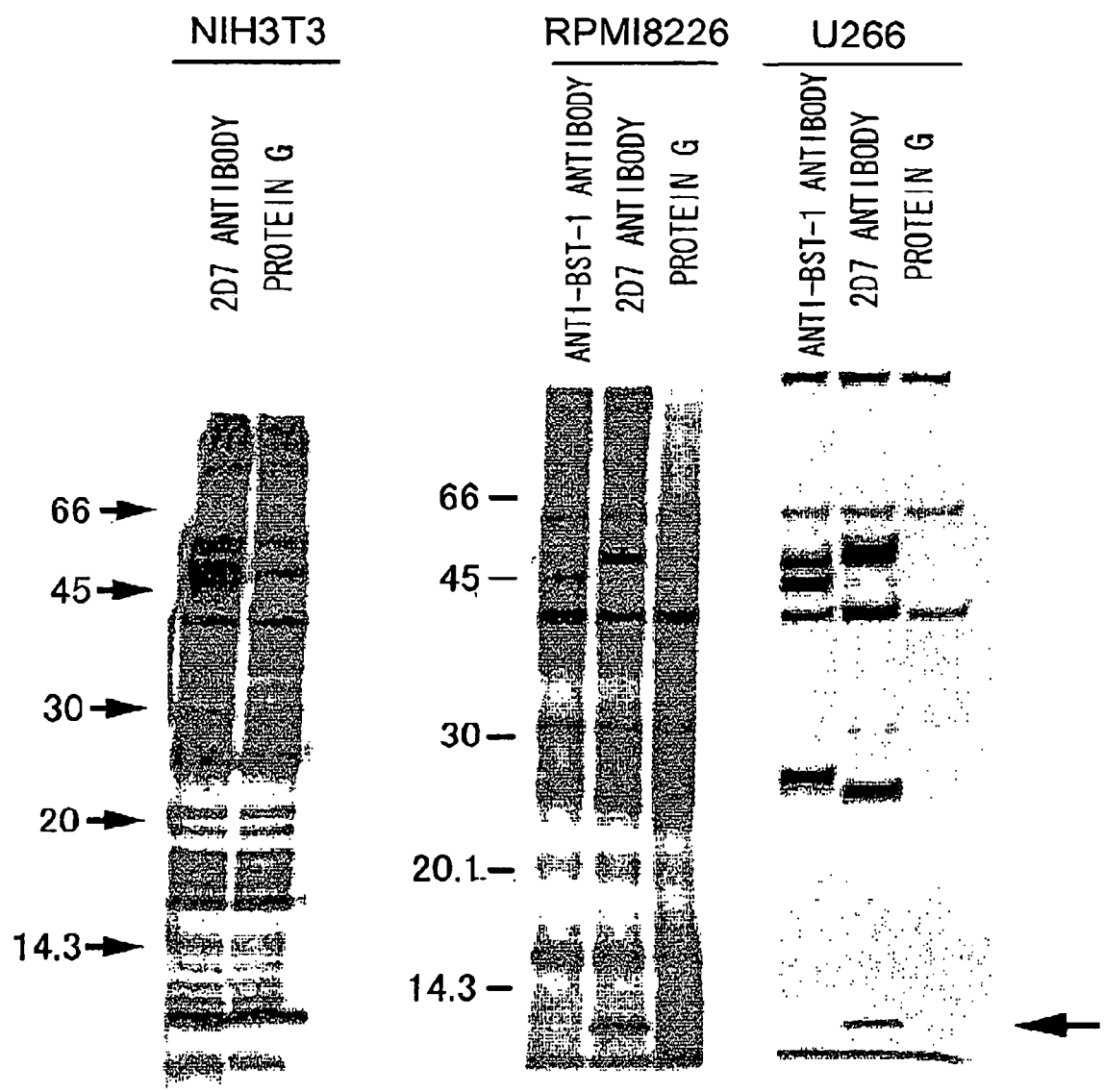
FIG. 3 is a set of photographs showing the results of immunoprecipitation using the 2D7 antibody. NIH3T3, RPMI8226, and U266 cells were solubilized, immunoprecipitation was performed with the 2D7 antibody, anti-BST-1 antibody (control), or protein G itself, and the proteins were detected by silver staining. In RPMI8226 and U266, a molecule of approximately 12 KD (arrow), which is specifically precipitated by the 2D7 antibody, is detected. This band was cut out and peptide sequenced, and thus found to be P2-microglobulin.

Cell lysates were prepared from RPMI8226 cells and U266 cells, which express the 2D7 antigen, and NIH3T3 cells, which do not express the 2D7 antigen, and immunoprecipitation was performed using the 2D7 antibody. As a result, a molecule (approximately 12 kD) that precipitates specifically in RPMI8226 and U266 cells was observed (FIG. 3). This molecule was not detected by Western blotting using the 2D7 antibody, but since it is at least reproducibly precipitated by the 2D7 antibody, it was strongly predicted to be the 2D7 antigen itself, or a molecule that co-precipitates with the 2D7 antigen.

Coomassie staining was performed on this band; it was then cut out and the peptides were sequenced. As a result, this 12 kD molecule was identified as β2 microglobulin (β2M). Since β2M is one of the class I MHC protein complexes that associate with HLA class I through non-covalent bonds, the 2D7 antibody is considered to have co-precipitated it as an HLA complex. HLA class I comprises the α1 and α2 domains required for antigen presentation, and the α3 domain which binds to β2M. Since the 2D7 antibody can co-precipitate the β2M molecule, it is anticipated that the 2D7 antibody will recognize the α1-α2 domains of HLA class I as an epitope.

[2] Expression Cloning of Genes cDNAs were synthesized using random hexamers from mRNAs purified from the 2D7 antigen-expressing cells, RPMI8226. These were inserted into a retrovirus vector, pMX2, and a retrovirus expression library was constructed. The library titer was investigated, and found to include a total of $6 \times 10^6$ clones. Furthermore, the average cDNA length was found to be approximately 1.5 kb, arrived at by randomly selecting 24 clones from this library and investigating their insert size using colony PCR. Thus, the produced expression library was judged to be sufficient for use in expression cloning.

Figure 4A:
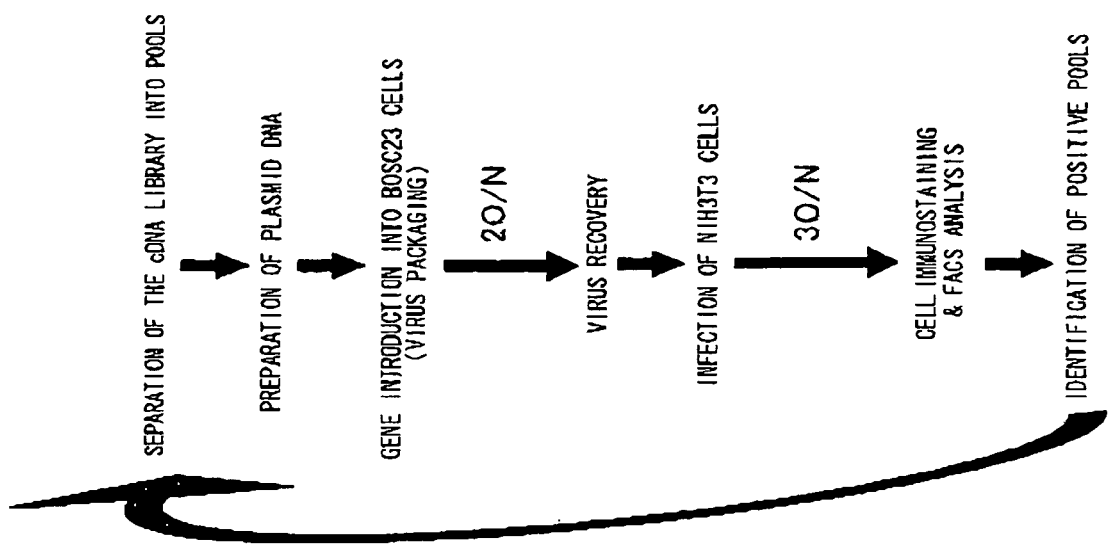
FIG. 4 shows flow diagrams for screening. Separation into pools, preparation of DNA, packaging into virus, infection of 3T3 cells, and screening using FACS were performed in one span (FIG. 4A). By the end of the fourth screening, the library was narrowed down to approximately 20 clones. In the fifth screening, 64 colonies were individually inoculated into a 96-well plate, pools were formed using the vertical and horizontal rows, and then screened. As a result, the library was narrowed down to twelve candidate clones (FIG. 4B).
Figure 4B:
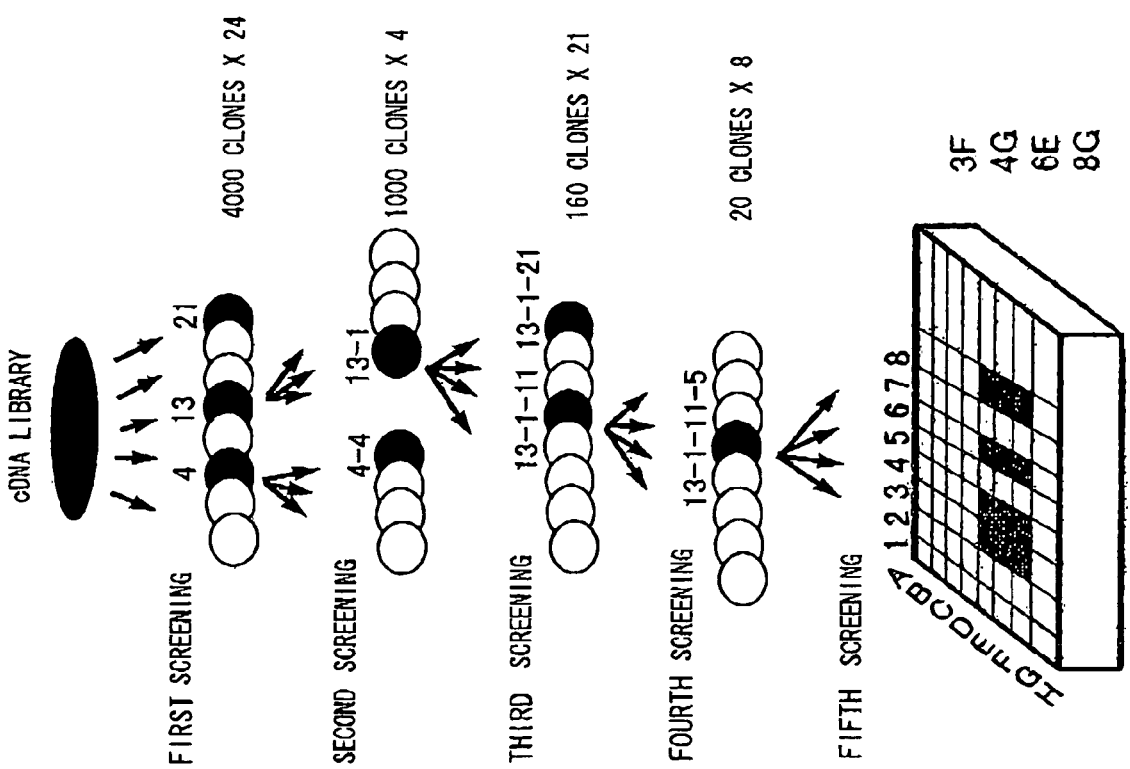

FIG. 4A and FIG. 4B show a flow diagram of the screening described below. In the first screening, 4000 independent clones were used in one pool, and 24 pools (corresponding to 96000 clones) were produced. The plasmids were packaged into retroviruses by transfecting each plasmid into BOSC23 cells. The resulting viruses derived from each pool were infected into NIH3T3 cells. Three days after infection, the cells were detached, and after staining with 2D7 antibody, expression analysis was performed using FACS. As a result, compared to NIH3T3 cells infected with viruses derived from an empty vector (control), 2D7-positive cells were found in 3 of the 24 pools (pools 4, 13, and 21).

Figure 5A:
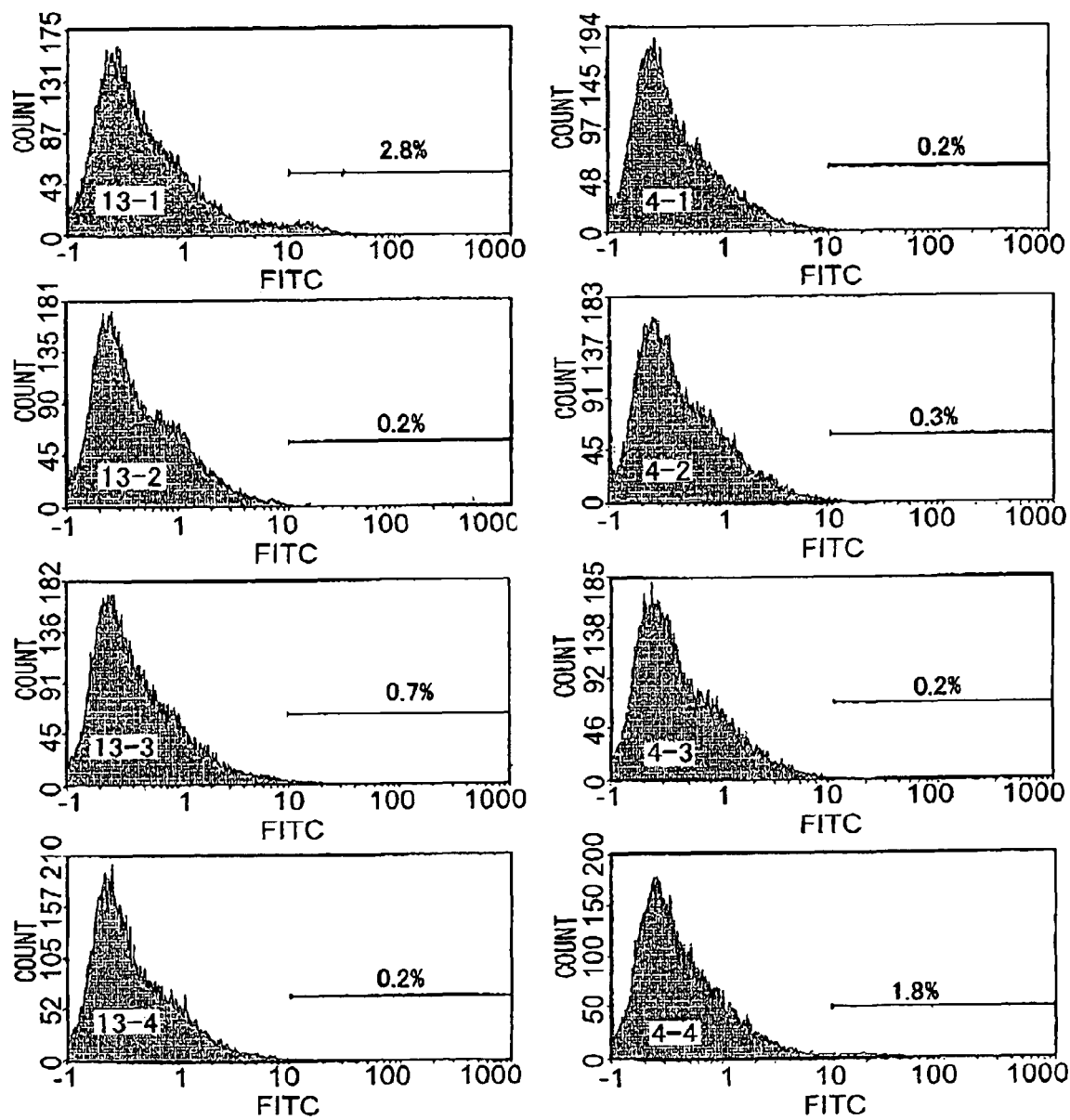
FIG. 5A shows the results of the second screening.
Figure 5B:
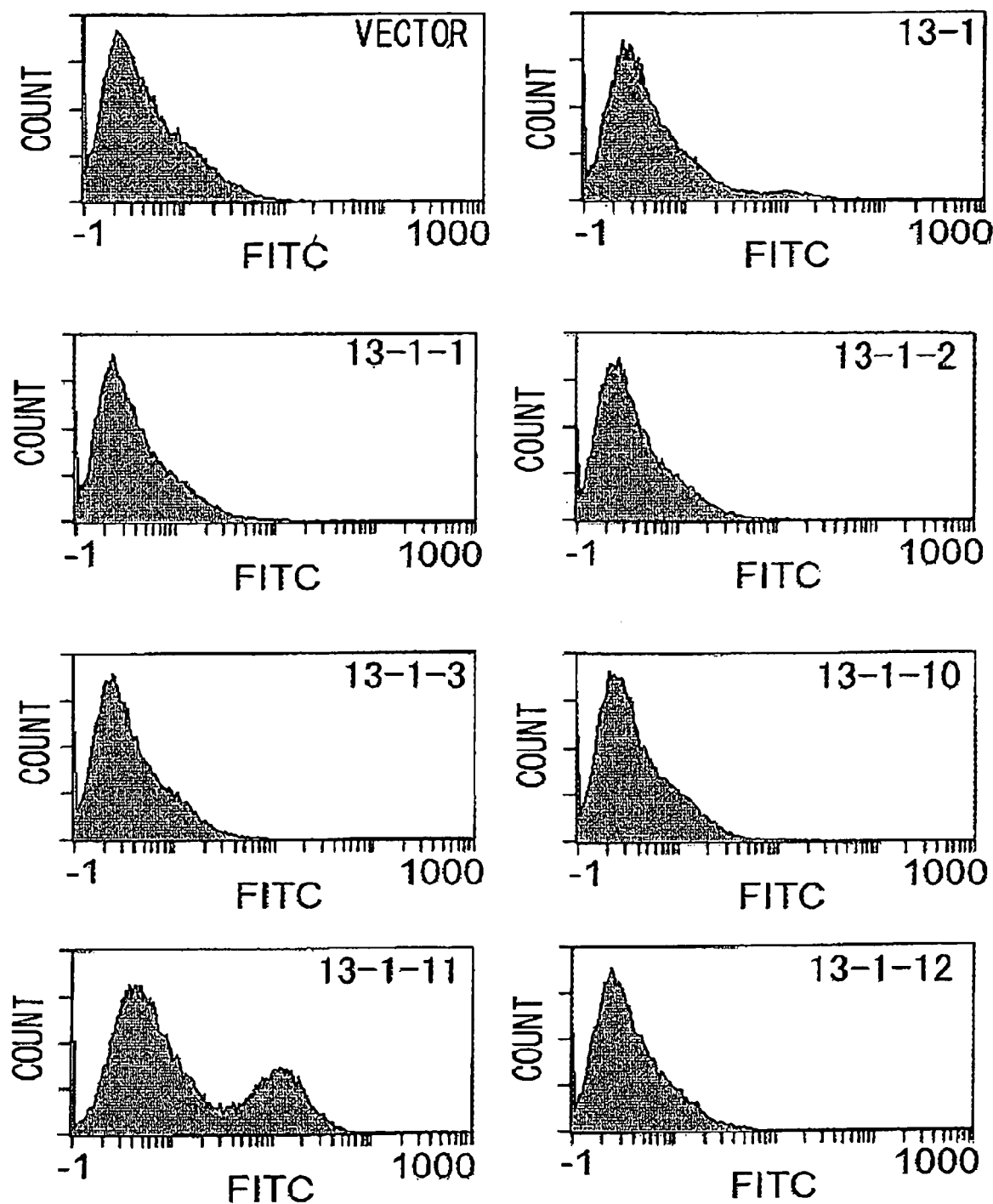
FIG. 5B shows the results of the third screening.
Figure 5C:
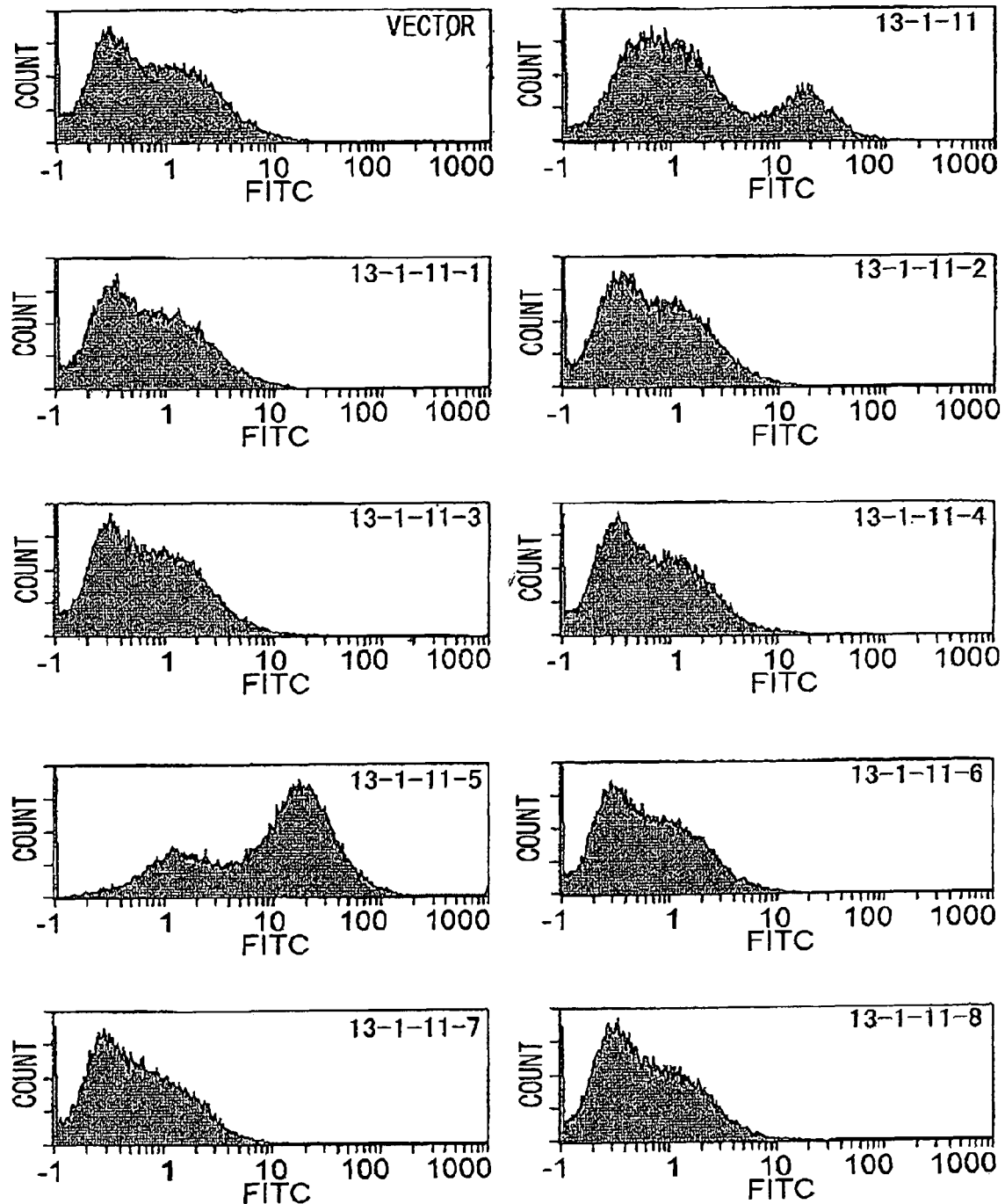
FIG. 5C shows the results of the fourth screening. NIH3T3 cells were infected with retroviruses prepared from each pool, and three days later the cells were stained with the 2D7 antibody. The clones were narrowed down by gradually reducing the pool size of each screening.

Next, pools 4 and 13, which showed positive results in the first screening, were divided into four pools each comprising 1000 independent clones, and a second screening was performed. As a result, a single clearly positive pool was found from each pool (FIG. 5A, pool 4-4, and pool 13-1). Pool 13-1 was further divided into 21 pools, each comprising 160 independent clones, to perform a third screening. Two positive pools (FIG. 5B, 13-1-11 and 13-1-21) were identified. Subsequently, pool 13-1-11 was divided into eight pools, each comprising 20 clones, to perform a fourth screening, and a positive pool (FIG. 5C, 13-1-11-5) was obtained.

Figure 6A:
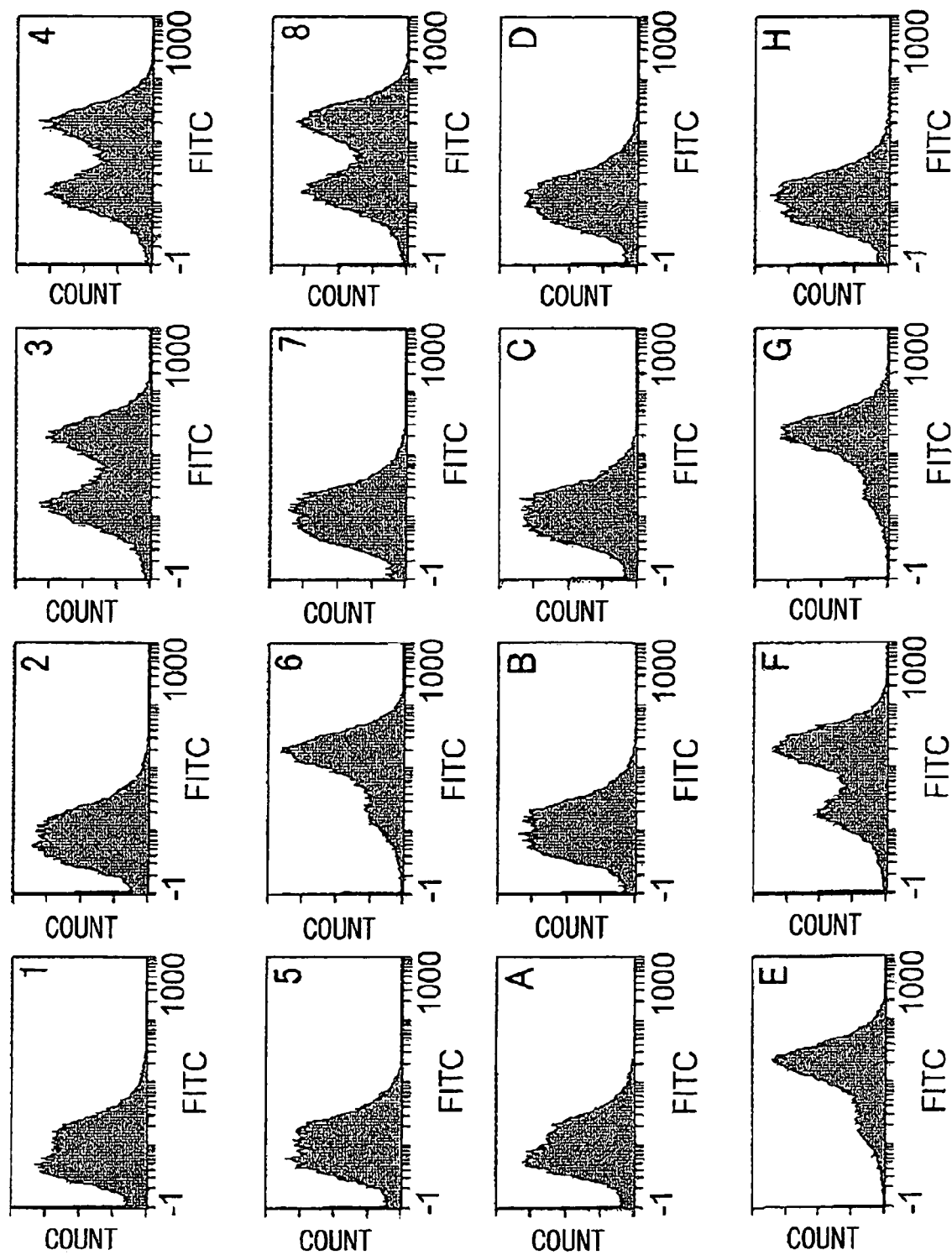
FIG. 6A shows the results of the fifth screening.
Figure 6B:
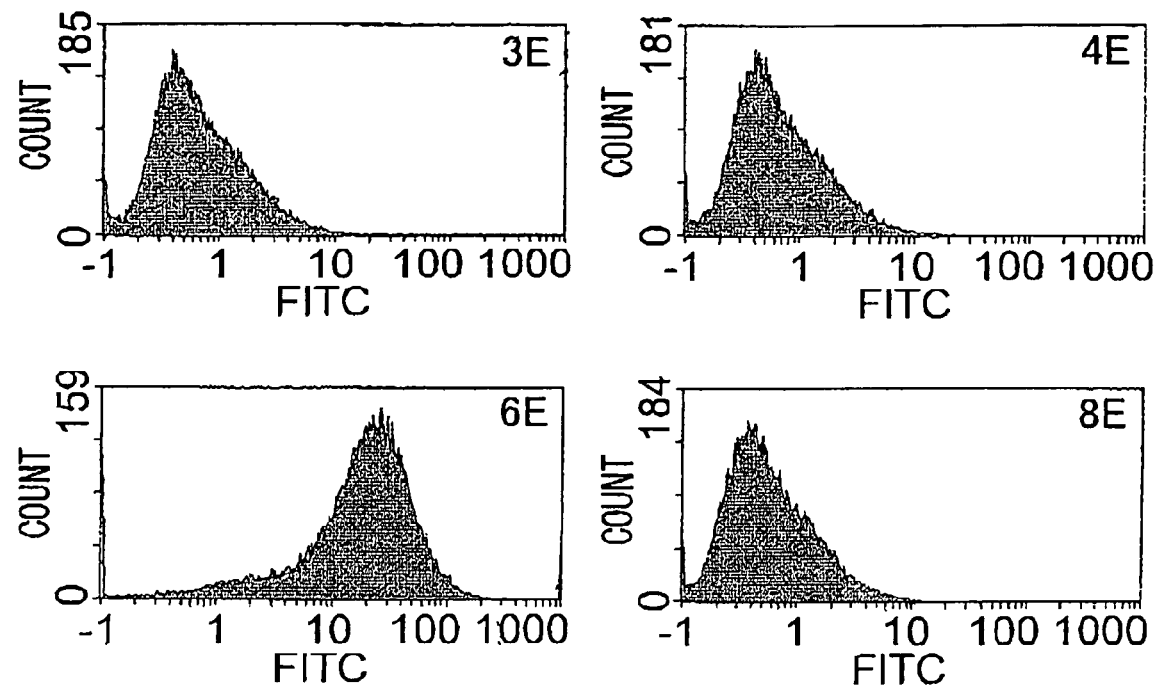
FIG. 6B shows the result of the final screening. As a result of the fifth screening, positive clones were found in rows 3, 4, 6, and 8, and in rows E, F, and G. As a result of screening the twelve candidate clones, positive clones were found in row E at 6E. When the nucleotide sequence of this 6E was analyzed, it was found to encode HLA class I A*6802.

This pool was spread onto an LB plate, 64 colonies were picked one by one, and each of these were inoculated to one well of a 96-well plate. The eight clones in the vertical rows were taken as one pool to produce eight pools (1 to 8), and the eight clones in the horizontal rows were taken as one pool to produce eight pools (A to H), and a fifth screening was performed. As a result, pools 3, 4, 6, and 8, and pools E, F, and G were positive, thus narrowing down the positive candidate clones to twelve clones (FIG. 6A). FACS was performed on these twelve clones, and ultimately four positive clones (3F, 4G, 6E, and 8G) were identified as a single clone recognized by the 2D7 antibody (FIG. 6B).

As a result of reading the sequence of the insert portion of these clones, all four clones were found to be the full-length cDNA sequence of Human MHC class I HLA-A-6802.

HLA-A is classified into several dozen types of haplotypes. As a result of this cloning, the A*6802 haplotype of HLA class I was identified as a 2D7 antigen, but since the 2D7 antibody recognizes a wide variety of cells, the haplotype of HLA class I in the RPMI8226 cells that were used as the gene source just happened to be A*6802, and the 2D7 antibody was considered to be an antibody that recognizes any haplotype of HLA class I molecules.

EXAMPLE 3

Examination of Growth Inhibitory Effect

Several types of leukemia cell lines (K562, Jurkat, and RPMI8226) were used to investigate whether the 2D7 antibody has a cytocidal effect. The expression level of the 2D7 antigen in the three cell lines is: K562, weakly positive; Jurkat and RPMI8226, strongly positive.

Figure 7A:
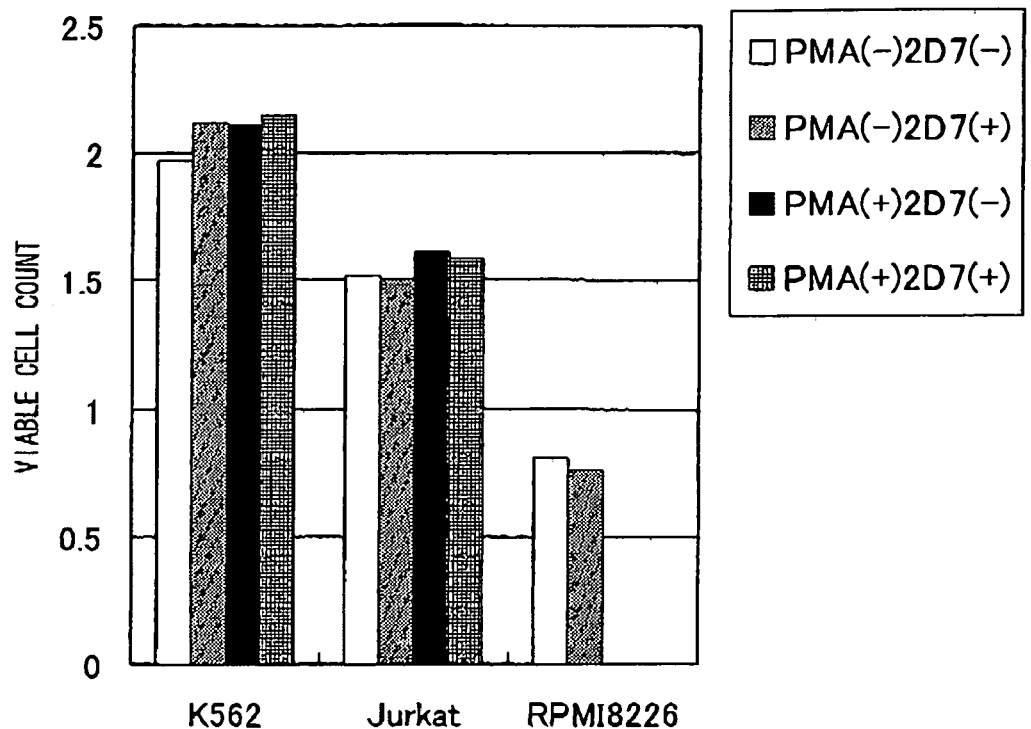
FIG. 7 is a graph and a set of photographs showing the influence on cells of the addition of 2D7 antibody. 2D7 antibody (10 µg/ml) was added, and the number of viable cells was determined 48 hours later. Hardly any change in cell growth was observed, even after 2D7 antibody was added (FIG. 7A). K562 cells (FIG. 7B), Jurkat cells (FIG. 7C), and RPMI8226 cells (FIG. 7D) were each observed 24 hours after antibody addition. The 2D7 antibody induced aggregation of Jurkat cells.
Figure 7B:
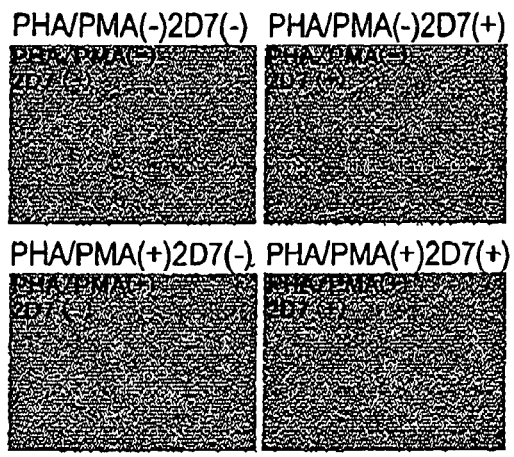
Figure 7C:
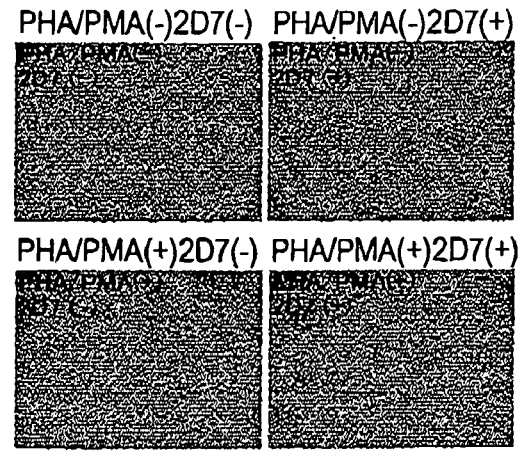

K562 and Jurkat cells were plated in the presence or absence of PHA and PMA, and 10 μg/ml of the 2D7 antibody was added thereto. On observing the cells 24 hours later, weakly 2D7-positive K562 cells did not show obvious differences in their morphology due to the presence or absence of the 2D7 antibody, however, addition of 2D7 antibody resulted in significant cell aggregation in Jurkat cells strongly expressing 2D7 (FIG. 7B and FIG. 7C). However, growth inhibition due to addition of the 2D7 antibody was not observed (FIG. 7A). Growth inhibition due to 2D7 in Jurkat cells activated by PHA and PMA stimulation was also not observed.

Figure 7D:
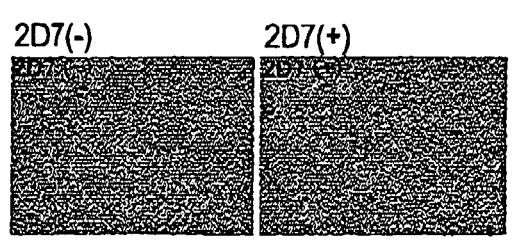

Unexpectedly, addition of 2D7 antibody did not have an obvious effect on the morphology and growth of the strongly 2D7-positive RPMI8226 cells (FIG. 7D).

Next, it was examined whether cytocidal effects can be observed by adding anti-mouse IgG(Fc) antibody to 2D7 antibody, to cross-link the antibodies. Anti-mouse IgG was added to Jurkat cells, in the presence or absence of 2D7 antibody. The cells were cultured, and 48 hours later the cell nuclei were stained with Hoechst 33258. Cells were observed for fragmentation of cell nuclei, which is characteristic of dead cells (FIG. 8). As a result, nuclear fragmentation was observed in Jurkat cells by further cross-linking 2D7 with an antibody, indicating that cell death was induced.

EXAMPLE 4

Cloning of cDNA Encoding the 2D7 Antibody Variable Region, and the Predicted Diabody Structure Primers for the constant regions of the heavy chain and light chain of mouse IgG2b were produced, and DNA encoding the 2D7 variable region was cloned by 5'RACE method. The nucleotide sequences of the obtained PCR products are shown in SEQ ID NO: 1 and 3.

Figure 10A:
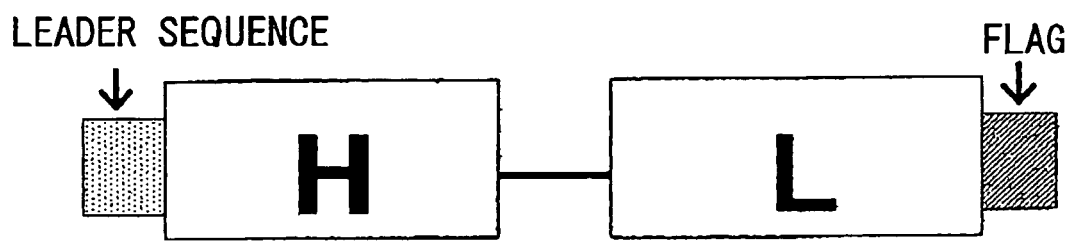
FIG. 10A and FIG. 10B show a 2D7 diabody structure.
Figure 10B:
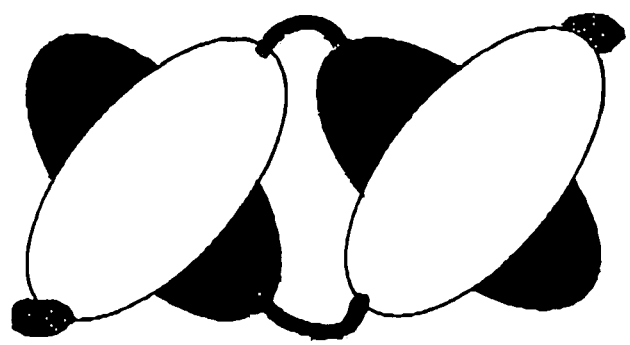

A single chain was then constructed based on these sequences. As shown in FIG. 9 and FIG. 10A, the 2D7 single chain is composed of the leader sequence of the heavy chain, the variable region of the heavy chain, and then across from a 5mer linker (GGGGS), the variable region of a light chain, followed by a cDNA (SEQ ID NO: 5) encoding a Flag-tag. Dimerization of this single chain may cause the 2D7 diabody to form the structure shown in FIG. 10B.

EXAMPLE 5

Analysis of the Cytotoxic Activity of the 2D7 Diabody (i) Cytotoxic Activity of the 2D7 Diabody Transiently Expressed in COS7

Figure 10C:
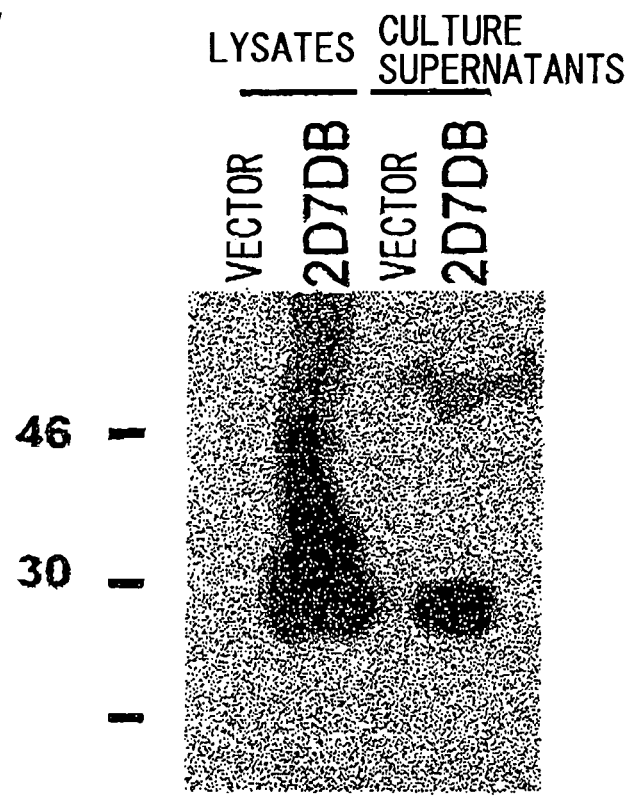
FIG. 10C is a photograph showing its transient expression in COS7 cells.

A 2D7 diabody expression vector was transfected into COS7 cells, and the culture supernatant was collected three days later. The culture supernatant and cell lysate were subjected to SDS-PAGE, and after performing Western blotting with an anti-Flag-tag antibody, a 2D7 single chain was found to be secreted in the culture supernatant (FIG. 10C).

Figure 11A:
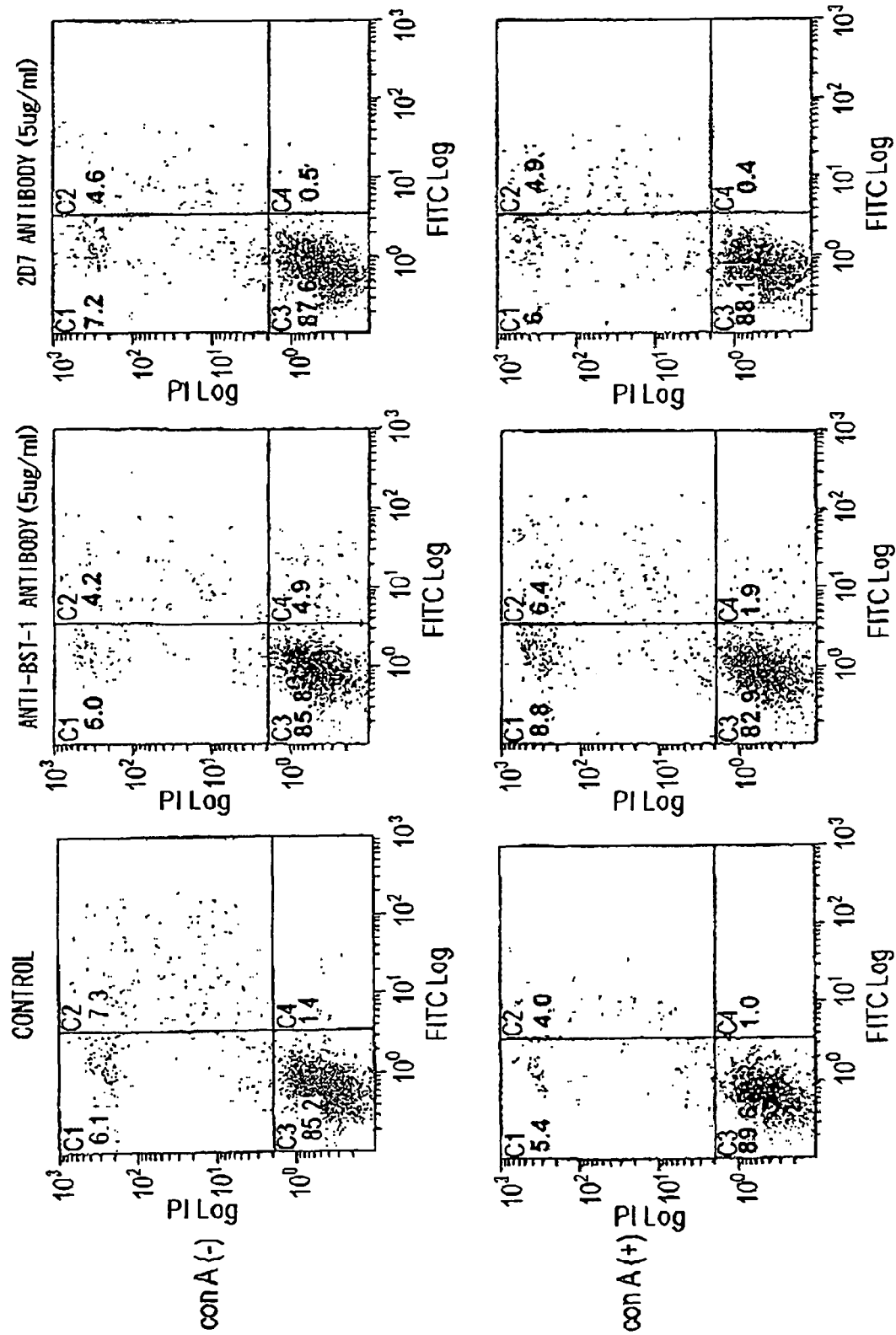
FIG. 11A and FIG. 11B show the cytotoxic activity of 2D7DB transiently expressed in COS7.
Figure 11B:
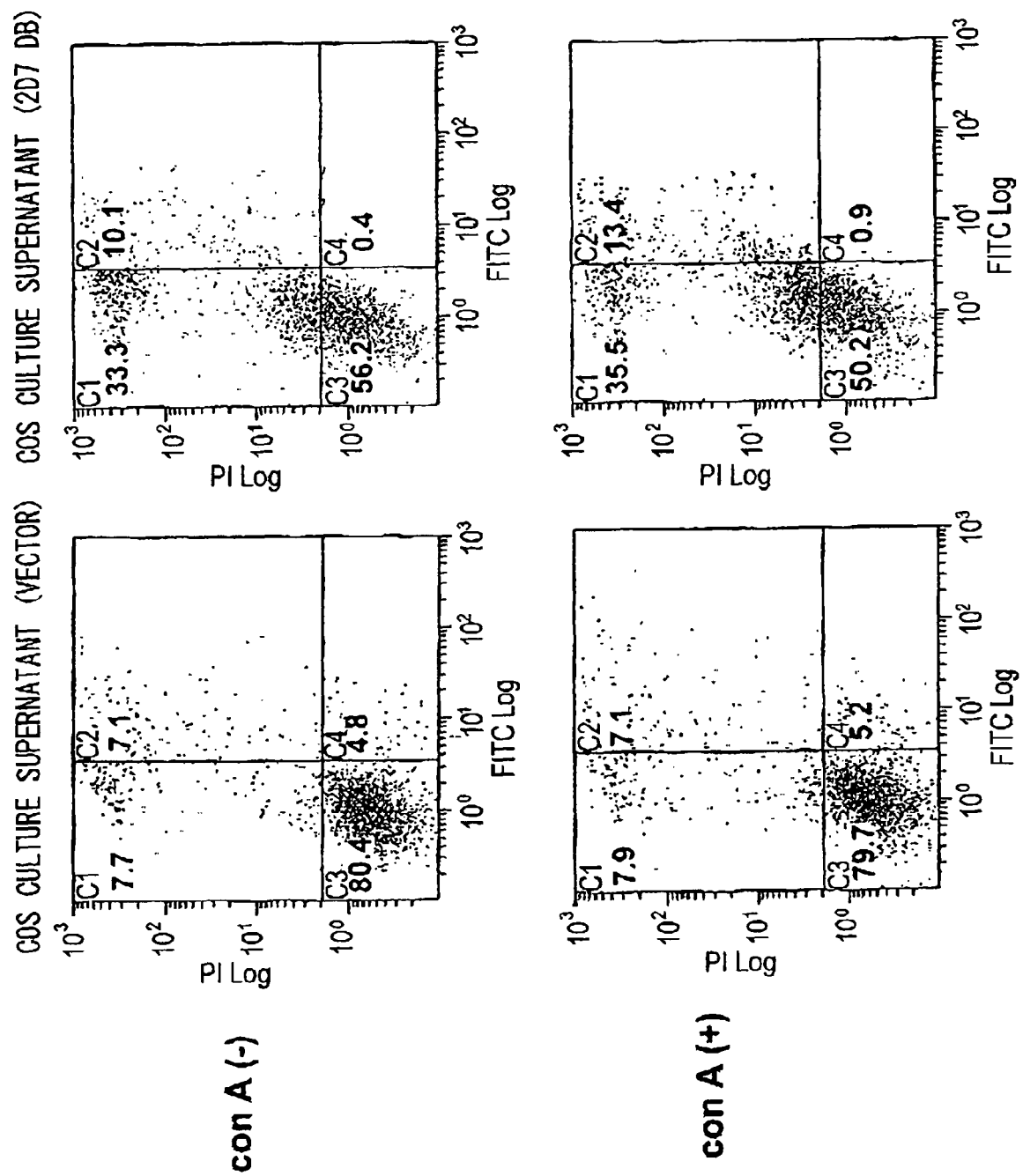

This culture supernatant was added to Jurkat cells at a ratio of 50%. The percentage of dead cells was measured by staining the cells with PI and Annexin V a few days later. No significant change in the apoptosis marker was observed in Jurkat cells to which just the anti-BST-1 antibody and 2D7 antibody (5 μg/ml each) were added. Furthermore, no particular change could be observed when using the culture supernatant of COS7 transfected with the vector alone. On the other hand, cell death was clearly induced in Jurkat cells to which the culture supernatant of COS7 expressing 2D7DB was added (FIG. 11A and FIG. 11B).

Figure 12A:
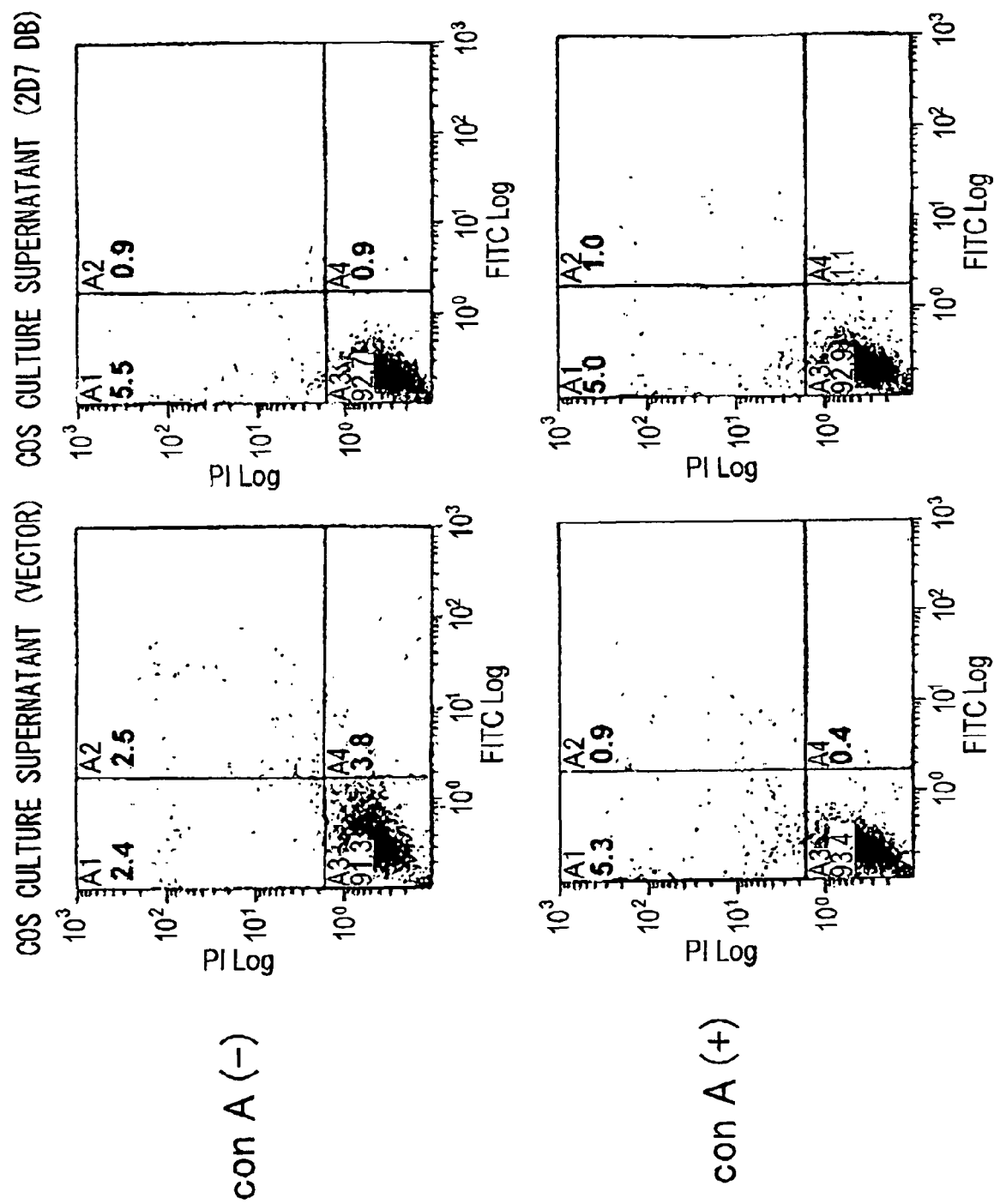
FIG. 12 shows the cytotoxic activity of 2D7DB transiently expressed in COS7. K562 cells (FIG. 12A) and Jurkat cells (FIG. 12B) were used.
Figure 12B:
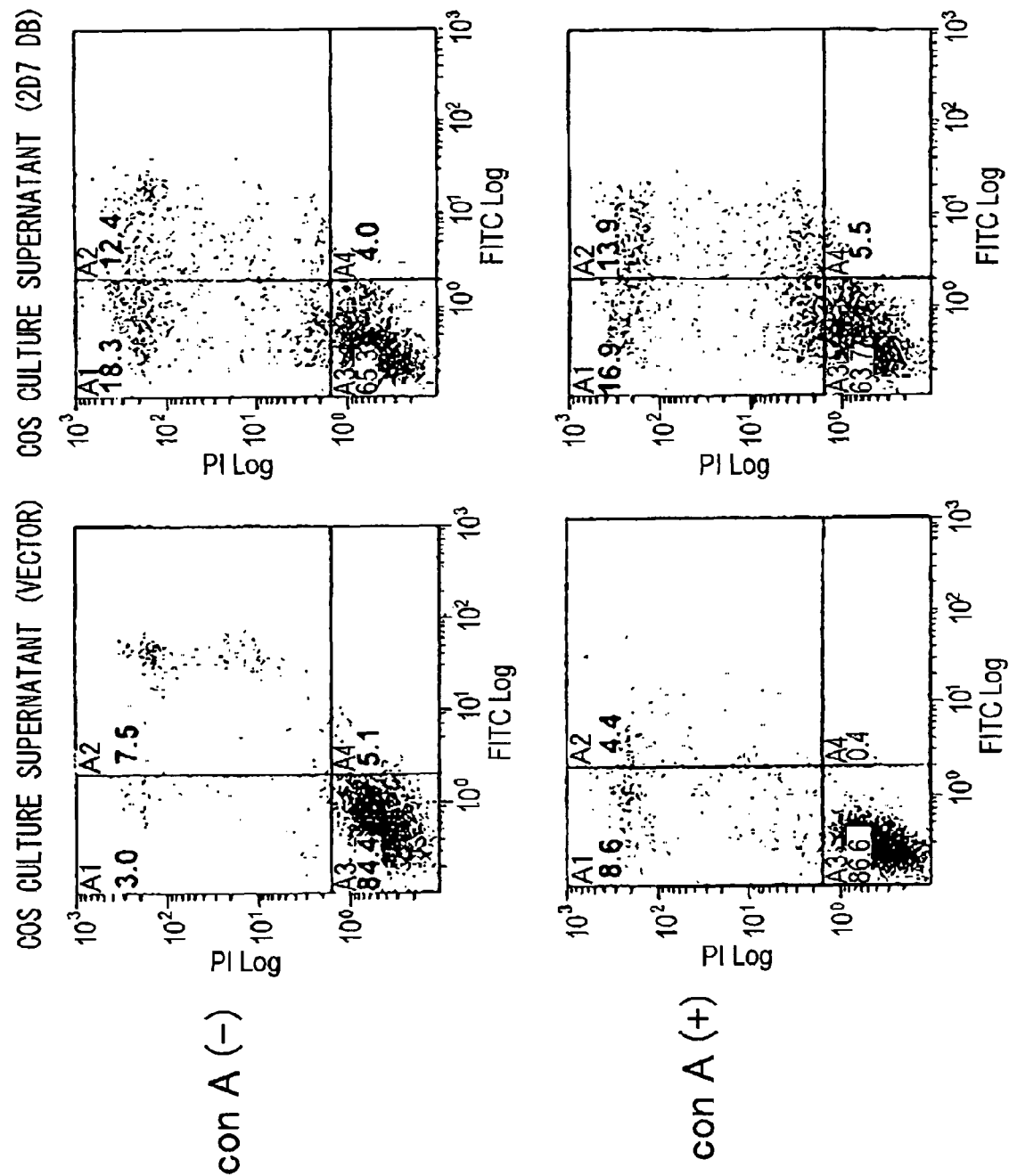
Figure 13A:
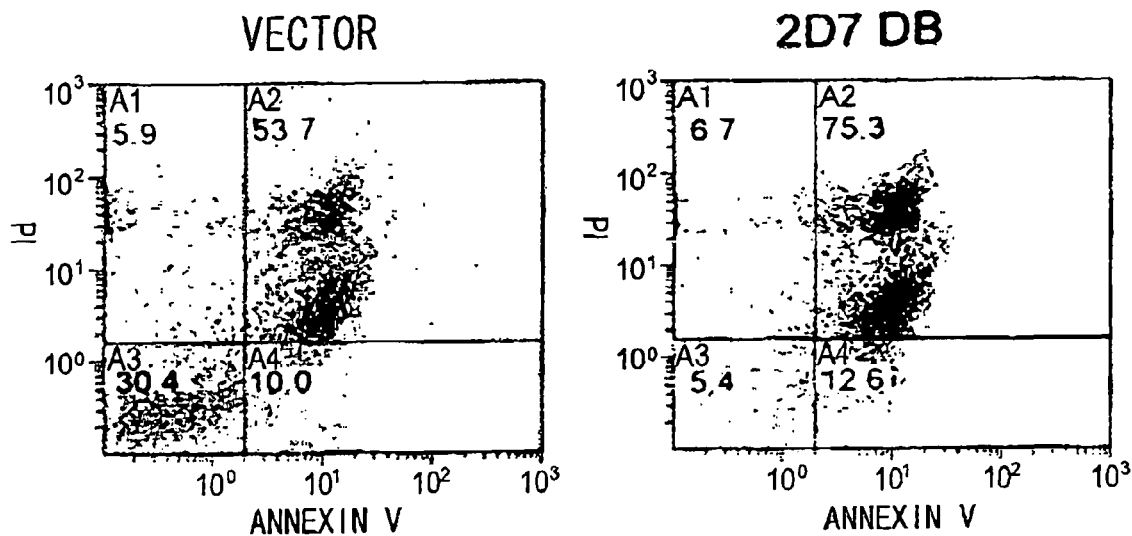
FIG. 13 shows the cytotoxic activity of 2D7DB transiently expressed in COS7. RPMI8226 cells (FIG. 13A), IL-KM3 cells (FIG. 13B), U266 cells (FIG. 13C), and ARH77 cells (FIG. 13D) were used.
Figure 13B:
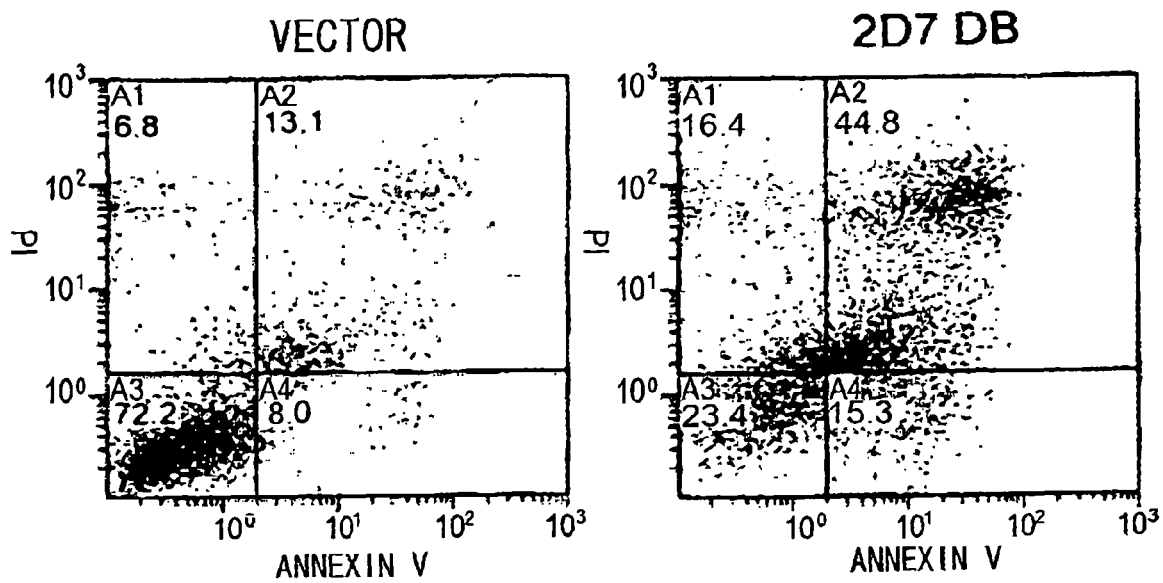
Figure 13C:
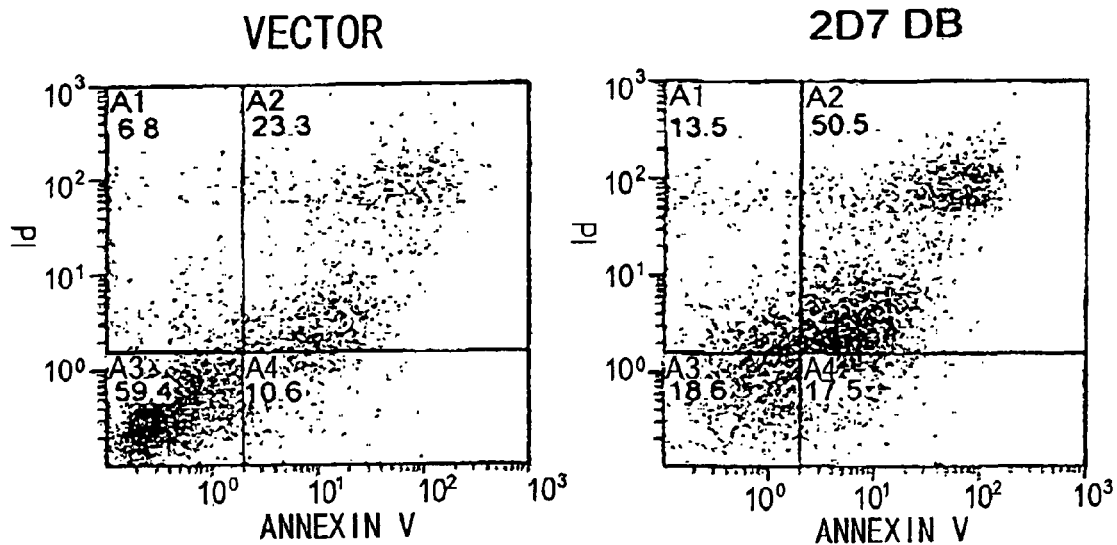
Figure 13D:
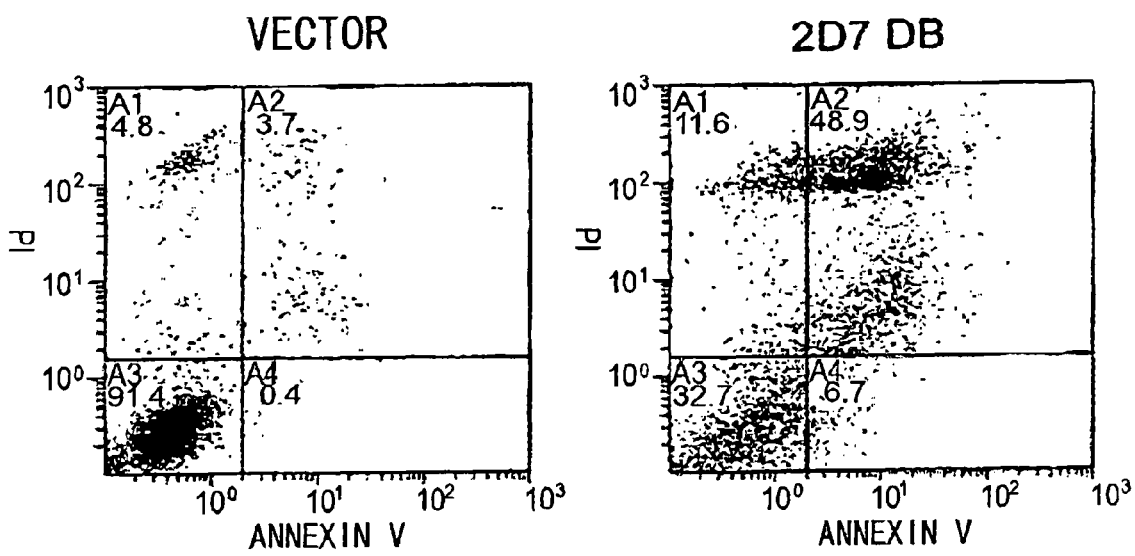

Next, to investigate the HLA class IA-specific action of this 2D7DB, a similar experiment was performed using K562 cells, which are known to not express HLA class IA. As a result, 2D7DB had absolutely no influence on K562 cells, although it showed cell death inducing activity against Jurkat cells (FIG. 12A and FIG. 12B). This strongly supports the idea that the cell death inducing activity of 2D7DB is an action targeting HLA class IA, which is its epitope. Furthermore, according to each data, the sensitivity of Jurkat cells towards 2D7DB was found to be slightly higher in cells stimulated with con A.

Next, the action of 2D7DB on other myeloma cell lines was analyzed. RPMI8226, IL-KM3, U266, and ARH77 were incubated with culture supernatant in which the vector alone was transfected (control), or with the 2D7DB-expressing COS7 culture supernatant. Two days later these cultures were double stained with Annexin V and PI, and analyzed using a flow cytometer. As a result, incubation with 2D7DB was found to significantly induce cell death in all of the cells (FIG. 13A to FIG. 13D).

(ii) Cytotoxic Activity of Purified 2D7DB

Figure 14:
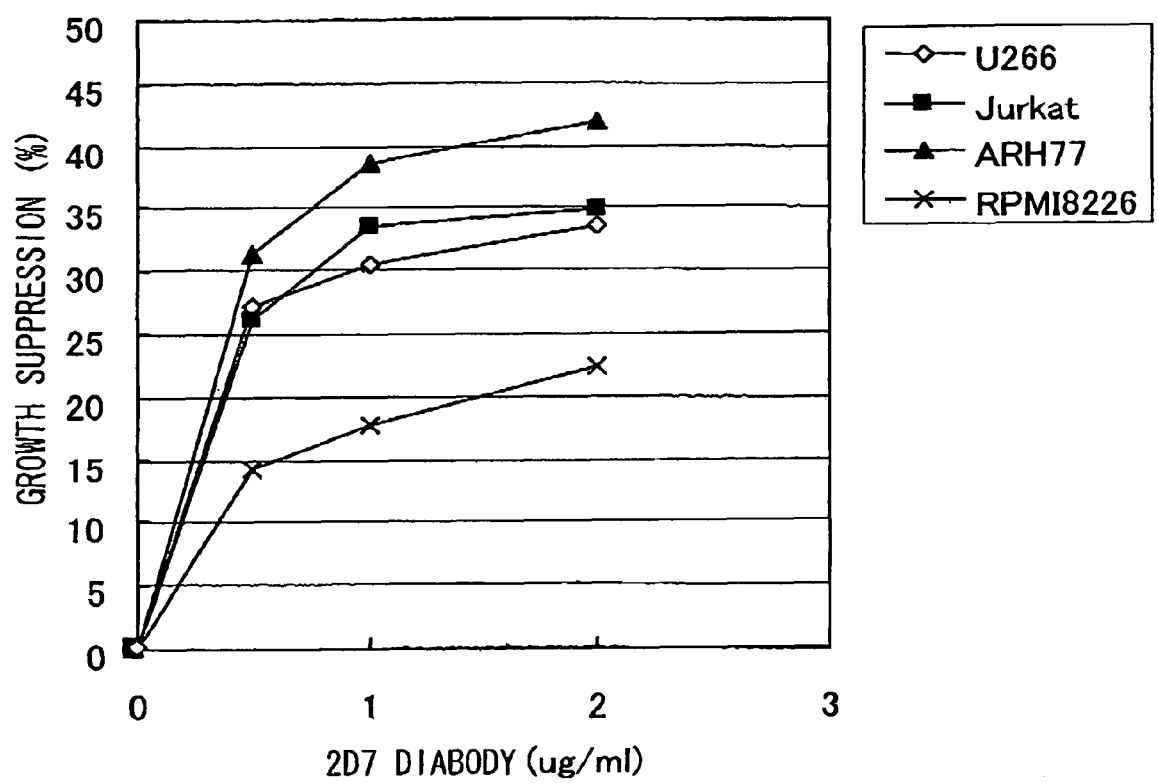
FIG. 14 is a graph showing the growth-suppressing effect of purified 2D7DB.

The growth inhibitory effect of purified 2D7DB on each type of cell line (RPMI8226, ARH77, U266, and Jurkat) was analyzed. 2D7DB was added at 0, 0.5, 1.0, and 2.0 μg/ml, and the number of cells was counted three days later. As a result, 2D7DB was found to inhibit cell growth of these cells in a concentration-dependent manner (FIG. 14).

Figure 16A:
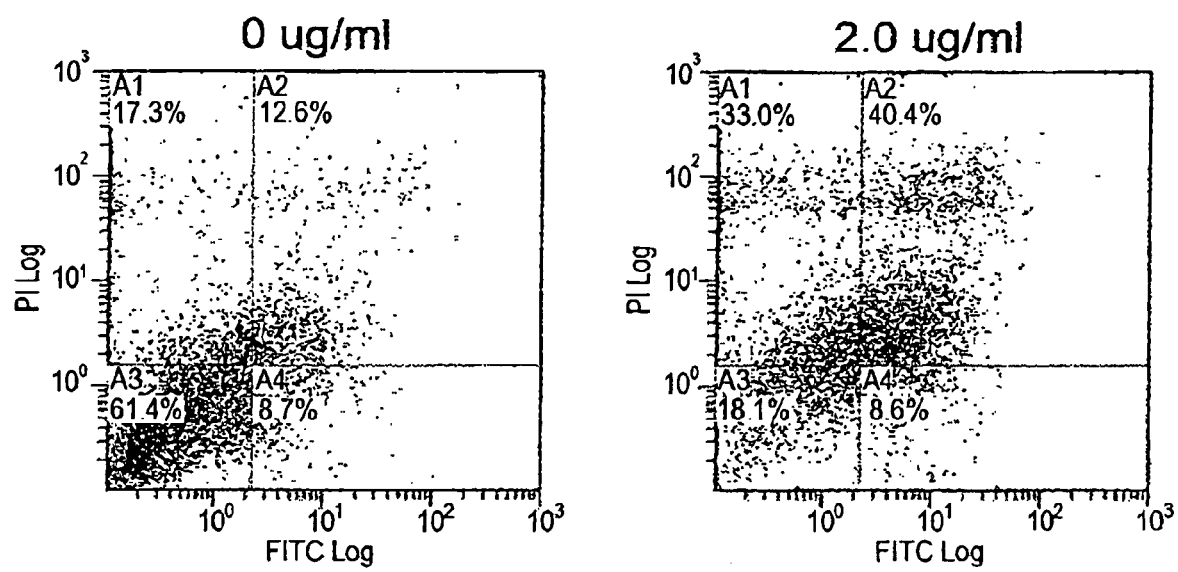
FIG. 16 shows cell death induction by purified 2D7DB, 48 hours after induction U266 cells (FIG. 16A), and IL-KM3 cells (FIG. 16B) were used for the study.
Figure 16B:
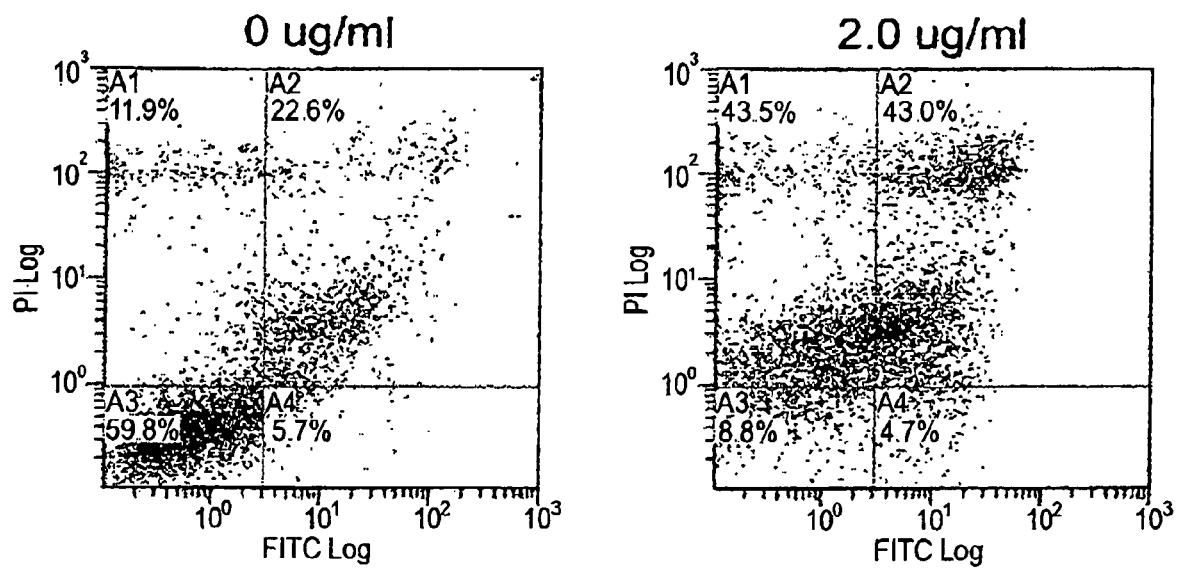

Purified 2D7DB was then added, and 48 hours later, cells were stained with cell death markers, PI and Annexin V, and then analyzed. As in the results obtained when using 2D7DB transiently expressed in COS7, cell death was induced in Jurkat and ARH77 in a concentration-dependent manner, and K562 was not affected at all (FIG. 15A to FIG. 15C). Furthermore, 48 hours after the addition of 2D7DB to U266 and IL-KM3, significant cell death inducing activity was confirmed (FIG. 16A and FIG. 16B).

On the other hand, although the 2D7 antibody stained the adherent HeLa cells very well, 2D7DB had absolutely no influence under the same conditions (FIG. 15D). This suggested that 2D7DB may act specifically on non-adherent cells, such as white blood cells.

Figure 17A:
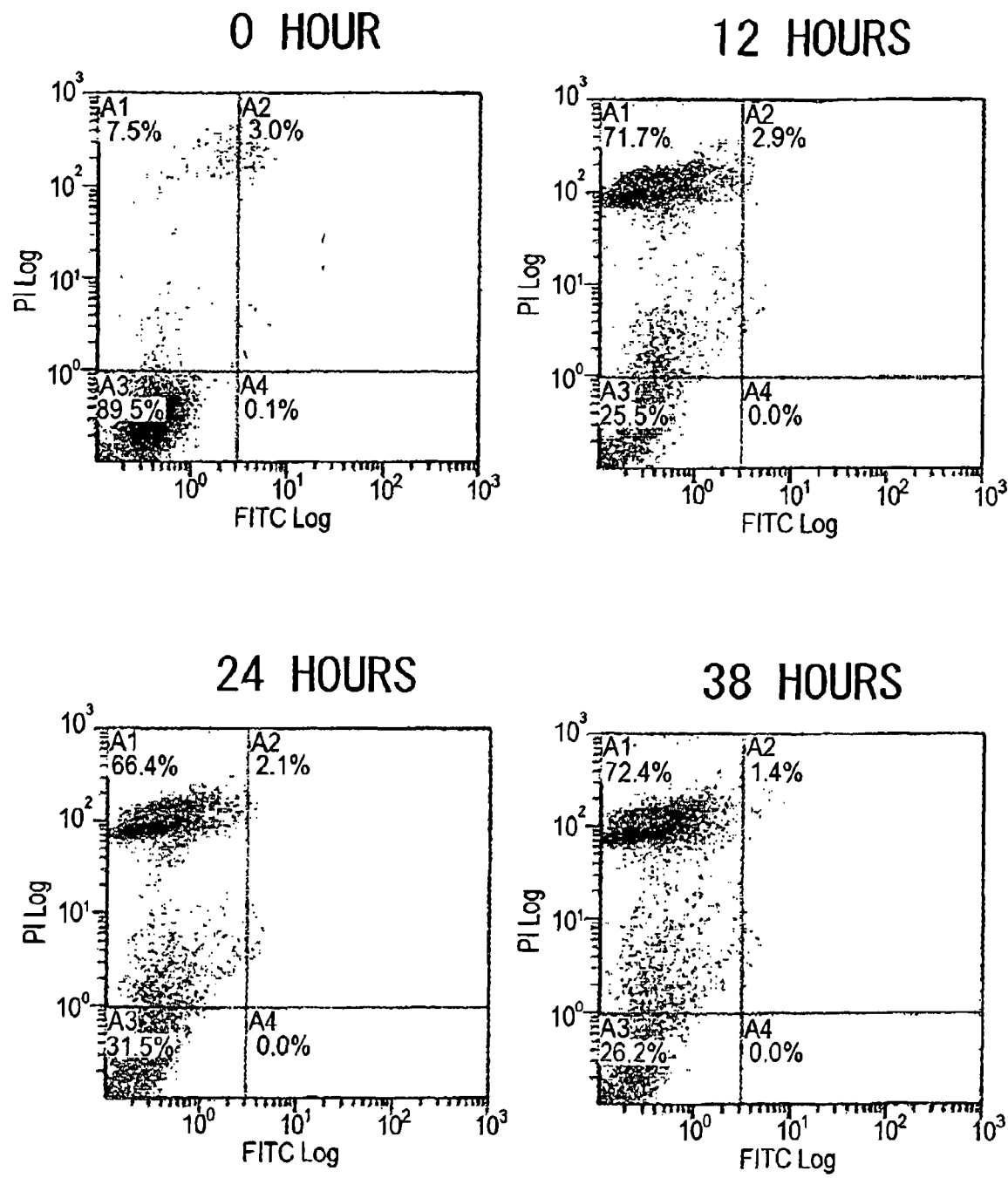
FIG. 17 shows a time course of cell death induction by 2D7DB (2 μg/ml). Cell death induction was investigated at 12 through to 38 hours. ARH77 cells (FIG. 17A) and Jurkat cells (FIG. 17B) were used.
Figure 17B:
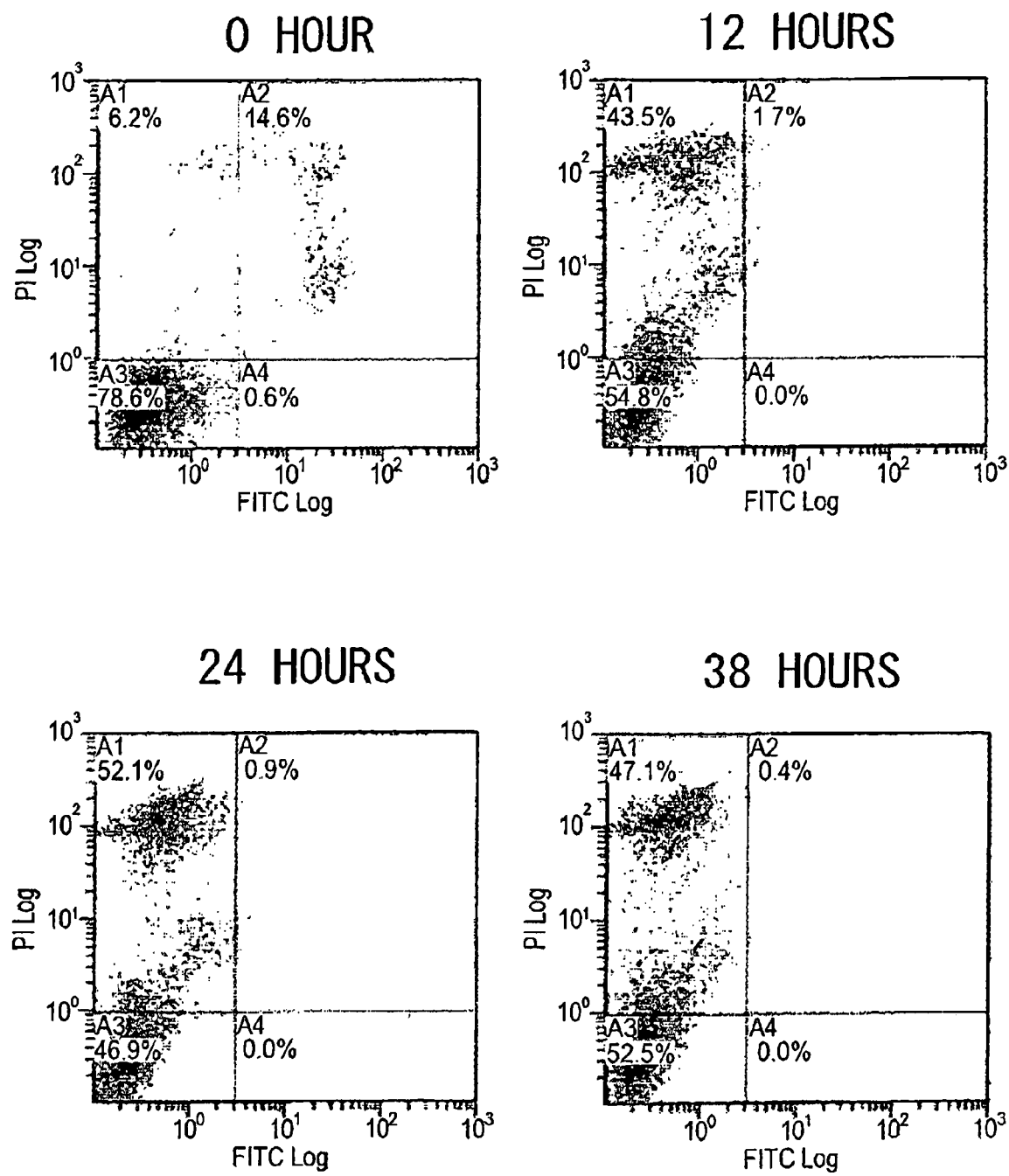

Next, the time taken or 2D7DB to induce cell death was analyzed. 2 μg/ml of 2D7DB was added to ARH77 and Jurkat cells, cells were collected 12, 24, and 38 hours later, and stained with a cell death marker. The results showed that cell death was already induced in all cells twelve hours later (FIG. 17A and FIG. 17B). Therefore, cell death induction was investigated at earlier times (three and six hours). Surprisingly, it was shown that 2D7DB induces cell death at least within three hours after its addition (FIG. 18A and FIG. 18B). These results strongly support the idea that 2D7DB has a very strong cell death-inducing activity. Since 2D7DB strongly induces cell death, sufficient drug efficacy can be expected even with a short half life in the blood. Furthermore, safety becomes a concern if the whole antibody has strong cell death-inducing activity, considering the length of the half life in the blood; however, producing a diabody can overcome such problems.

Figure 19:
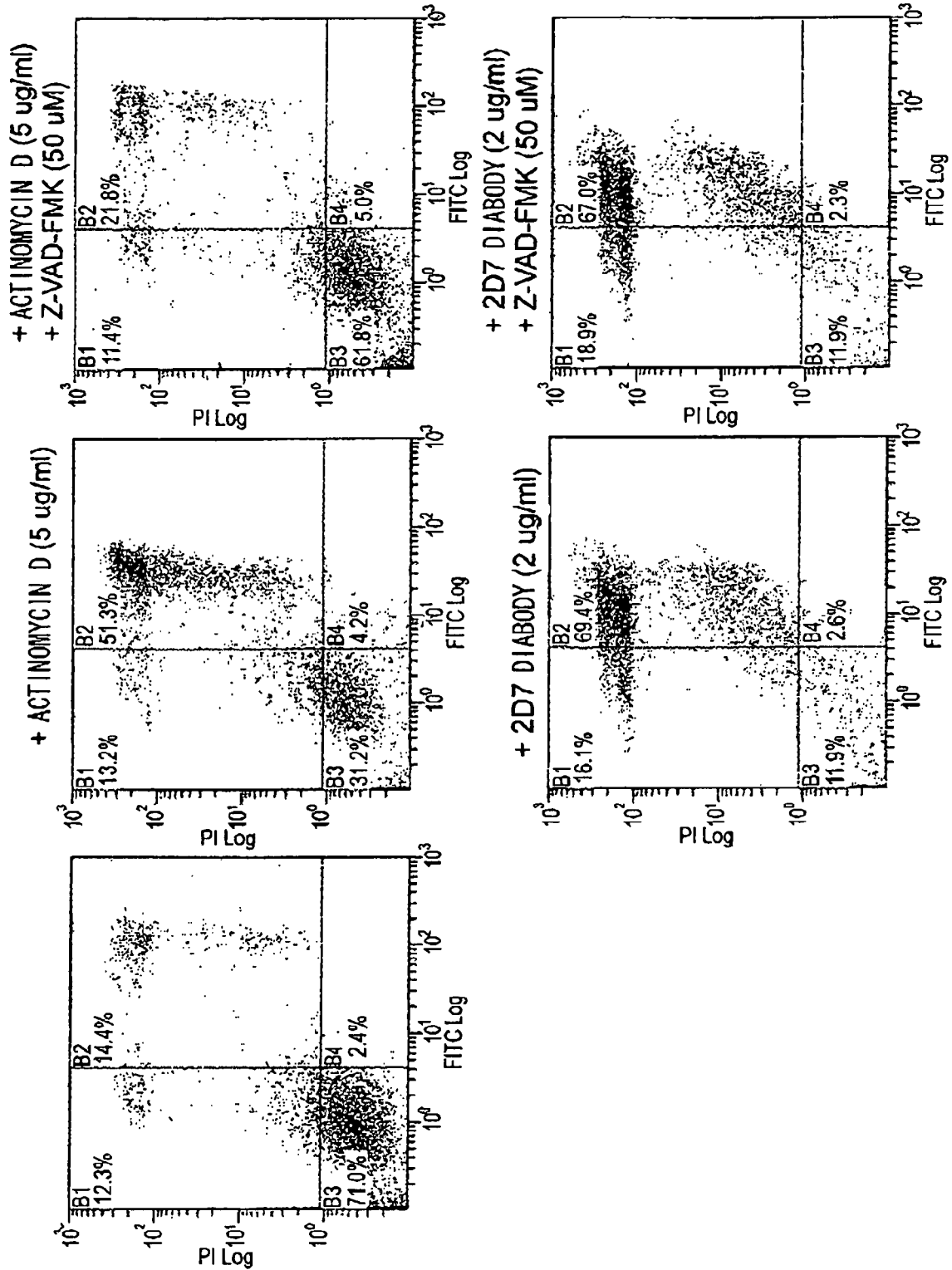
FIG. 19 shows the effect of Z-VAD-FMK on cell death due to 2D7DB. The study was performed using ARH77 cells 16 hours after induction.
Figure 20:
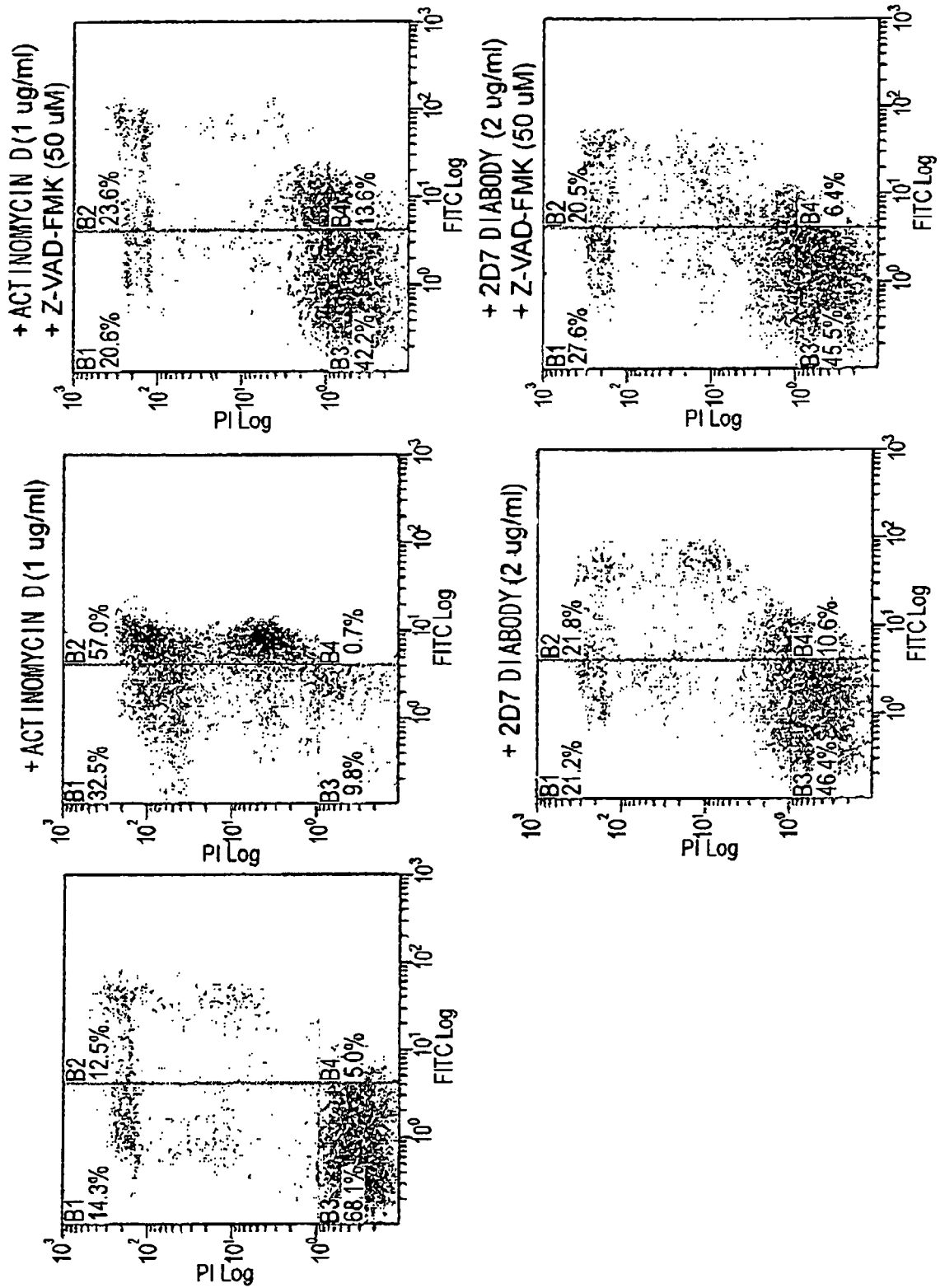
FIG. 20 shows the effect of Z-VAD-FMK on cell death due to 2D7DB. The study was performed using Jurkat cells 16 hours after induction.

Next, analyses were performed to determine whether cell death due to 2D7DB is induced through caspase activation, that is, whether it is apoptosis. As shown in FIG. 19 and FIG. 20, significant apoptosis was induced when ARH77 and Jurkat cells were treated with the apoptosis-inducing agent Actinomycin D, and then stained 16 hours later with-Annexia V and PI. After pre-treating cells under these conditions with caspase inhibitor Z-VAD-FMK for 2.5 hours, apoptosis due to Actinomycin D was suppressed. However, cell death induced by 2D7DB was not inhibited at all by pretreatment with Z-VAD-FMK. These results show that 2D7DB induces cell death by a mechanism different from the ordinary caspase-mediated apoptosis mechanism.

To confirm this, fragmentation of chromatin DNA, known to be the most characteristic biochemical change accompanying apoptosis, was also analyzed.

ARH77 and Jurkat cells were treated with 2D7DB (2 μ/ml) or Actinomycin D, and DNAs were collected from the cells 24 hours later and subjected to electrophoresis (FIG. 21). As a result, DNA fragmentation characteristic of apoptosis had been induced in all cells treated with Actinomycin D, which is an apoptosis-inducing agent. On the other hand, DNA fragmentation was not observed at all in 2D7DB-treated cells, even though the concentration of added 2D7DB was absolutely sufficient to induce cell death. These results also strongly support the idea that cell death due to 2D7DB is an unknown type of cell death, unaccompanied by the characteristics of apoptosis.

From the above-mentioned results, cell death due to 2D7DB was found to be caused by a pathway different from previously known cell death induction mechanisms. Therefore, further analysis was performed to elucidate the mechanism of cell death induction by 2D7DB. From the experiments described above, when 21)7DB was reacted with the cells, the cell membranes were often observed to be destroyed under the microscope. Therefore, 2D7DB was presumed to have some sort of influence on the actin skeleton. In order to examine such a possibility, an actin polymerization inhibitor (cytochalasin D) was made to act on the cells, and the influence of:2D7DB on cell death induction activity was analyzed.

Figure 22:
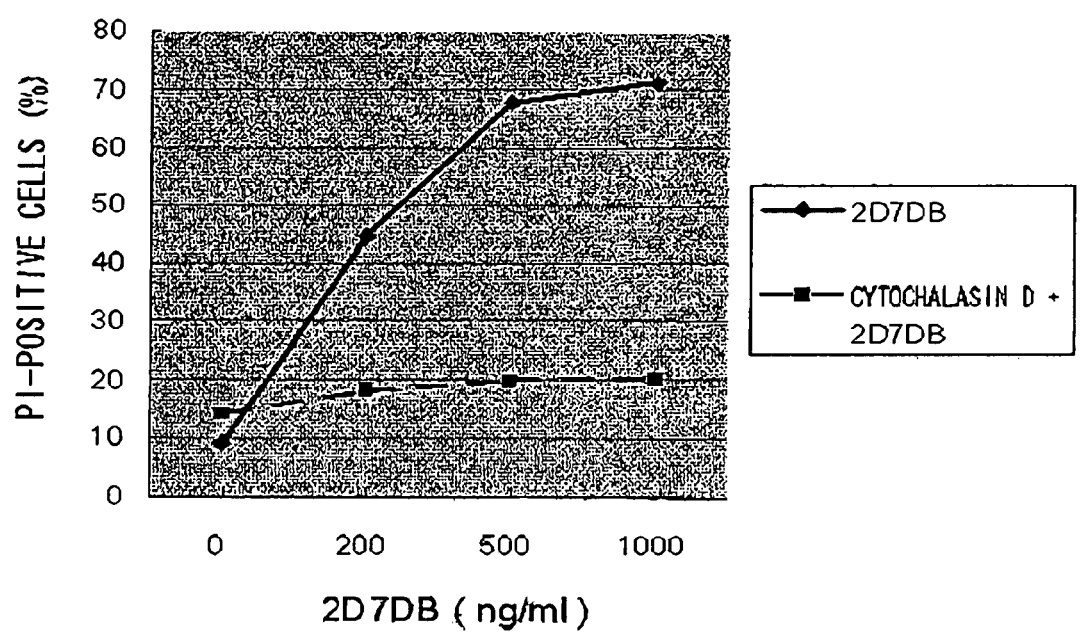
FIG. 22 shows the results of investigating the effect of cytochalasin D on the cell death-inducing activity of 2D7DB. By pre-treating ARH77 cells with cytochalasin D, which is an actin-polymerization inhibitor, the cells showed resistance to 2D7DB-induced cell death.

Cytochalasin D (20 μg/ml) or ethanol alone (control) was added to ARH77 cells, and 1 hour later, 2D7DB was added at various concentrations. After a 4-hour incubation from the 2D7DB addition, cells were collected, PI staining was performed and the percentage of dead cells was measured (FIG. 22). As a result, pretreatment of cells with cytochalasin D was found to cause loss of sensitivity towards 2D7DB. These results suggested that 2D7DB causes some kind of effect on the cytoskeletal system, such as actin, to induce cell death by binding to HLA-class IA, which is the target molecule.

Therefore, cells treated with 2D7DB were stained by the actin antibody, and the dynamic change of the cytoskeletal system due to 2D7DB addition was analyzed visually. ARH77 cells were treated with 2D7DB, and 15 minutes later, the cells were immobilized with methanol, and the state of actin (red) in the cells was investigated by immunostaining (FIG. 23). As a result, compared to the image from those not treated with 2D7DB, significant destruction of the actin skeleton in the cell due to 2D7DB was observed.

The above-mentioned results strongly suggested that cell death due to 2D7DB may be caused by destruction of the actin skeleton-in cells by 2D7DB bound to HLA class IA. This is a completely new type of cell death induction mechanism that has not been reported to date.

EXAMPLE 6

Drug Efficacy Test for 2D7 Diabody Using Human Myeloma Animal Model (1) Production of Mouse Model for Human Myeloma A mouse model for human myeloma was produced as follows. ARH 77 cells were prepared to reach $2.5 \times 10^7$ cells/ml in RPMI1640 medium (GIBCO BRL) supplemented with 10% fetal calf serum (GIBCO BRL), and then 200 AL of the above-mentioned ARH77 cell suspension ($5 \times 10^6$ cells/mouse) was injected to SCID mice (male, 6 weeks old, Clea Japan) pretreated the day before with intraperitoneal administration of 0.2 mg of anti-asialo GM1 antibody (Wako Pure Chemicals) from the tail vein.

(2) Preparation of the Antibody to be Administered

On the day of administration, a 2D7 diabody was prepared at 0.8 mg/ml using filter-sterilized PBS(−), and this was used as the administration sample.

(3) Antibody Administration

To the mouse model of human myeloma produced in (1), the administration sample-prepared in (2) was administered through the tail vein at 10 ml/kg twice a day for 3 days from the first day after engraftment of ARH77 cells. As a negative control (vehicle), filter-sterilized PBS(−) was administered similarly at 10 ml/kg through the tail vein twice a day for 3 days. The antibody-administered group bad 7 animals per group, and the vehicle-administered group had 8 animals per group.

(4) Human IgG Assay of Mouse Serum

The quantity of human IgG produced by human myeloma cells in the mouse serum was determined by ELISA described below. 100 μL of goat anti-human IgG antibody (BIOSOURCE) diluted to 1 μg/ml with 0.1% bicarbonate buffer (pH9.6) was placed into a 96-well plate (Nunc), this was incubated at 4° C. overnight, and the antibody was immobilized. After blocking, mouse serum diluted in a stepwise manner, or as the authentic sample, 100 μL of human IgG (Cappel) was added, and this was incubated at room temperature for 1 hour. After washing, 100 μL of a 5000-fold diluted alkaline phosphatase-labeled anti-human IgG antibody (BIOSOURCE) was added, and this was incubated at room temperature for 1 hour. After washing, substrate solution was added, and after incubation, absorbance at 405 nm was measured using MICROPLATE READER Model 3550 (Bio-Rad), and the concentration of human IgG in mouse serum was calculated from the calibration curve obtained from the absorbance of the authentic human IgG sample.

(5) Evaluation of Anti-Tumor Effect

Figure 24:
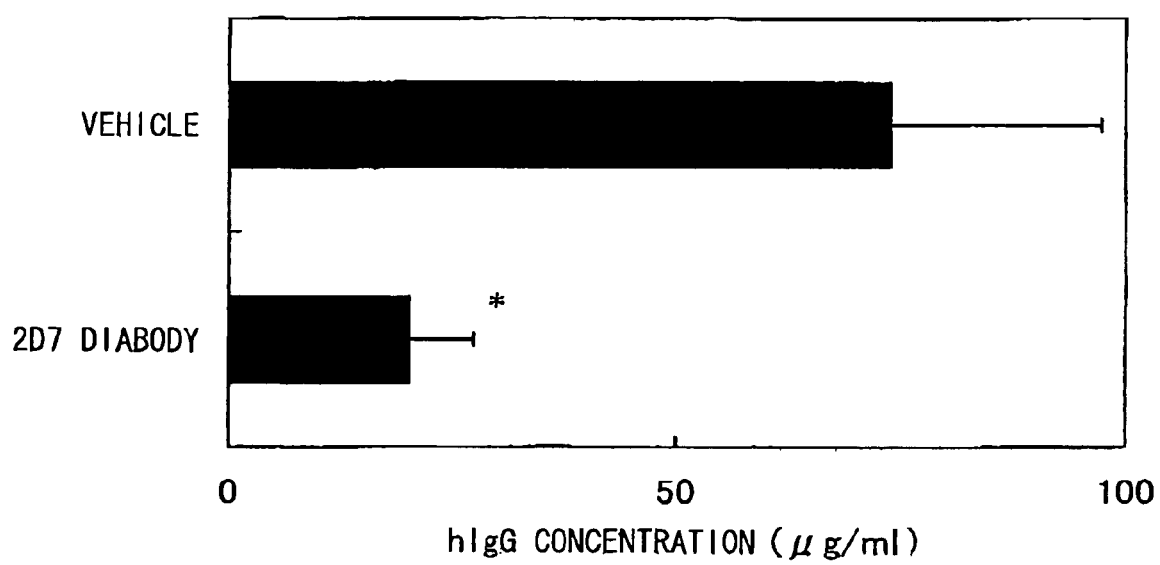
FIG. 24 shows that the 2D7DB suppresses an increase in human IgG (hIgG) concentration in serum in a mouse model of human myeloma. The data shows the average + SEM. There was a significant difference (*: $p<0.05$) between the vehicle-administered group and the 2D7DB-administered group, according to unpaired t-tests.
Figure 25:
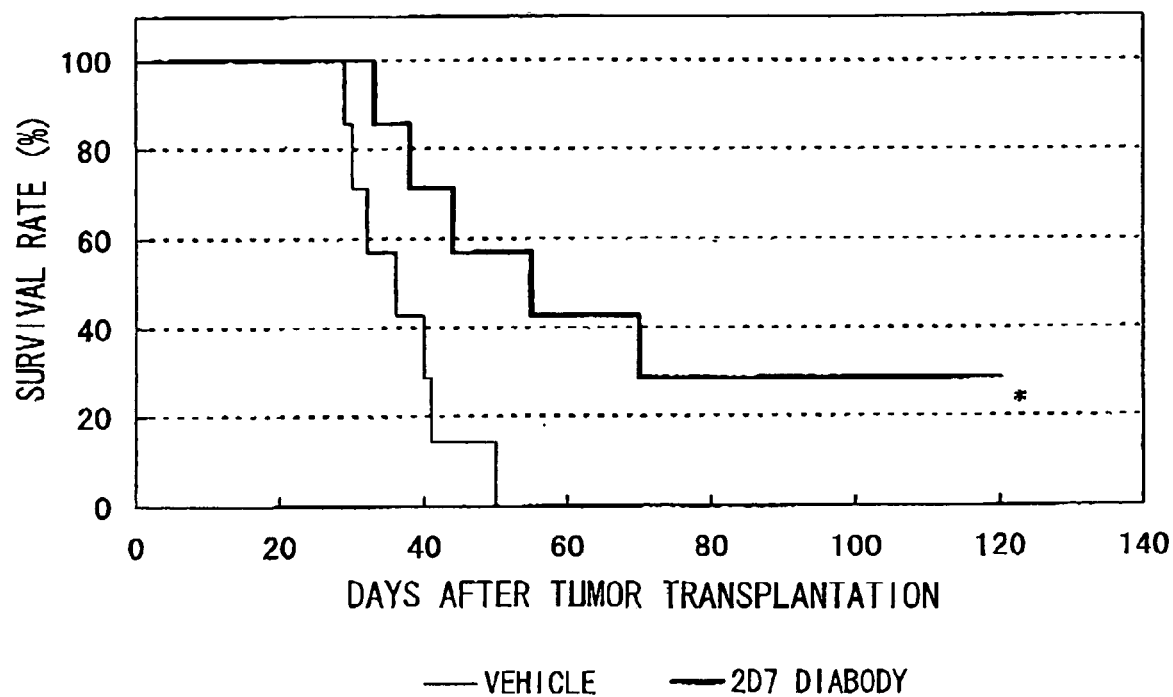
FIG. 25 shows that the 2D7DB has a life-prolonging effect in a mouse model of human myeloma. There was a significant difference (*: $p<0.05$) between the vehicle-administered group and the 2D7DB-administered group, according to generalized Wilcoxon tests.

The anti-tumor effect of the 2D7 diabody on a human myeloma mouse model was evaluated using the change in the amount of human IgG (M protein) produced by the myeloma cells in mouse serum, and by the survival time. Regarding the change in human IgG level in mouse serum, serum was collected on the 24th day after transplanting the ARH77 cells, and the human IgG level was measured by the ELISA described above in (4). As a result, the level of human IgG (M protein) in the serum had increased in the vehicle-administered group to approximately 74 μg/ml. In contrast, the level in the 2D7 diabody-administered group was significantly lower than in the control group (P<0.005, unpaired t-test), and 2D7 diabody was shown to very strongly suppress the growth of ARH77 cells (FIG. 24). With regards to survival time, as shown in FIG. 25, the 2D7 diabody-administered group showed a significant increase in survival time compared to the vehicle-administered group.

Accordingly, the 2D7 diabody was shown to have an anti-tumor effect on the mouse model of human myeloma. The antitumor effect of the 2D7 diabodies of this invention may be based on the cell death-inducing action of this antibody.

EXAMPLE 7

Analysis of the Action of 2D7DB on PBMC

The action of 2D7DB on human peripheral blood mononuclear cells (PBMCs) was analyzed. PBMCs were purified from the peripheral blood of a healthy adult volunteer by density gradient centrifugation. The PBMCs were plated at $5 \times 10^5$ cells/1 ml/well onto a 24-well plate, in the presence or absence of a mitogen. Phytohemagglutinin M (PHA-M, Roche Diagnostics, final concentration: 10 μg/ml), concanavalin A (Con, Wako, final concentration: 10 μg/ml), and SAC (Pansorbin Cells, Calbiochem, final concentration: 0.01%) were used as mitogens. Cells were cultured in a 5% $CO_2$ incubator at 37° C. for three days. 24 or 3 hours before culture was complete, 2D7DB was added to yield a final concentration of 2 μg/ml. After culture was complete, the cells were double stained with Annexin V and PI (Annexin V-FITC Apoptosis Detection Kit I, Pharmingen), and then analyzed using a flow cytometer (EPICS XL, Coulter). As a positive control, ARH77 at 2.5×10[5] cells/1 ml/well was cultured for 24 hours in the absence of a mitogen, and was reacted with 2D7DB, as for PBMC.

In the case of PBMC, the percentages of dead cells that were both Annexin V and PI-positive were 29%, 23%, and 25% in the absence of mitogens (in order: no addition, 3-hour addition, and 24-hour addition of 2D7DB; continued below); 20%, 45%, and 42% in the presence of PHA-M; 22%, 30%, and 34% in the presence of ConA; and 31%, 38%, and 40% in the presence of SAC (FIGS. 26A to 26D). In the case of ARH77, the percentages were 16%, 56%, and 58% (FIG. 26E). These results showed that 2D7DB has hardly any effect on unstimulated PBMC, but induces cell death in a short time with mitogen-activated PBMC.

INDUSTRIAL APPLICABILITY

This invention provides minibodies with high specific activities. By using these minibodies, adequate drug efficacy can be expected even with a short half life. The minibodies of the present invention are firer expected to be able to separate drug efficacy from toxicity. In addition, since overall cost is reduced, including reducing clinical dose and production cost, economical problems of concern in the development of antibody pharmaceuticals are also expected to improve.

The invention claimed is:

1. A method of producing a minibody, the CDRs of which have the same amino acid sequences as the CDRs of a whole antibody that recognizes a domain selected from the group consisting of domain α1 and domain α2 of an HLA-A antigen, wherein the minibody has a level of cytotoxic activity greater than that of the whole antibody, the method comprising:
   (a) providing a DNA encoding the minibody;
   (b) expressing the minibody from the DNA; and
   (c) confirming that the expressed minibody possesses cytotoxic activity greater than that of the whole antibody, wherein the minibody is an scFv or a diabody.

2. The method of claim 1, wherein the minibody comprises human framework regions.

3. The method of claim 1, wherein the whole antibody is a human antibody.

4. The method of claim 1, wherein the whole antibody is a non-human antibody and the minibody is humanized.

5. The method of claim 1, wherein the cytotoxic activity is a cell death-inducing activity.

6. The method of claim 1, wherein the cytotoxic activity is a cell growth-suppressing activity.

7. An HLA-recognizing scFv or diabody produced by the method of claim 1.

8. The method of claim 1, wherein the minibody recognizes domain α1 of an HLA-A antigen.

9. The method of claim 1, wherein the minibody recognizes domain α2 of an HLA-A antigen.

* * * * *

SEQUENCE LISTING

```
<160> NUMBER OF SEQ ID NOS: 14

<210> SEQ ID NO 1
<211> LENGTH: 547
<212> TYPE: DNA
<213> ORGANISM: Mus musculus
<220> FEATURE:
<221> NAME/KEY: CDS
<222> LOCATION: (103)..(546)

<400> SEQUENCE: 1
tacgactcac tatagggcaa gcagtggtat caacgcagag tacgcgggga atctatgatc      60
agtgtcctct ctacacagtc cctgacgaca ctgactccaa cc atg cga tgg agc      114
                                               Met Arg Trp Ser
                                                 1 tgg atc ttt ctc ttc ctc ctg tca ata act gca ggt gtc cat tgc cag      162
Trp Ile Phe Leu Phe Leu Leu Ser Ile Thr Ala Gly Val His Cys Gln
  5                  10                  15                  20 gtc cag ttg cag cag tct gga cct gag ctg gtg aag cct ggg gct tca      210
Val Gln Leu Gln Gln Ser Gly Pro Glu Leu Val Lys Pro Gly Ala Ser
             25                  30                  35 gtg aag atg tct tgt aag gct tct ggc tac acc ttc aca gac tac ttt      258
Val Lys Met Ser Cys Lys Ala Ser Gly Tyr Thr Phe Thr Asp Tyr Phe
         40                  45                  50 ata cac tgg gtg aaa cag agg cct gga cag gga ctt gaa tgg att gga      306
Ile His Trp Val Lys Gln Arg Pro Gly Gln Gly Leu Glu Trp Ile Gly
     55                  60                  65 tgg att ttt cct gga gat gat act act gat tac aat gag aag ttc agg      354
Trp Ile Phe Pro Gly Asp Asp Thr Thr Asp Tyr Asn Glu Lys Phe Arg
 70                  75                  80 ggc aag acc aca ctg act gca gac aaa tcc tcc agc aca gcc tac att      402
Gly Lys Thr Thr Leu Thr Ala Asp Lys Ser Ser Ser Thr Ala Tyr Ile
 85                  90                  95                 100 ttg ctc agc agc ctg acc tct gag gac tct gcg atg tat ttc tgt gta      450
Leu Leu Ser Ser Leu Thr Ser Glu Asp Ser Ala Met Tyr Phe Cys Val
                105                 110                 115 agg agt gac gac ttt gac tac tgg ggc cag ggc acc act ctc aca gtc      498
Arg Ser Asp Asp Phe Asp Tyr Trp Gly Gln Gly Thr Thr Leu Thr Val
                120                 125                 130 tcc tca gcc aaa aca aca ccc cca tca gtc tat cca ctg gcc cct gct g   547
Ser Ser Ala Lys Thr Thr Pro Pro Ser Val Tyr Pro Leu Ala Pro Ala
            135                 140                 145

<210> SEQ ID NO 2
<211> LENGTH: 148
<212> TYPE: PRT
<213> ORGANISM: Mus musculus
```

<400> SEQUENCE: 2

```
Met Arg Trp Ser Trp Ile Phe Leu Phe Leu Ser Ile Thr Ala Gly
  1               5                  10                  15

Val His Cys Gln Val Gln Leu Gln Gln Ser Gly Pro Glu Leu Val Lys
             20                  25                  30

Pro Gly Ala Ser Val Lys Met Ser Cys Lys Ala Ser Gly Tyr Thr Phe
         35                  40                  45

Thr Asp Tyr Phe Ile His Trp Val Lys Gln Arg Pro Gly Gln Gly Leu
     50                  55                  60

Glu Trp Ile Gly Trp Ile Phe Pro Gly Asp Asp Thr Thr Asp Tyr Asn
 65                  70                  75                  80

Glu Lys Phe Arg Gly Lys Thr Thr Leu Thr Ala Asp Lys Ser Ser Ser
                 85                  90                  95

Thr Ala Tyr Ile Leu Leu Ser Ser Leu Thr Ser Glu Asp Ser Ala Met
            100                 105                 110

Tyr Phe Cys Val Arg Ser Asp Asp Phe Asp Tyr Trp Gly Gln Gly Thr
        115                 120                 125

Thr Leu Thr Val Ser Ser Ala Lys Thr Thr Pro Pro Ser Val Tyr Pro
    130                 135                 140

Leu Ala Pro Ala
145
```

<210> SEQ ID NO 3
<211> LENGTH: 535
<212> TYPE: DNA
<213> ORGANISM: Mus musculus
<220> FEATURE:
<221> NAME/KEY: CDS
<222> LOCATION: (103)..(534)

<400> SEQUENCE: 3

```
ctaatacgac tcactatagg gcaagcagtg gtatcaacgc agagtacgcg gggactwatg      60
agaatagcag taattagcta gggaccaaaa ttcaaagaca aa atg cat ttt caa        114
                                                Met His Phe Gln
                                                  1 gtg cag att ttc agc ttc ctg cta atc agt gcc tca gtc atc atg tcc      162
Val Gln Ile Phe Ser Phe Leu Leu Ile Ser Ala Ser Val Ile Met Ser
  5                  10                  15                  20 aga gga caa att gtt ctc acc cag tcg cca gca atc atg tct gca tct      210
Arg Gly Gln Ile Val Leu Thr Gln Ser Pro Ala Ile Met Ser Ala Ser
             25                  30                  35 cca ggg gag aag gtc acc ata acc tgc agt gcc agc tca agt gta agt      258
Pro Gly Glu Lys Val Thr Ile Thr Cys Ser Ala Ser Ser Ser Val Ser
         40                  45                  50 tac atg cac tgg ttc cag cag aag cca ggc act ttt ccc aaa ctc tgg      306
Tyr Met His Trp Phe Gln Gln Lys Pro Gly Thr Phe Pro Lys Leu Trp
     55                  60                  65 att tat agc aca tcc aac ctg gct tct gga gtc cct act cgc ttc agt      354
Ile Tyr Ser Thr Ser Asn Leu Ala Ser Gly Val Pro Thr Arg Phe Ser
 70                  75                  80 ggc agt gga tct ggg acc tct tac tct ctc aca atc agc cga atg gag      402
Gly Ser Gly Ser Gly Thr Ser Tyr Ser Leu Thr Ile Ser Arg Met Glu
             85                  90                  95                 100 gct gaa gat gct gcc act tat tac tgc cag caa agg acg agt tat cca      450
Ala Glu Asp Ala Ala Thr Tyr Tyr Cys Gln Gln Arg Thr Ser Tyr Pro
                105                 110                 115 ccc acg ttc ggc tcg ggg aca aag ttg gag ata aaa cgg gct gat gct      498
Pro Thr Phe Gly Ser Gly Thr Lys Leu Glu Ile Lys Arg Ala Asp Ala
```

```
                     120                 125                  130
gca cca act gta tcc atc ttc cca cca tcc agt gag c                    535
Ala Pro Thr Val Ser Ile Phe Pro Pro Ser Ser Glu
            135                 140
```

<210> SEQ ID NO 4
<211> LENGTH: 144
<212> TYPE: PRT
<213> ORGANISM: Mus musculus

<400> SEQUENCE: 4

```
Met His Phe Gln Val Gln Ile Phe Ser Phe Leu Leu Ile Ser Ala Ser
  1               5                  10                  15

Val Ile Met Ser Arg Gly Gln Ile Val Leu Thr Gln Ser Pro Ala Ile
             20                  25                  30

Met Ser Ala Ser Pro Gly Glu Lys Val Thr Ile Thr Cys Ser Ala Ser
         35                  40                  45

Ser Ser Val Ser Tyr Met His Trp Phe Gln Gln Lys Pro Gly Thr Phe
     50                  55                  60

Pro Lys Leu Trp Ile Tyr Ser Thr Ser Asn Leu Ala Ser Gly Val Pro
 65                  70                  75                  80

Thr Arg Phe Ser Gly Ser Gly Ser Gly Thr Ser Tyr Ser Leu Thr Ile
                 85                  90                  95

Ser Arg Met Glu Ala Glu Asp Ala Ala Thr Tyr Tyr Cys Gln Gln Arg
            100                 105                 110

Thr Ser Tyr Pro Pro Thr Phe Gly Ser Gly Thr Lys Leu Glu Ile Lys
        115                 120                 125

Arg Ala Asp Ala Ala Pro Thr Val Ser Ile Phe Pro Pro Ser Ser Glu
    130                 135                 140
```

<210> SEQ ID NO 5
<211> LENGTH: 789
<212> TYPE: DNA
<213> ORGANISM: Artificial Sequence
<220> FEATURE:
<223> OTHER INFORMATION: Description of Artificial Sequence:an
      artificially synthesized DNA sequence
<220> FEATURE:
<221> NAME/KEY: CDS
<222> LOCATION: (14)..(775)

<400> SEQUENCE: 5

```
cctgaattcc acc atg cga tgg agc tgg atc ttt ctc ttc ctc ctg tca      49
            Met Arg Trp Ser Trp Ile Phe Leu Phe Leu Leu Ser
              1               5                  10 ata act gca ggt gtc cat tgc cag gtc cag ttg cag cag tct gga cct     97
Ile Thr Ala Gly Val His Cys Gln Val Gln Leu Gln Gln Ser Gly Pro
             15                  20                  25 gag ctg gtg aag cct ggg gct tca gtg aag atg tct tgt aag gct tct    145
Glu Leu Val Lys Pro Gly Ala Ser Val Lys Met Ser Cys Lys Ala Ser
         30                  35                  40 ggc tac acc ttc aca gac tac ttt ata cac tgg gtg aaa cag agg cct    193
Gly Tyr Thr Phe Thr Asp Tyr Phe Ile His Trp Val Lys Gln Arg Pro
 45                  50                  55                  60 gga cag gga ctt gaa tgg att gga tgg att ttt cct gga gat gat act    241
Gly Gln Gly Leu Glu Trp Ile Gly Trp Ile Phe Pro Gly Asp Asp Thr
                 65                  70                  75 act gat tac aat gag aag ttc agg ggc aag acc aca ctg act gca gac    289
Thr Asp Tyr Asn Glu Lys Phe Arg Gly Lys Thr Thr Leu Thr Ala Asp
             80                  85                  90 aaa tcc tcc agc aca gcc tac att ttg ctc agc agc ctg acc tct gag    337
```

```
Lys Ser Ser Ser Thr Ala Tyr Ile Leu Leu Ser Ser Leu Thr Ser Glu
            95                 100                 105 gac tct gcg atg tat ttc tgt gta agg agt gac gac ttt gac tac tgg      385
Asp Ser Ala Met Tyr Phe Cys Val Arg Ser Asp Asp Phe Asp Tyr Trp
    110                 115                 120 ggc cag ggc acc act ctc aca gtc tcc tca ggt gga ggc ggt agc caa      433
Gly Gln Gly Thr Thr Leu Thr Val Ser Ser Gly Gly Gly Gly Ser Gln
125                 130                 135                 140 att gtt ctc acc cag tcg cca gca atc atg tct gca tct cca ggg gag      481
Ile Val Leu Thr Gln Ser Pro Ala Ile Met Ser Ala Ser Pro Gly Glu
                145                 150                 155 aag gtc acc ata acc tgc agt gcc agc tca agt gta agt tac atg cac      529
Lys Val Thr Ile Thr Cys Ser Ala Ser Ser Ser Val Ser Tyr Met His
            160                 165                 170 tgg ttc cag cag aag cca ggc act ttt ccc aaa ctc tgg att tat agc      577
Trp Phe Gln Gln Lys Pro Gly Thr Phe Pro Lys Leu Trp Ile Tyr Ser
        175                 180                 185 aca tcc aac ctg gct tct gga gtc cct act cgc ttc agt ggc agt gga      625
Thr Ser Asn Leu Ala Ser Gly Val Pro Thr Arg Phe Ser Gly Ser Gly
    190                 195                 200 tct ggg acc tct tac tct ctc aca atc agc cga atg gag gct gaa gat      673
Ser Gly Thr Ser Tyr Ser Leu Thr Ile Ser Arg Met Glu Ala Glu Asp
205                 210                 215                 220 gct gcc act tat tac tgc cag caa agg acg agt tat cca ccc acg ttc      721
Ala Ala Thr Tyr Tyr Cys Gln Gln Arg Thr Ser Tyr Pro Pro Thr Phe
                225                 230                 235 ggc tcg ggg aca aag ttg gag ata aaa gac tac aag gat gac gac gat      769
Gly Ser Gly Thr Lys Leu Glu Ile Lys Asp Tyr Lys Asp Asp Asp Asp
            240                 245                 250 aag tga taagcggccg caat                                              789
Lys

<210> SEQ ID NO 6
<211> LENGTH: 253
<212> TYPE: PRT
<213> ORGANISM: Artificial Sequence
<220> FEATURE:
<223> OTHER INFORMATION: Description of Artificial Sequence:an
      artificially synthesized peptide sequence

<400> SEQUENCE: 6

Met Arg Trp Ser Trp Ile Phe Leu Phe Leu Leu Ser Ile Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asp Tyr Phe Ile His Trp Val Lys Gln Arg Pro Gly Gln Gly Leu
    50                  55                  60

Glu Trp Ile Gly Trp Ile Phe Pro Gly Asp Asp Thr Thr Asp Tyr Asn
65                  70                  75                  80

Glu Lys Phe Arg Gly Lys Thr Thr Leu Thr Ala Asp Lys Ser Ser Ser
                85                  90                  95

Thr Ala Tyr Ile Leu Leu Ser Ser Leu Thr Ser Glu Asp Ser Ala Met
            100                 105                 110

Tyr Phe Cys Val Arg Ser Asp Asp Phe Asp Tyr Trp Gly Gln Gly Thr
        115                 120                 125

Thr Leu Thr Val Ser Ser Gly Gly Gly Gly Ser Gln Ile Val Leu Thr
    130                 135                 140
```

```
Gln Ser Pro Ala Ile Met Ser Ala Ser Pro Gly Glu Lys Val Thr Ile
145                 150                 155                 160

Thr Cys Ser Ala Ser Ser Ser Val Ser Tyr Met His Trp Phe Gln Gln
                165                 170                 175

Lys Pro Gly Thr Phe Pro Lys Leu Trp Ile Tyr Ser Thr Ser Asn Leu
            180                 185                 190

Ala Ser Gly Val Pro Thr Arg Phe Ser Gly Ser Gly Ser Gly Thr Ser
        195                 200                 205

Tyr Ser Leu Thr Ile Ser Arg Met Glu Ala Glu Asp Ala Ala Thr Tyr
    210                 215                 220

Tyr Cys Gln Gln Arg Thr Ser Tyr Pro Pro Thr Phe Gly Ser Gly Thr
225                 230                 235                 240

Lys Leu Glu Ile Lys Asp Tyr Lys Asp Asp Asp Lys
            245                 250

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized adapter sequence

<400> SEQUENCE: 7
aattcccagc acagtggtag ataagtaag                                            29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:an
      artificially synthesized adapter sequence

<400> SEQUENCE: 8
tcgacttact tatctaccac tgtgctggg                                            29

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9
caggggccag tggatagact gatg                                                 24

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10
gctcactgga tggtgggaag atg                                                  23

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:an
```

```
            artificially synthesized primer sequence

<400> SEQUENCE: 11
cctgaattcc accatgcgat ggagctggat cttc                              35

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12
aatttggcta ccgcctccac ctgaggagac tgtgagagtg gtgccct                47

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13
tcctcaggtg gaggcggtag ccaaattgtt ctcacccagt cgccagc                47

<210> SEQ ID NO 14
<211> LENGTH: 68
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
attgcggccg cttatcactt atcgtcgtca tccttgtagt cttttatctc caactttgtc  60
cccgagcc                                                           68
```